(12) United States Patent
Loh et al.

(10) Patent No.: US 9,278,946 B2
(45) Date of Patent: Mar. 8, 2016

(54) SMALL MOLECULE CATALYST FOR 5-HYDROXYMETHYLFURFURAL PRODUCTION FROM SACCHARIDES

(71) Applicant: NANYANG TECHNOLOGICAL UNIVERSITY, Singapore (SG)

(72) Inventors: Teck Peng Loh, Singapore (SG); Peng Wang, Singapore (SG); Daniel Hartoyo Lukamto, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 14/411,720

(22) PCT Filed: Jul. 1, 2013

(86) PCT No.: PCT/SG2013/000272
§ 371 (c)(1),
(2) Date: Dec. 29, 2014

(87) PCT Pub. No.: WO2014/003690
PCT Pub. Date: Jan. 3, 2014

(65) Prior Publication Data
US 2015/0166499 A1    Jun. 18, 2015

Related U.S. Application Data

(60) Provisional application No. 61/666,067, filed on Jun. 29, 2012.

(51) Int. Cl.
*C07D 307/50*    (2006.01)
(52) U.S. Cl.
CPC .................................. *C07D 307/50* (2013.01)
(58) Field of Classification Search
CPC .................................................... C07D 307/50
USPC ........................................................ 549/498
See application file for complete search history.

(56) References Cited

U.S. PATENT DOCUMENTS

2008/0033187 A1    2/2008    Zhao et al.

FOREIGN PATENT DOCUMENTS

WO    2013/049424 A1    4/2013

OTHER PUBLICATIONS

Thomas S. Hansen, et al., "Synergy of boric acid and added salts in the catalytic dehydration of hexoses to 5-hydroxymethylfurfural in water", Green Chemistry, The Royal Society of Chemistry, 2011, pp. 109-114, vol. 13.
International Search Report of PCT/SG2013/000272, dated Nov. 18, 2013. [PCT/ISA/210].
Sugihara et al., Cyclic Benzeneboronate Esters, J. Am. Chem. Soc., Nov. 18, 1957, vol. 80, No. 10, pp. 2443-2446.
Binder et al., Mechanistic insights on the conversion of sugars into 5-hydroxymethylfurfural, Energy & Environmental Science, 2010, vol. 3, No. 6, pp. 765-771.
Binder et al., Simple Chemical Transformation of Lignocellulosic Biomass into Furans for Fuel and Chemicals, J. Am. Chem. Soc., Jan. 21, 2009, vol. 131, No. 5, pp. 1979-1985.
Pizer et al., Mechanism of Boron Acid/Polyol Complex Formation. Comments on the Trigonal/Tetrahedral Interconversion on Boron, Polyhedron, Pergamon, Jan. 8, 1996, vol. 15, No. 19, pp. 3411-3416.
Kustin et al., Temperature-Jump Study of the Rate and Mechanism of the Boric Acid-Tartaric Acid Complexation, J. Am. Chem. Soc., Jan. 15, 1969, vol. 91, No. 2, pp. 317-322.
Martichonok et al., Cysteine Proteases such as Papain are not Inhibited by Substrate Analogue Peptidyl Boronic Acids, Bioorg. Med. Chem. 1997, vol. 5, No. 4, pp. 679-684.
Yan et al., Catalytic conversion of glucose to 5-hydroxymethylfurfural over SO4 2-ZrO2 and SO4 2-/ZrO2-Al2O3 solid acid catalysts, Catal. Commun., 2009, vol. 10, No. 11, 1558-1563.
Cukalovic et al., Production of biobased HMF derivatives by reductive amination, Green Chem., 2010, vol. 12, No. 7, pp. 1201-1206.
Bettman et al., Dissociation Constants of Organic Boric Acids, J. Am. Chem. Soc., 1934, vol. 56,1865-1870.
Yabroff et al., The Relative Strengths of Some Hydrocarbon Derivatives of Boric Acid, J. Am. Chem. Soc., Sep. 1934, vol. 56, pp. 1850-1857.
Branch et al., The Dissociation Constants of the Chlorophenyl and Phenetyl Boric Acids, J. Am. Chem. Soc., Apr. 1934, vol. 56, pp. 934-941.
Babcock et al., Dynamics of Boron Acid Complexation Reactions. Formation of 1:1 Boron Acid-Ligand Complexes, Inorg. Chem., 1980, vol. 19, No. 1, pp. 56-61.
Kondo et al, Specific Complexation of Disaccharides with Diphenyl-3,3'-diboronic Acid that Can Be Detected by Circular Dichroism, Tetrahedron, 1992, vol. 48, No. 38, pp. 8239-8252.
Shinkai et al., Molecular Recognition of Mono- and Di-saccharides by Phenylboronic Acids in Solvent Extraction and as a Monolayer, J. Chem. Soc. Chem. Commun., 1991, pp. 1039-1041.
Pizer et al., Equilibria and Reaction Mechanism of the Complexation of Methylboronic Acid with Polyols, Inorg. Chem., 1992, vol. 31, No. 15, pp. 3243-3247.
Lorand et al., Polyol Complexes and Structure of the Benzeneboronate Ion, J. Org. Chem., Jun. 1959, vol. 24, pp. 769-774.
Patil et al., Formation and Growth of Humins via Aldol Addition and Condensation during Acid-Catalyzed Conversion of 5-Hydroxymethylfurfural, Energy Fuels, 2011, vol. 25, pp. 4745-4755.

(Continued)

*Primary Examiner* — Taofiq A Solola
(74) *Attorney, Agent, or Firm* — Sughrue Mion, PLLC

(57) ABSTRACT

The disclosure provides the use of aryl or heteroaryl boronic acid in the preparation of 5-(hydroxymethyl)fufural (HMF) from saccharides. The aryl or heteroaryl boronic bearing electron-withdrawing groups on the aryl or heteroaryl ring of the boronic acid provided good yields. The disclosure provides a method for preparing HMF from saccharides in the presence of aryl or heteroaryl boronic acid. The disclosure provides a method for converting a saccharide other than fructose in fructose via a dehydrogenation reaction catalyzed by aryl or heteroaryl boronic acid.

19 Claims, 34 Drawing Sheets

(56) References Cited

OTHER PUBLICATIONS

Zhang et al., An Unexpected Reaction between 5-Hydroxymethylfurfural and Imidazolium-Based Ionic Liquids at High Temeratures, Molecules, 2011, vol. 16, pp. 8463-8474.
Qi et al, Efficient process for conversion of fructose to 5-hydroxymethylfurfural with ionic liquids, Green Chem., Sep. 2009, vol. 11, No. 9, pp. 1327-1331.
Qi et al., Efficient Catalytic Conversion of Fructose into 5-Hydroxymethylfurfural in Ionic Liquids at Room Temperature, ChemSusChem, 2009, vol. 2, No. 10, pp. 944-946.
Qi et al., Sulfated zirconia as a solid acid catalyst for the dehydration of fructose to 5-hydroxymethylfurfural, Catal. Commun., 2009, vol. 10, No. 13, pp. 1771-1775.
Haworth et al., The Conversion of Sucrose into Furan Compounds. Part I. 5-Hydroxymethylfurfuraldehyde and Some Derivatives, J. Chem. Soc., Jan. 1944, pp. 667-670.
Haworth et al., CCI.—The Constitution of the Disaccharides. Part XIII. The y-Fructose Residue in Sucrose., J. Chem. Soc., 1927, pp. 1513-1526.
Amarasekara et al., Mechanism of the dehtdration of D-fructose to 5-hydroxymethylfurfural in dimethyl sulfoxide at 150 degrees C: an NMR study, Carbohydr. Res., 2008, vol. 343, pp. 3021-3024.
Antal et al., Mechanism of formation of 5-(hydroxymethyl)-2-furalde-hyde from D-fructose and sucrose, Carbohydr. Res., 1990, vol. 199, No. 1, pp. 91-109.
Assary et al., Theoretical Study of 1,2-Hydride Shift Associated with the Isomerization of Glyceraldehyde to Dihydroxy Acetone by Lewis Acid Active Site Models, J. Phys. Chem. A, 2011, vol. 115, No. 31, pp. 8754-8760.
Bhosale et al., Molecular and Industrial Aspects of Glucose Isomerase, Microbiol. Rev. Jun. 1996, vol. 60, No. 2, pp. 280-300.
Iwasawa et al., A Convenient Method for Dihydroxylation of Olefins by the Combined Use of Osmium Tetroxide and Dihydroxyphenylborane, Chem. Lett., 1988, pp. 1721-1724.
Narasaka et al., Phenylboronic Acid as a Template in the Diels-Alder Reaction, Synthesis, Dec. 1991, pp. 1171-1172.
Draffin et al., O2,O3:O4,O5-Bis(phenylboranediyl)-b-D-fructopyranose acetone solvate, Organic Papers, Acta Cryst., 2004, vol. E60, pp. 1520-1522.
Stahlberg et al., Metal-Free Dehydration of Glucose to 5-(Hydroxymethyl)furfural in Ionic Liquids with Boric Acid as a Promoter, Chem.-Eur. J., 2011, vol. 17, No. 5, pp. 1456-1464.
Scott et al., Quantitative Spectrometric Determination Specific for Mannose, Anal. Chem., Apr. 1974, vol. 46, No. 4, pp. 594-597.
Khokhlova et al., The First Molecular Level Monitoring of Carbohydrate Conversion to 5-Hydroxymethylfurfural in Ionic Liquids. B2O3—An Efficient Dual-Function Metal-Free Promoter for Environmentally Benign Applications, ChemSusChem, 2012, vol. 5, pp. 783-789.
Kamm, Production of Platform Chemicals and Synthesis Gas from Biomass, Angew. Chem. Int. Ed., 2007, vol. 46, pp. 5056-5058.
Matson et al., One-Pot Catalytic Conversion of Cellulose and of Woody Biomass Solids to Liquid Fuels, J. Am. Chem. Soc., 2011, vol. 133, pp. 14090-14097.
Mascal et al., Direct, High-Yield Conversion of Cellulose into Biofuel, Angew. Chem.-Int. Edit., 2008, vol. 47, pp. 7924-7926.
Corma et al., Chemical Routes for the Transformation of Biomass into Chemicals, Chem. Rev., 2007, vol. 107, No. 6, pp. 2411-2502.
Rosatella et al., 5-Hydroxymethylfurfural (HMF) as a building block platform: Biological properties, synthesis and synthetic applications, Green Chem., 2011, vol. 13, No. 4, pp. 754-793.
Stahlberg et al., Synthesis of 5-(Hydroxymethyl)furfural in Ionic Liquids: Paving the Way to Renewable Chemicals, ChemSusChem, 2011, vol. 4, No. 4, pp. 451-458.
Nishiyama et al., Crystal Structure and Hydrogen-Bonding System in Cellulose Iβ from Synchrotron X-ray and Neutron Fiber Diffraction, J. Am. Chem. Soc., 2002, vol. 124, No. 31, pp. 9074-9082.
Isogai et al., Dissolution of cellulose in aqueous NaOH solutions, Cellulose, 1998, vol. 5, pp. 309-319.
Pinkert et al., Reflections on the Solubility of Cellulose, Ind. Eng. Chem. Res., 2010, vol. 49, No. 22, pp. 11121-11130.
Rantwijk et al., Biocatalytic transformations in ionic liquids, Trends Biotechnol., Mar. 2003, vol. 21, No. 3, pp. 131-138.
Zhao et al., Metal Chlorides in Ionic Liquid Solvents Convert Sugars to 5-Hydroxymethylfurfural, Science, Jun. 15, 2007, vol. 316, pp. 1597-1600 (5 pages total).
Hu et al., Efficient conversion of glucose into 5-hydroxymethylfurfural catalyzed by a common Lewis acid SnCl4 in an ionic liquid, Green Chem., 2009, Green Chem. 2009, vol. 11, No. 11, pp. 1746-1749.
Zhang et al., Catalytic Conversion of Carbohydrates into 5-Hydroxymethylfurfural by Germanium(IV) Chloride in Ionic Liquids, ChemSusChem, 2011, vol. 4, No. 1, pp. 131-138.
Yong et al., Efficient Catalytic System for the Selective Production of 5-Hydroxymethylfurfural from Glucose and Fructose, Angew. Chem.-Int. Edit., 2008, vol. 47, No. 48, pp. 9345-9348.
Li et al., Direct conversion of glucose and cellulose to 5-hydroxymethylfurfural in ionic liquid under microwave irradiation, Tetrahedron Lett., 2009, vol. 50, No. 38, pp. 5403-5405.
Qi et al., Selective Conversion of D-Fructose to 5-Hydroxymethylfurfural by Ion-Exchange Resin in Acetone/Dimethyl sulfoxide Solvent Mixtures, Ind. Eng. Chem. Res., 2008, vol. 47, No. 23, pp. 9234-9239.
Matteson et al., Asymmetric Alkyldifluoroboranes and Their Use in Secondary Amine Synthesis, Org. Lett., 2002, vol. 4, No. 13, pp. 2153-2155.
Holloczki et al., Carbenes in ionic liquids, NewJ. Chem., 2010, vol. 34, pp. 3004-3009.
Scholten et al., On the involvement of NHC carbenes in catalytic reactions by iridium complexes, nanoparticle and bulk metal dispersed in imidazolium ionic liquids, Dalton Trans., 2007, pp. 5554-5560.
Seidl et al., NMR investigation of steric effects in alkyl- and haloadamantanes, J. Phys. Org. Chem., 2005, vol. 18, pp. 162-166.
Seidl et al., NMR chemical shifts as probes for steric effects in mono- and disubstituted adamantanes, J. Phys. Org. Chem., 2002, vol. 15, pp. 801-807.
Pinkert et al., Ionic Liquids and Their Interaction with Cellulose, Chem. Rev., 2009, vol. 109, No. 12, pp. 6712-6728.
Harvey, World headed for irreversible climate change in five years, IEA warns, http://www.guardian.co.uk (accessed Nov. 25, 2011). 5 pages total.
Gottlieb et al., NMR Chemical Shifts of Common Laboratory Solvents as Trace Impurities, J. Org. Chem., 1997, vol. 62, No. 21, pp. 7512-7515.
Gurst, NMR and the Structure of D-Glucose, J. Chem. Educ., Dec. 1991, vol. 68, No. 12, pp. 1003-1004.
International Preliminary Report on Patentability for PCT/SG2013/000272 dated Jan. 8, 2015.

SMALL MOLECULE CATALYST FOR 5-HYDROXYMETHYLFURFURAL PRODUCTION FROM SACCHARIDES

CROSS REFERENCE TO RELATED APPLICATIONS

This application is a National Stage of International Application No. PCT/SG2013/000272 filed Jul. 1, 2013, claiming priority based on U.S. Provisional Patent Application No. 61/666,067, filed Jun. 29, 2012, the contents of all of which are incorporated herein by reference in their entirety.

FIELD OF THE INVENTION

The present invention relates generally to the use of aryl or heteroaryl boronic acid as a catalyst for the synthesis of 5-hydroxymethylfurfural (HMF) from saccharides and a method for preparing microencapsulating HMF using aryl or heteroaryl boronic acid.

BACKGROUND OF THE DISCLOSURE

Fossil fuel is currently still the major source of functionalized carbon skeleton for the chemical and energy industry. However, as prices of oil increase and fossil fuel reservoirs deplete, new demands for molecules from renewable resources will be created, and biomass conversions using bio-refineries are expected to play a more significant role in the future.[1] One important advantage of using biomass is that the carbon source is renewable as it ultimately comes from atmospheric carbon dioxide, harvested photosynthetically to form simple sugars and their polymers such as cellulose. Furthermore, since cellulose is the most abundant organic molecule on earth, it has recently become the principle focus of emerging renewable carbon-fuel technology.[2] The earliest form of biomass conversion was from lignocellulose, an abundant material comprising of cellulose, hemicellulose and lignin, and its earliest use was the commercial production of ethanol through a fermentation process in the early 20th century[3]. Cellulose and hemicellulose were regarded as of particularly high importance because their glucose monomers were the source of carbon in the production of ethanol, although other types of monosaccharide are also present in hemicellulose. However, more complex functionalized carbon skeletons are needed if biomass was to replace fossil fuel as the raw material for precursors in synthetic polymer and pharmaceutical production.[4]

One of the most promising chemical building blocks, among those previously considered, is 5-(hydroxymethyl) furfural (HMF), first discovered by Dull, G. in 1895.[5] HMF holds the potential to securing future energy and chemical needs as it is obtainable from renewable sources such as non-food crops, avoiding competition with food. HMF is synthesized mainly by the dehydration of monosaccharides, although disaccharides or polysaccharides such as sucrose, cellobiose, inulin and cellulose can be used as starting materials with a necessary initial hydrolysis step for depolymerisation.[6]

One example of the use of HMF is its conversion to 2,5-dimethylfuran (DMF) whose energy content of 31.5 MJ L$^{-1}$ is comparable to that of gasoline (35 MJ L$^{-1}$) and 40% greater than that of ethanol (23 MJ L$^{-1}$).[7] Other uses include its conversion to other important molecules in the chemical industry such as levulinic acid (LA)—a precursor to plastics, 2,5-diformylfuran (DFF)—an intermediate to pharmaceuticals, 2,5-furandicarboxylic acid (FDA)—a precursor to polyester, and many more[8].

Fortunately, the most important source of HMF remains to be that from cellulose—the major component of non-food crops (Scheme 1).

Scheme 1: Concept of HMF Production from Cellulose

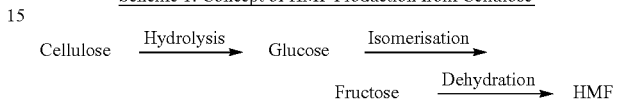

Research in this area is relatively new and there are still many challenges to overcome. The first challenge to overcome in using cellulose-based feedstock is its dissolution. Cellulose has a highly crystalline structure with extensive network of intra- and inter-molecular hydrogen-bonds within and between parallel chains, respectively, rendering it insoluble in most solvents.[9] Many attempts have been made to solve this problem and the most successful methods are those using (1) NaOH and urea at low temperatures, and (2) ionic liquid (IL).[10] However, since monosaccharide dehydration is catalysed by acids, IL is the better solvent for a one-pot HMF production from cellulose after hydrolysis to glucose. Furthermore, ILs have many advantages over other solvents.[11]

The second challenge to HMF production from cellulose is that, while the dehydration of fructose to HMF is known to occur readily[12], the dehydration of its glucose monomer after hydrolysis proceeds slowly due to the slow first-step isomerisation to fructose (Scheme 1).

One explanation for this is the fact that there is a much lower abundance of acyclic isomers for glucose compared to fructose.[13] Glucose can form stable ring structures, slowing down its isomerization to fructose and thus conversion to HMF. Many attempts have been made to address this bottleneck, using either Brönsted acid or Lewis acid catalysts.[14] However, Brönsted acids catalyse more unwanted side-reactions due to its strong aqueous acidity.[13b]

In recent years, catalysts for carbohydrate dehydration have undergone a remarkable process of evolution, and several Lewis acid catalysts have been reported[6]. However, the yields remain lower, and unwanted side-reactions remain higher, than are practically desirable for many of these Lewis acid catalysts reported—with the exception of transition metal chlorides such as GeCl$_4$, SnCl$_4$, CrCl$_3$ and CrCl$_2$.[12,15] Anhydrous CrCl$_3$ is currently the best known catalyst for glucose dehydration to HMF. Discovered by Zhao et al., the group reported HMF yields of 68-70% for the dehydration of glucose in 1-ethyl-3-methylimidazolium chloride ([EMIm] Cl) IL solvent at a temperature of 100° C. for 3 hours, at 6 mol % catalyst loading with respect to glucose (Scheme 2).[12] This result was also supported by work done by others.[16] However, chromium chloride salts are known to be toxic and environmentally hazardous, limiting its practical scale-up in industrial processes[17].

Scheme 2: Summary of the glucose dehydration with prior art catalyst $CrCl_2$

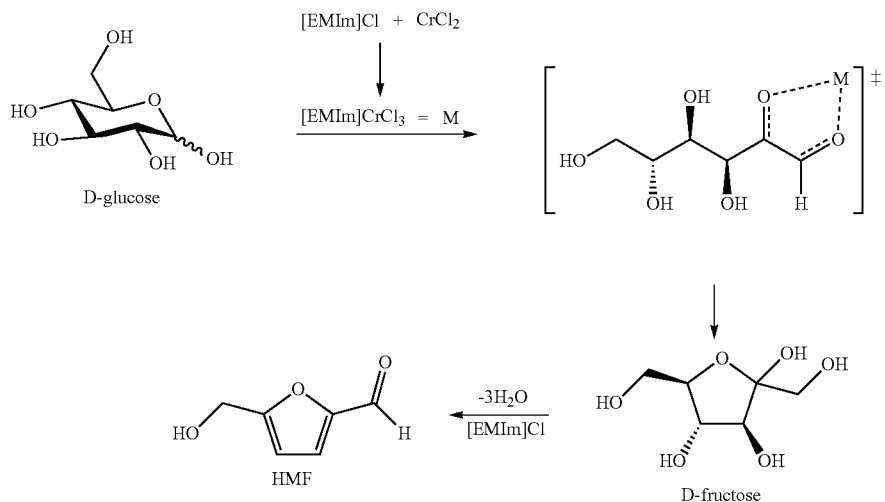

On the other hand, boron-based catalysts such as boronic acids may be considered to be non-metals and are known to possess low toxicity, as evidenced by their applications in medicine. Furthermore, from an environmental perspective, boronic acids will degrade to the relatively benign boric acid in air and aqueous media, although the fate of the rest of the molecule depends on the nature of its substituent. Despite these advantages, however, no study has been done on the use of boronic acids as catalysts for HMF production, even though it is known to be a Lewis acid by virtue of its vacant p-orbital. Khokhlova, E. A. et al. reported on the mechanistic study of $B(OH)_3$, $B_2O_3$ and $PhB(OH)_3$ in carbohydrate conversion to HMF using NMR studies, although no measurement of HMF yields were made.[18] As early as 1974, Scott, R. W. et al. used boric acids in the dehydration of mannose, while in 2010, Stahlberg, T. et al. discovered $B(OH)_3$'s role in the dehydration of glucose to HMF with a reported yield of up to 41.5% in [EMIm]Cl at a temperature of 120° C. for 3 hours, and at 100 mol % catalyst amount with respect to glucose[19,20].

Boronic acids' entry into biological and medicinal applications only started in the early 1990s. Of its biological applications, the most relevant for discussion are its role in glucose sensors and transmembrane transporters, both of which require the selective interaction of boronic acid with 1,2 and 1,3 diols on the glucose molecule to form boronate ester complexes with 5- and 6-membered rings, respectively (Scheme 3b). It was observed that the formation constant for diol boronate anion complex ($K_{tet}$) was much higher than the formation constant for diol boronic acid complex ($K_{trig}$), highlighting its preference for the anionic form (Scheme 3a). One reason given was that the neutral diol boronic acid complex deviated from its ideal trigonal planar bond angle of 120° due to an O—B—O angle compression to 113°, while the anionic complex provides a closer match to the ideal tetrahedral geometry bond angle.

Scheme 3: Conversion from neutral and trigonal planar sp2 boron into anionic tetrahedral sp3 boron: a) aqueous solution of 1,2 diol; (b) with D-glucose

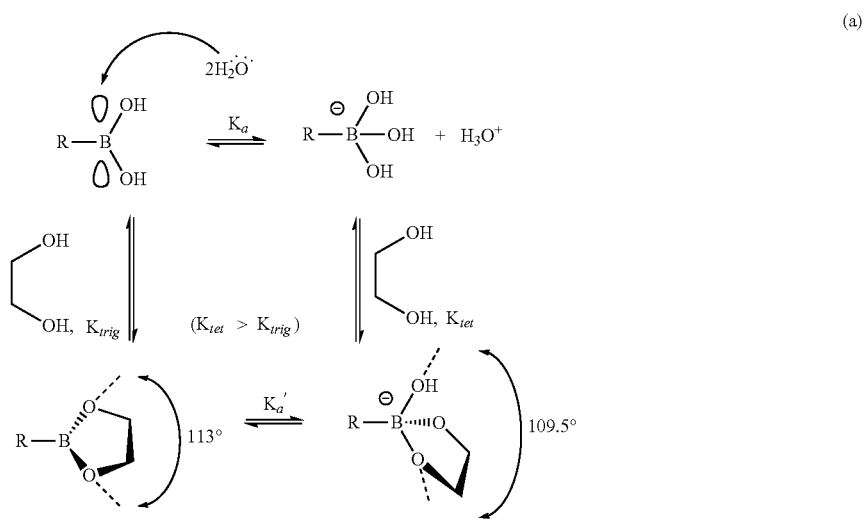

(a)

-continued

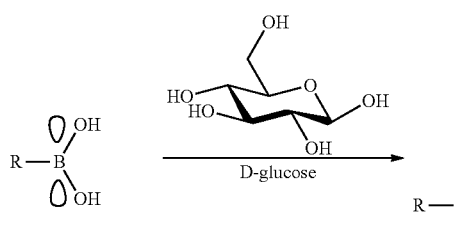
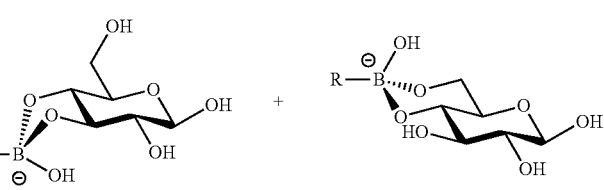

However, there is still a need to provide further and improved catalysts to be used in the conversion of saccharides such as glucose or cellulose in HMF and thereby provide a more efficient and economic process for HMF production.

SUMMARY OF THE INVENTION

The present invention addresses these needs by providing new and improved method for the production of HMF starting from saccharides or cellulose.

In a first aspect, the disclosure provides a methods for preparing HMF, the method comprising reacting a saccharide such as cellulose or glucose with an aryl or heteroaryl boronic acid, preferably with an aryl or heteroaryl boronic acid of formula (I):

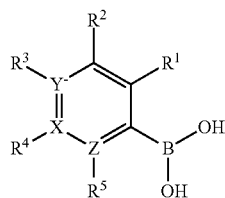

wherein in formula (I) each of X, Y and Z are independently C, N, O, or S, or when at least one of Y, X, or Z is N or O or S, the ring comprising Y, X and Z may be a 5 or 6 membered ring;

$R^1$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;

$R^2$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;

$R^3$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;

$R^4$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;

$R^5$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;

or wherein
independently each of $R^1$ and $R^2$, $R^2$ and $R^3$, $R^3$ and $H^4$, $R^4$ and $R^5$ taken together form an optionally substituted ring of 5 or 6 atoms wherein the atoms are independently selected from C, N, S or O; and wherein
R is selected from H, $C_1$-$C_6$ alkyl;
$R^6$ is selected from H, $C_1$-$C_6$ alkyl, OH, Ph, Cl, Br.

In a second aspect, the disclosure provides the use of aryl or heteroaryl boronic acid as catalyst for the preparation of HMF, preferably with an aryl or heteroaryl boronic acid of formula (I) as defined above.

In a third aspect, the disclosure provides a method for isomerizing glucose to fructose in the presence of aryl or heteroaryl boronic acid as catalyst, preferably with an aryl or heteroaryl boronic acid of formula (I) as defined above.

Compound of the following formula 2d

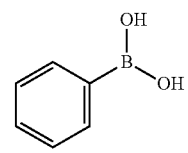

may not be part of the present invention.

DESCRIPTION OF THE DRAWINGS

The invention will be better understood with reference to the detailed description when considered in conjunction with the non-limiting examples and the accompanying drawings, in which:

FIG. 1 shows the prior art isomerization of glucose to fructose.

FIG. 6 shows the HMF yields obtained by varying the substituent on the aryl ring of the boronic acid.

FIG. 8 shows study on catalyst 2p at 20% at different condition.

DETAILED DESCRIPTION

The present invention provides in a first aspect a use of aryl or heteroaryl boronic acid for the preparation of HMF with the proviso that the aryl boronic acid is not a compound of formula 2d as defined above. The starting material used in the preparation of HMF are saccharides such as monosaccharides such as glucose, disaccharides such as sucrose, oligosaccharides, and polysaccharides such as cellulose.

It has been seen that the presence of one or more substituents on the aryl or heteroaryl ring of the aryl or heteroaryl boronic acid having an electro withdrawing action improve the conversion of a saccharide into fructose via dehydration of the saccharide to fructose. Thereby, the efficiency of the process for the preparation of HMF is improved.

Figure 10:
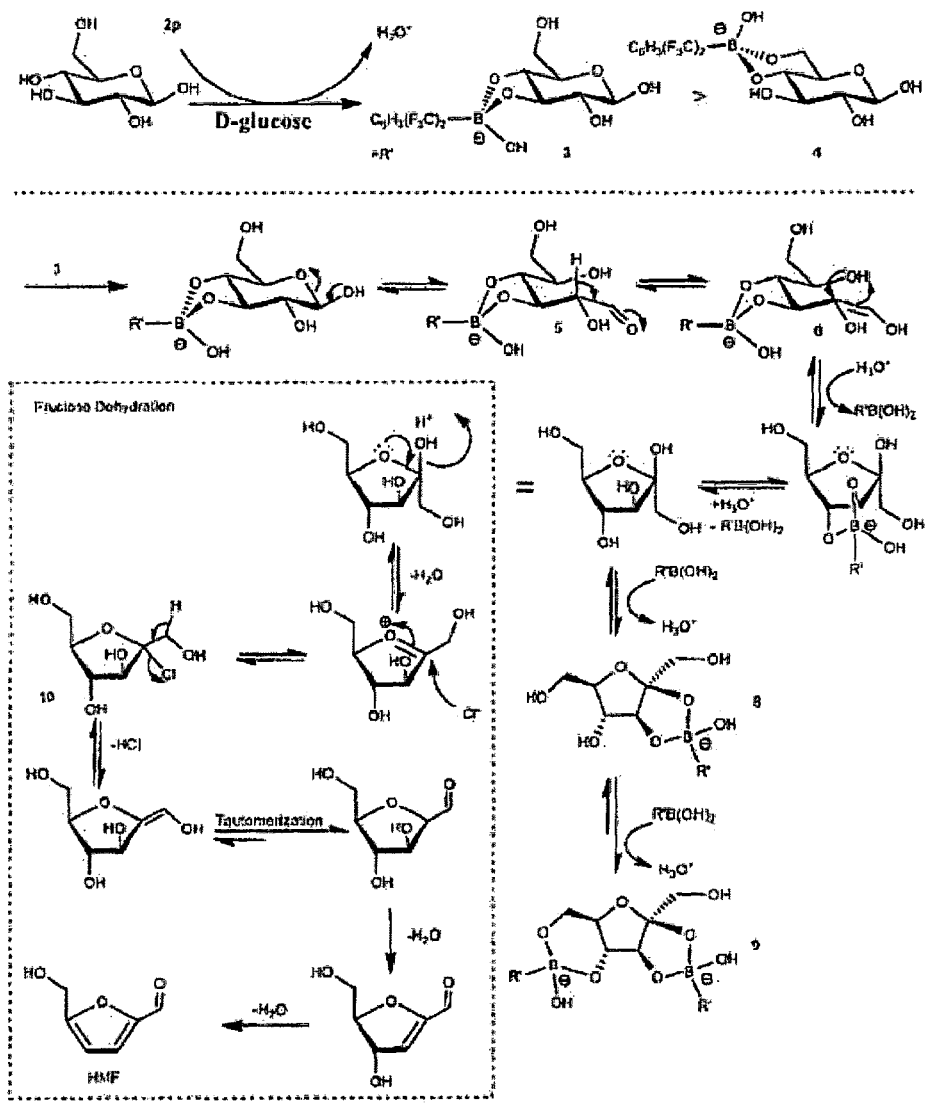
FIG. 10 illustrates the mechanism for overall glucose dehydration to HMF.

The proposed dehydration mechanism for saccharides is reported in FIG. 10 wherein glucose is used as a saccharide and catalyst 2p according to the inventions is used. Cellulose dehydration is similar to glucose dehydration with an added depolymerization step.

In the mechanism proposed, the complexes formed are anionic, and largely similar to the mechanism proposed by Stahlberg, T. et al. for $B(OH)_3$.[20] Previous studies found that the $sp^2$ neutral boronate complexes are more acidic than the free boronic acid, making the $sp^3$ hydroxyboronate anionic complexes prevalent in the reaction.[32] Furthermore, when the boron was in its anionic tetrahedral form, the rate of boronic acid-diol complexation was significantly faster.[29a,33 34] Kinetics also improved when pH was increased and when the ligand was in its protonated form.[33-34] These observations were explained to be due to the expulsion of the leaving group ($H_2O$) and the minimisation of charge repulsion upon complexation of sugars to the anionic tetrahedral boronate species (scheme 4).[30a]

Scheme 4: Transition state of complex formation

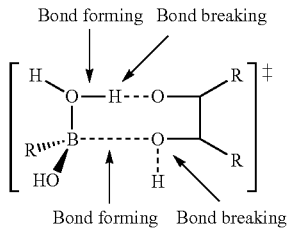

The mechanism is disclosed in FIG. 10: 2p first complexes with glucose to form 3, which is believed to be thermodynamically more stable than 4, with the loss of one equivalent of hydroxonium ion. 3 proceeded to open the glucopyranose ring to its acyclic form, 5. The reaction continued via the enediol intermediate, 6, to produce the fructofuranose cyclic boronate ester 7. Due to the strained trans-2,3-boronate ester conformation, the boronic species is released in the presence of acid to produce the fructose molecule. From here, fructose proceeds to form HMF via dehydration, releasing 3 equivalents of water and 1 equivalent of HCl.

Hence, the present invention is directed to aryl and heteroaryl boronic acids that are useful in the conversion of saccharides in fructose. Fructose in turn is converted into HMF via dehydration (FIG. 10). The aryl or heteroaryl boronic acids of the invention are useful for an efficient preparation of HMF starting from saccharides even as a one pot preparation. The present invention is further directed to aryl and heteroaryl boronic acids that are useful in the conversion of saccharides in fructose with the proviso that the aryl boronic acid is not a compound of formula 2d as disclose above.

In an embodiment of the first aspect of the present invention, the aryl or heteroaryl boronic acid are of formula (I)

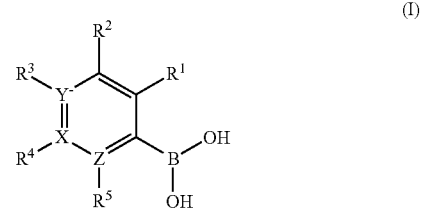

wherein
each of X, Y and Z are independently C, N, O, or S, or when at least one of Y, X, or Z is N or O or S, the ring may be a 5 membered ring;
$R^1$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;
$R^2$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;
$R^3$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;
$R^4$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;
$R^5$ H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;
or wherein
independently each of $R^1$ and $R^2$, $R^2$ and $R^3$, $R^3$ and $R^4$, $R^4$ and $R^5$ taken together form an optionally substituted ring of 5 or 6 atoms wherein the atoms are independently selected from C, N, S or O; and
wherein
R is selected from H, $C_1$-$C_6$ alkyl;
$R^6$ is selected from H, $C_1$-$C_6$ alkyl, OH, Ph, Cl, Br.

In a further embodiment of the first aspect of the present invention, the aryl or heteroaryl boronic acid are of formula (I)

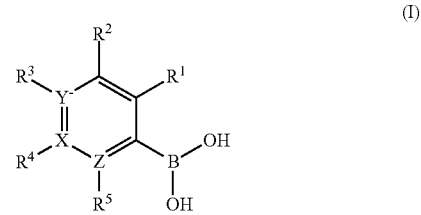

wherein
each of X, Y and Z are independently C, N, O, or S, or when at least one of Y, X, or Z is N or O or S, the ring may be a 5 membered ring;
$R^1$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;
$R^2$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$alkoxy, $C_2$-$C_6$ alkenyl, $C_2$-$C_6$ alkynyl, —$CF_3$, —$CCl_3$, CHO, $COR^6$;

$R^3$ is H, F, Cl, Br, I, NO$_2$, CN, alkyl, OH, —NH$_2$, —NHR$_2$, —N(R)$_2$, —SO$_2$CH$_3$, SO$_3$H, C$_1$-C$_6$alkoxy, C$_2$-C$_6$ alkenyl, C$_2$-C$_6$ alkynyl, —CF$_3$, —CCl$_3$, CHO, COR$^6$;

$R^4$ is H, F, Cl, Br, I, NO$_2$, CN, alkyl, OH, —NH$_2$, —NHR$_2$, —N(R)$_2$, —SO$_2$CH$_3$, SO$_3$H, C$_1$-C$_6$alkoxy, C$_2$-C$_6$ alkenyl, C$_2$-C$_6$ alkynyl, —CF$_3$, —CCl$_3$, CHO, COR$^6$;

$R^5$ H, F, Cl, Br, I, NO$_2$, CN, alkyl, OH, —NH$_2$, —NHR$_2$, —N(R)$_2$, —SO$_2$CH$_3$, SO$_3$H, C$_1$-C$_6$alkoxy, C$_2$-C$_6$ alkenyl, C$_2$-C$_6$ alkynyl, —CF$_3$, —CCl$_3$, CHO, COR$^6$;

or wherein independently each of $R^1$ and $R^2$, $R^2$ and $R^3$, $R^3$ and $R^4$, $R^4$ and $R^5$ taken together form an optionally substituted ring of 5 or 6 atoms wherein the atoms are independently selected from C, N, S or O; and wherein R is selected from H, C$_1$-C$_6$ alkyl;

R$^6$ is selected from H, C$_1$-C$_6$ alkyl, OH, Ph, Cl, Br with the proviso that compound of formula 2d as defined above is not a compound of formula (I).

Preferably, when the ring comprising Y, X, Z is a phenyl, at least one of radical $R^1$ to $R^5$ is not H.

Preferably, at least one of radical $R^1$ to $R^5$ is not H.

Preferably, at least one of radical $R^1$ to $R^5$ is independently selected from F, Cl, Br, I, NO$_2$, CN, —SO$_2$CH$_3$, SO$_3$H, CF$_3$, CCl$_3$, CHO, COR$_6$. More preferably, at least one of radical $R^1$ to $R^5$ is independently selected from CF$_3$, NO$_2$, Cl and CN.

Preferably, the ring comprising Y, X, Z is selected from a phenyl, naptahlene, thiophene, imidazole and pyrrole.

Preferred compounds of formula (I) are

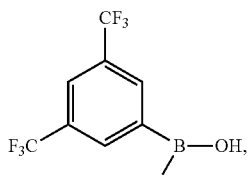
2p

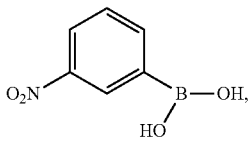
2o

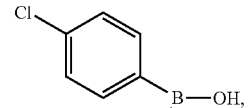
21

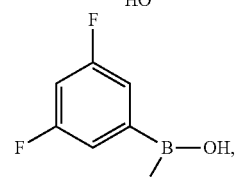

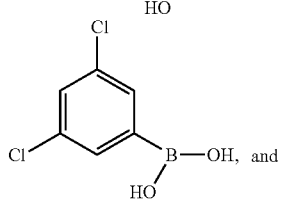
and

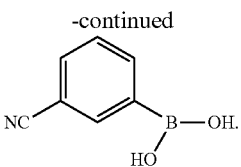

In a second aspect, the invention is directed to a process for the preparation of HMF wherein said process comprises reacting a saccharide in the presence of an aryl or hetero-aryl boronic acid. Preferably the saccharide is selected from glucose and cellulose.

In a second further aspect, the invention is directed to a process for the preparation of HMF wherein said process comprises reacting a saccharide in the presence of an aryl or hetero-aryl boronic acid with the proviso that the aryl boronic acid is not compound of formula 2d. Preferably the saccharide is selected from glucose and cellulose.

In an embodiment of the second aspect, the aryl or heteroaryl boronic acid are of formula (I)

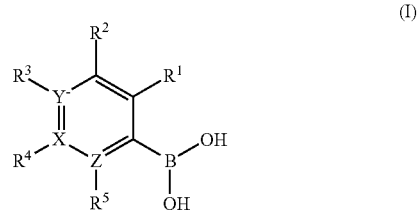
(I)

wherein each of X, Y and Z are independently C, N, O, or S, or when at least one of Y, X, or Z is N or O or S, the ring may be a 5 membered ring;

$R^1$ is H, F, Cl, Br, I, NO$_2$, CN, alkyl, OH, NH$_2$—NHR$_2$, N(R)$_2$—SO$_2$CH$_3$, SO$_3$H, C1-C6alkoxy, C$_2$-C$_6$ alkenyl, C$_2$-C$_6$ alkynyl, —CF$_3$, —CCl$_3$, CHO, COR$^6$ $R^2$ is H, F, Cl, Br, I, NO$_2$, CN, alkyl, OH, NH$_2$, —N(R)$_2$, N(R)$_3$—SO$_2$CH$_3$, SO$_3$H, C1-C6alkoxy, C$_2$-C$_6$ alkenyl, C$_2$-C$_6$ alkynyl, —CF$_3$, —CCl$_3$, CHO, COR$^6$ $R^3$ is H, F, Cl, Br, I, NO$_2$, CN, alkyl, OH, NH$_2$, —N(R)$_2$, N(R)$_3$—SO$_2$CH$_3$, SO$_3$H, C1-C6alkoxy, C$_2$-C$_6$ alkenyl, C$_2$-C$_6$ alkynyl, —CF$_3$, —CCl$_3$, CHO, COR$^6$ $R^4$ is H, F, Cl, Br, I, NO$_2$, CN, alkyl, OH, NH$_2$, —N(R)$_2$, N(R)$_3$—SO$_2$CH$_3$, SO$_3$H, C1-C6alkoxy, C$_2$-C$_6$ alkenyl, C$_2$-C$_6$ alkynyl, —CF$_3$, —CCl$_3$, CHO, COR$^6$, $R^5$ is H, F, Cl, Br, I, NO$_2$, CN, alkyl, OH, NH$_2$, —N(R)$_2$, N(R)$_3$—SO$_2$CH$_3$, SO$_3$H, C1-C6alkoxy, C$_2$-C$_6$ alkenyl, C$_2$-C$_6$ alkynyl, —CF$_3$, —CCl$_3$, CHO, COR$^6$, or wherein independently each $R^1$ and $R^2$, $R^2$ and $R^3$, $R^3$ and $R^4$, $R^4$ and $R^5$ taken together form a (optionally substituted) ring of 5 or 6 atoms wherein the atoms are independently selected from C, N, S or O; and wherein when R is selected from H, C$_1$-C$_6$ alkyl, R$^6$ is selected from H, C$_1$-C$_6$ alkyl, OH, Ph, Cl, Br.

In a further embodiment of the second aspect, the aryl or heteroaryl boronic acid are of formula (I)

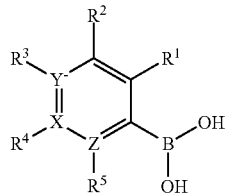

wherein
each of X, Y and Z are independently C, N, O, or S, or when at least one of Y, X, or Z is N or O or S, the ring may be a 5 membered ring;
$R^1$ is H, F, Cl, Br, I, $NO_2$, CN, alkyl, OH, $NH_2$—$NHR_2$, $N(R)_2$—$SO_2CH_3$, $SO_3H$, C1-C6alkoxy, $C_2$-$C_6$ alkenyl, $C_2$-$C_6$ alkynyl, —$CF_3$, —$CCl_3$, CHO, $COR^6$
$R^2$ is H, F, Cl, Br, I, $NO_2$, CN, alkyl, OH, $NH_2$, —$N(R)_2$, $N(R)_3$—$SO_2CH_3$, $SO_3H$, C1-C6alkoxy, $C_2$-$C_6$ alkenyl, $C_2$-$C_6$ alkynyl, —$CF_3$, —$CCl_3$, CHO, $COR^6$
$R^3$ is H, F, Cl, Br, I, $NO_2$, CN, alkyl, OH, $NH_2$, —$N(R)_2$, $N(R)_3$—$SO_2CH_3$, $SO_3H$, C1-C6alkoxy, $C_2$-$C_6$ alkenyl, $C_2$-$C_6$ alkynyl, —$CF_3$, —$CCl_3$, CHO, $COR^6$
$R^4$ is H, F, Cl, Br, I, $NO_2$, CN, alkyl, OH, $NH_2$, —$N(R)_2$, $N(R)_3$—$SO_2CH_3$, $SO_3H$, C1-C6alkoxy, $C_2$-$C_6$ alkenyl, $C_2$-$C_6$ alkynyl, —$CF_3$, —$CCl_3$, CHO, $COR^6$,
$R^5$ H, F, Cl, Br, I, $NO_2$, CN, alkyl, OH, $NH_2$, —$N(R)_2$, $N(R)_3$—$SO_2CH_3$, $SO_3H$, C1-C6alkoxy, $C_2$-$C_6$ alkenyl, $C_2$-$C_6$ alkynyl, —$CF_3$, —$CCl_3$, CHO, $COR^6$,
or wherein
independently each $R^1$ and $R^2$, $R^2$ and $R^3$, $R^3$ and $R^4$, $R^4$ and $R^5$ taken together form a (optionally substituted) ring of 5 or 6 atoms wherein the atoms are independently selected from C, N, S or O; and
wherein when
R is selected from H, $C_1$-$C_6$ alkyl,
$R^6$ is selected from H, $C_1$-$C_6$ alkyl, OH, Ph, Cl, Br,
with the proviso that compound of formula 2d as defined above is not a compound of formula (I).

Preferably, when the ring comprising Y, X, Z is a phenyl, at least one of radical $R^1$ to $R^5$ is not H.

Preferably, at least one of radical $R^1$ to $R^5$ is not H.

Preferably, at least one of radical $R^1$ to $R^5$ is independently selected from F, Cl, Br, I, $NO_2$, CN, —$SO_2CH_3$, $SO_3H$, $CF_3$, $CCl_3$, CHO, $COR_6$. More preferably, at least one of radical $R^1$ to $R^5$ is independently selected from $CF_3$, $NO_2$, Cl and CN.

Preferably, the ring comprising Y, X, Z is selected from a phenyl, naptahlene, thiophene, imidazole and pyrrole.

The starting material in the process for the preparation of HMF is a saccharide. Saccharides according to the present invention are monosaccharides such as glucose, fructose, galactose disaccharides such as sucrose and lactose, oligosaccharides, and polysaccharides such as cellulose. Preferred stating materials for the present process are cellulose and glucose.

When fructose is considered the cathalitic amounts of boronic acids ensure that fructose formed can be free to dehydrate.

Cellulose is converted into glucose via a de-polymerization step, subsequently the glucose is converted in fructose via dehydration catalyzed by the aryl or heteroaryl boronic acid. Fructose is then dehydrated to HMF. The preparation of HMF from a saccharide may be a one pot preparation.

The preparation of HMF may additional occur in the presence of a salt. The salt assists the dehydration of fructose into HMF. (FIG. 10 intermediate 10). Further, it has been observed that salts may promote a faster formation of fructose together with its dehydration to HMF. Hence salts, according to the present invention may act as co-catalyst. Salts that can be used according to the present invention are for example NaCl, $LiCl_2$, $AlCl_3$, $CuCl_3$, $Mg_2Cl$, $InCl_3$, $SnCl_4$, $CrCl_2$ and $CrCl_3$. Preferred salts according to the invention are NaCl, $Mg_2Cl$, $InCl_3$, $CrCl_2$ and $CrCl_3$.

The amount of salt used as a co-catalyst may be adjusted. The salt amount may range from 5% to 400% of mole of saccharide monomer, preferably the amount of salt is from 5% to 100% of saccharide monomer, even more preferably the amount of salt is from 6% to 40/ of moles of saccharide monomer (starting material).

"Saccharide monomer" is referred herein to the starting saccharide material for the preparation of HMF. For example if glucose is the starting material for the preparation of HMF, the mole percentage of the aryl or heteroaryl boronic acid catalyst will be calculated based on the mole of glucose. The amount of salt will be therefore 5% to 400% of the moles of glucose monomer, preferably 5% to 100% of the moles of glucose monomer, even more preferably 6% to 40% of the moles of glucose monomer.

When cellulose is used a starting material, the calculation of the mole of the boronic acid of the invention is based on the mole of glucose after the polymerization of the cellulose. The calculation may be done assuming that the cellulose is completely depolymerized.

The preparation of HMF may occur in the presence of a solvent. Typically, any solvent in which the saccharides used according to the present invention are soluble is suitable for the purpose of the present invention. Particularly advantageous have been found to be the "ionic liquids" (ILs). Ionic liquids are known in the art. An ionic liquid (IL) is a salt in liquid state. Ionic liquids are typically used as solvents. Ionic liquids have been shown to be particularly useful in the dissolution of cellulose. Cellulose has a highly crystalline structure with an extensive intra- and inter-molecular hydrogen bonding within the parallel chains which renders it insoluble in water. However, cellulose as well as the other saccharides have been shown to be soluble to highly soluble in ionic liquids. Hence, an ionic liquid may be used to dissolve cellulose and the saccharides in the preparation of the invention. Any ionic liquid able to dissolve cellulose and saccharides may be used according to the present invention. The IL may be chosen for its ability to dissolute carbohydrates, including cellulose, as well as for its proven ability to catalyse the dehydration of fructose to HMF. Hence, ionic liquids are the preferred solvent according to the present invention. Preferably, the ionic liquid is selected from Ethyl-3-methylimidazolium Chloride ([EMIm]Cl), 1-Butyl-3-methylimidazolium hexafluorophosphate (BMIM-$PF_6$), 1-butyl-3,5-dimethylpyridinium bromide, 1-butyl-3-methylimidazolium chloride. Preferred solvent according to the invention is [EMIm]Cl.

The preparation according to the present invention may occur in inert nitrogen atmosphere. Advantageously, it has been seen that when the preparation of HMF according to the invention is performed under inert nitrogen atmosphere, HMF side reactions are prevented. The preparation of HMF may be performed by degassing with vacuum to remove molecular oxygen and trace amount of water from the solution comprising the starting saccharide, creating and maintaining an inert nitrogen atmosphere, then adding the aryl or heteroaryl boronic acid of the invention and carrying out the preparation of HMF in an inert nitrogen atmosphere.

Hence, in an embodiment, the present invention is directed to a process for the preparation of HMF which comprises
a) providing a solution comprising a saccharide, preferably glucose or cellulose;
b) degasing the solution preferably under vacuum to remove residual oxygen and water;
c) adding $N_2$ to create an inert nitrogen atmosphere, and
d) adding the aryl-or heteroaryl-boronic acid according to the invention.

Preferably, the aryl-or heteroaryl-boronic acid are of formula (I) as disclosed above.

The preparation of HMF may occur at any temperature suitable for the conversion of the saccharide in fructose and of fructose in HMF. Temperatures suitable for the preparation of HMF according to the invention ranges from 70 to 140° C., preferably 100 to 140° C., more preferably 120-110° C. Preferably during the preparation of HMF, the temperature is kept constant.

The amount of aryl or heteroaryl catalyst according to the invention from 5% to 150% of the moles of saccharide monomer, preferably 10% to 100% of the moles of saccharide monomer, more preferably 15% to 25% of the moles of saccharide monomer, even more preferably 20% of the moles of saccharide monomer. "Saccharide monomer" is referred herein to the starting saccharide material for the preparation of HMF. For example if glucose is the starting material for the preparation of HMF, the mole percentage of the aryl or heteroaryl boronic acid catalyst will be calculated based on the mole of glucose. The amount of catalyst will be therefore 5% to 150% of the moles of glucose monomer, preferably 10% to 100% of the moles of glucose monomer, more preferably 15% to 25% of the moles of glucose monomer, even more preferably 20% of the moles of glucose monomer.

When cellulose is used a starting material, the calculation of the mole of the boronic acid of the invention is based on the mole of glucose after the polymerization of the cellulose. The calculation may be done assuming that the cellulose is completely depolymerized.

The conversion of a saccharide in HMF according to the invention may be performed in the time required for the conversion. Typically the conversion occurs in 3 to 24 h, preferably, 3 to 21 h.

The starting material for the preparation of HMF are saccharides. Saccharides according to the present invention are monosaccharides such as glucose, fructose, mannose, allose, galactose etc., disaccharides such as sucrose, oligosaccharides, and polysaccharides such as cellulose. Disaccharides, oligosaccharides, and polysaccharides need to be depolymerized to monosaccharides before their conversion to fructose. The de-polymerization step may occur in the presence of the aryl and heteroaryl boronic acid of the invention in a one pot process.

Any monosaccharide is suitable for the preparation of HMF according to the present invention. However, it has been seen that preferred monosaccharides are those forming a monosaccharide-boron complex having a Gauche-Anti conformation (Newman projection) specifically a gauche conformation for the chelating diols and an anti-conformation between the chelation and the rest of the monosaccharide. (FIG. 12)

Figure 12:
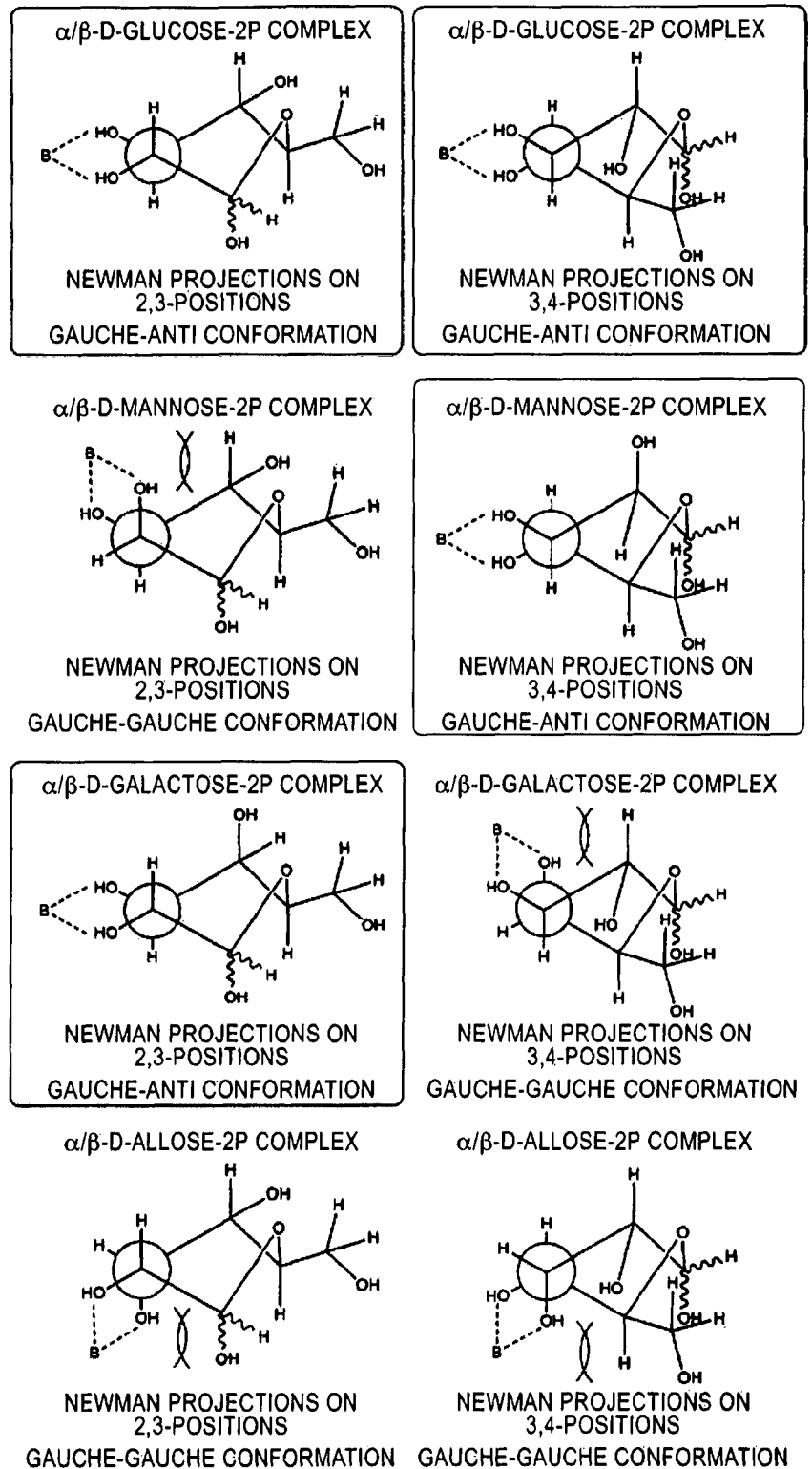
FIG. 12 illustrates the Newman projections for monosaccharide-boron complexes. Gauche-Anti conformation refers to gauche conformation for the chelating diols and conformation between the chelation and the rest of the monosaccharide ring. Steric effects with the rest of the monosaccharide ring are only present in Gauche-Gauche conformation, with the most steric being from the closest axial group. Only chelation of diols with Gauche-Anti conformation is allowed (shown by the box drawn around it). The number of vicinal trans-diol groups is equivalent to the number of Gauche-Anti conformation available in a monosaccharide chair form.

As can be seen from FIG. 12, the glucose-boron complex has gauche-anti conformations both when the complex is with boron and diols in 2,3 positions and in 3,4 positions. Mannose- and galactose-boron complex show one gauche-anti and one gauche-gauche conformations, while allose-boron complex show two gauche-gauche conformation. Glucose and cellulose are the preferred saccharides.

In a third aspect the present invention is directed to the use of aryl and heteroaryl boronic acid as defined above for the conversion of saccharides other than fructose in fructose.

Definitions

The term "aryl," as used herein, refers to a mono- or polycyclic carbocyclic ring system comprising at least one aromatic ring, including, but not limited to, phenyl, naphthyl, tetrahydronaphthyl, indanyl, idenyl. A polycyclic aryl is a polycyclic ring system that comprises at least one aromatic ring. Polycyclic aryls can comprise fused rings, covalently attached rings or a combination thereof. The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A polycyclic heteroaryl can comprise fused rings, covalently attached rings or a combination thereof.

The term "$C_1$-$C_6$ alkyl" as used herein, refer to saturated, straight- or branched-chain hydrocarbon radicals containing between one and six, or the like, respectively. Examples of $C_1$-$C_6$ alkyl radicals include, but are not limited to, methyl, ethyl, propyl, isopropyl, "-butyl, tert-butyl, neopentyl, n-hexyl, heptyl and octyl radicals.

The terms "$C_2$-$C_6$ alkenyl," as used herein, refer to straight- or branched-chain hydrocarbon radicals containing from two to six carbon atoms, or the like, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_6$ alkynyl" as used herein, refer to straight- or branched-chain hydrocarbon radicals containing from two to six carbon atoms, or the like, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

EXAMPLES

The following examples are solely provided in order to demonstrate and further illustrate certain preferred embodiments and aspects of the present invention and are by no means to be construed as limiting the scope thereof.

1. Result and Discussion

Figure 2:
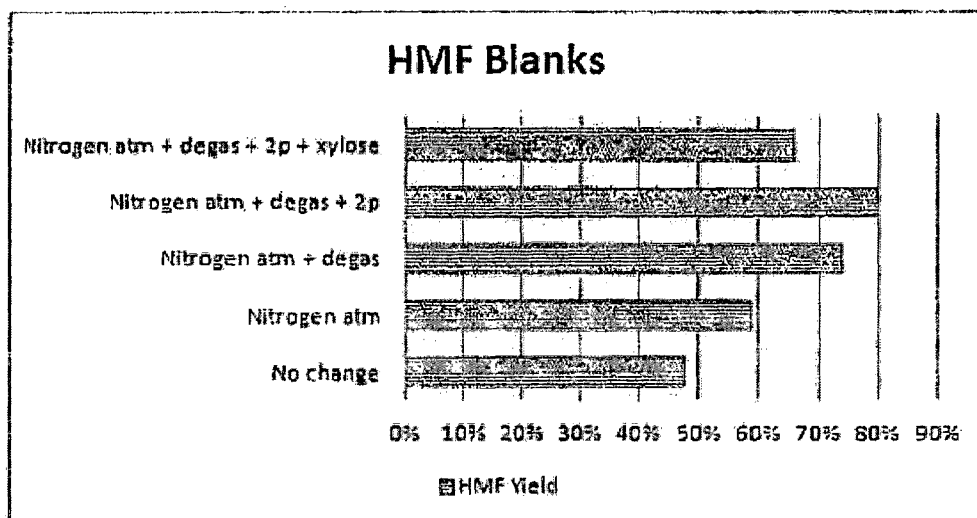
FIG. 2 shows the effects on HMF yield of changes in reaction conditions. Changes in reaction conditions were made to understand their effects on HMF during the course of heating in [EMIm]Cl at 120° C. for 3 h. Initial HMF amount used was 70 mg (0.555 mmol), except when xylose was used, in which the HMF amount was then changed to 35 mg (0.273 mmol) with xylose at 41.7 mg (0.27 Smmol) or in 1:1 molar ratio. In the case where a catalyst was used, the catalyst amount was 10 mol % with respect to the starting material, for example if glucose is the starting material the mol % is with respect to the glucose. If another saccharide monomer as starting material is used the mol % is with respect to said saccharide monomer. The yield obtained refers to isolated yield. The suspected side-products with HMF include both unimolecular and bimolecular reactions with other HMF, the ionic liquid solvent, and with monosaccharides (if present) to produce various soluble polymers, insoluble humins, as well as rehydration products levulinic acid (LA) and formic acid.

Reaction protocol optimization. One of the problems in HMF synthesis is its complexity due to the possibility of side reactions. As monosaccharide dehydration reactions produces 3 molar equivalents of water molecules, and the dehydration starting from glucose requires a high temperature, strict protocols are necessary to prevent formation of unwanted products from HMF.[25,27] To find this optimum process for HMF production, a series of blank HMF experiments have been conducted to study the effects of different conditions (FIG. 2 and Table S1). The parameters which were observed to be important in preventing HMF side-reactions included carrying out the reaction in inert nitrogen atmosphere, degassing with vacuum to remove molecular oxygen and trace amounts of water, and adding catalyst (such as 2p).

The results also showed that HMF was unstable in the presence of Xylose, a five carbon monosaccharide that cannot form HMF.

TABLE S1

HMF blanks

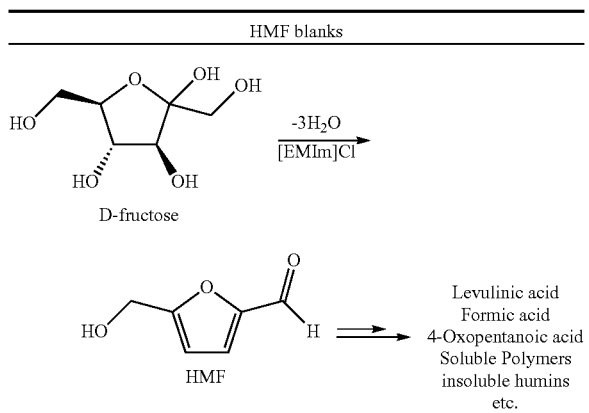

D-fructose

Levulinic acid
Formic acid
4-Oxopentanoic acid
Soluble Polymers
insoluble humins
etc.

HMF

| Entry | Reagent[1] | Temperature | Time | Catalyst[2] | Degas? (Y/N) | $N_2$ atm? (Y/N) | Yield[3] |
|---|---|---|---|---|---|---|---|
| 1 | HMF | 120° C. | 3 h | — | N | N | 48% |
| 2 | HMF | 120° C. | 3 h | — | N | Y | 59% |
| 3 | HMF | 120° C. | 3 h | — | Y | Y | 74% |
| 4 | HMF | 120° C. | 3 h | 2p | Y | Y | 80% |
| 5 | HMF + Xylose[b] | 120° C. | 3 h | 2p | Y | Y | 66% |

[1]Initial HMF amount was 70 mg (0.555 mmol) for entry I to 4. Entry 5 had HMF (35 mg, 0.278 mmol) and Xylose (41.7 mg, 0.278 mmol) in 1:1 molar ratio.
[2]Catalyst loading was 10% mol
[3]Yield obtained refers to isolated yield.
[4]Catalyst mol % used was with respect to the number of moles of glucose: 100 mol % relates to 1:1 molar ratio.

Figure 3:
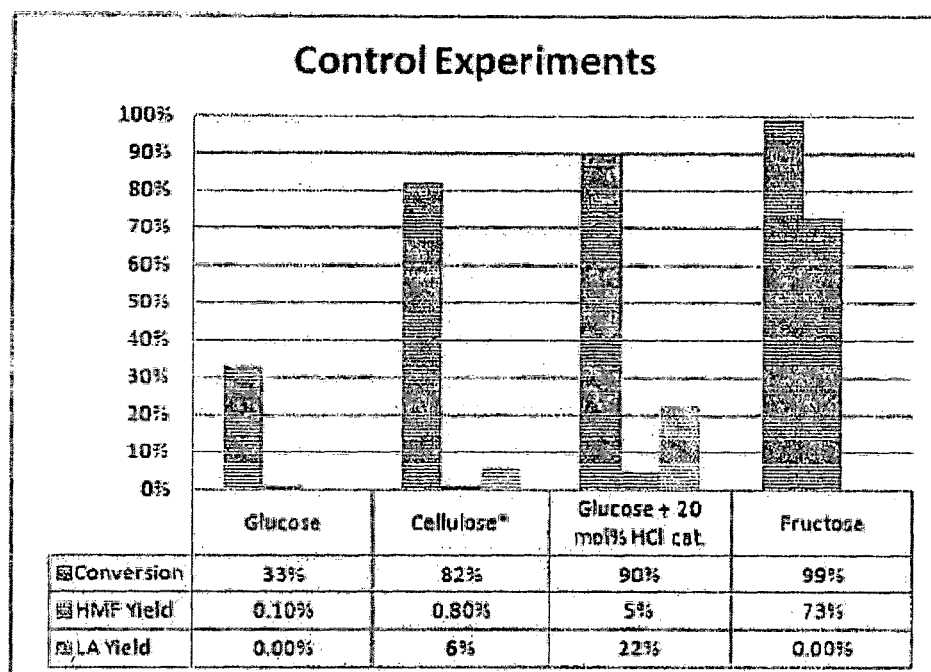
FIG. 3 illustrates the results of the Control Experiments. Catalyst mol % used was with respect to the number of moles of glucose; 100 mol % relates to 1:1 molar ratio. Levulinic acid (LA) yields were studied to observe side-reactions due to HMF rehydration. Concentrated HCl used was a 37 wt % aqueous solution. Both conversion and yield were obtained through HPLC analysis. In the case of cellulose, conversion was calculated based on the assumption that the polymer chains were fully hydrolyzed into glucose. Conditions used were [EMIm]Cl solvent, 120° C., 3 h, $N_2$ (g) with degassing.

Other blank experiments conducted included glucose, fructose and cellulose controls. A control experiment with HCl at 20 mol % was also done to identify the effects of Bronsted acid catalyst as opposed to Lewis acid (FIG. 3 and Table S2).

TABLE S2

Control experiments

D-glucose, or D-fructose, or cellulose → [No catalyst or conc. HCl, [EMIm]Cl, 120° C. 3 h, $N_2$ (g), degas] → HMF

| Entry | Reagent | Catalyst | Catalyst mol %[4] | Time | Sugar Conversion | HMF Yield | LA Yield[5] |
|---|---|---|---|---|---|---|---|
| 1 | Glucose | — | — | 3 h | 33% | 0.1% | 0.0% |
| 2 | Fructose | — | — | 3 h | 99% | 73% | 0.0% |
| 3 | Cellulose[6] | — | — | 20 h | 82% | 0.8% | 6% |
| 4 | Glucose | HCl[7] | 20 | 3 h | 90% | 5% | 22% |

[5]Levulinic acid (LA) yields were studied to observe side-reactions due to rehydration of HMF.
[6]Calculations for cellulose were made with the assumption of full hydrolysis to glucose.
[7]Concentrated HCl used was a 37 wt % aqueous solution The control experiments showed that glucose could not be converted to HMF in the reaction conditions alone without a catalyst, while fructose could achieve high HMF yields in high selectivity under the same reaction conditions. The conversion of cellulose was also studied, with similar conclusion as glucose, but with prolonged heating due to the insoluble nature and low reactivity without catalysts. Bronsted acid, HCl, was found to catalyse high conversions of glucose, but with low selectivity to HMF, as the presence of hydroxonium cation was observed to increase HMF rehydration side-reactions to levulinic acid (LA).

Figure 4:
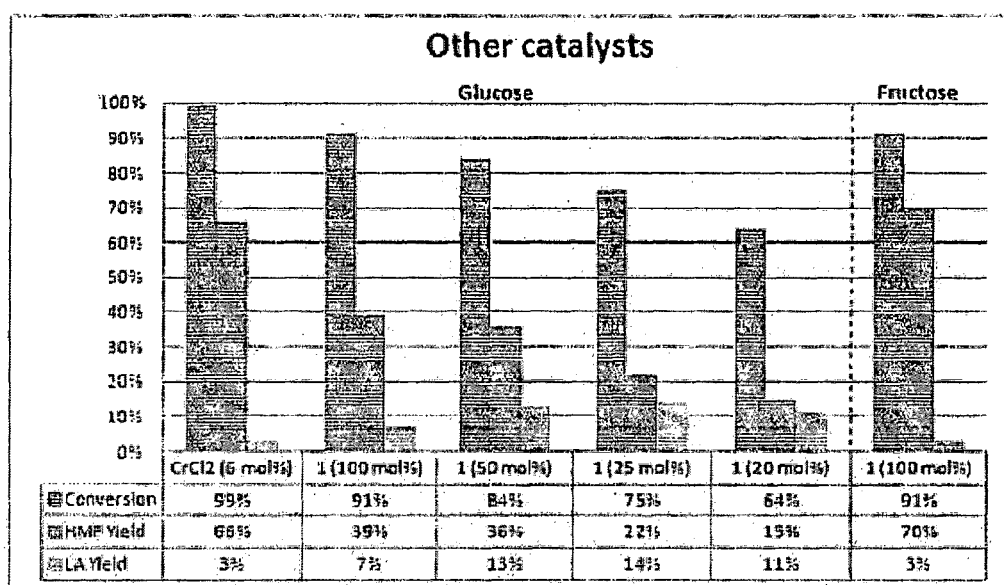
FIG. 4 shows the results of the comparison with prior art catalyst $CrCl_2$. Comparison with previous work done reported value of 68%-700% HMF yield with $CrCl_2$ catalyst at 100° C. in [EMIm]Cl tor 3 h, and of 41.5% HMF yield with $B(OH)_3$ catalyst at 120° C. in [EMIm]Cl for 3 h. Reproducibility was good.
Figure 5:
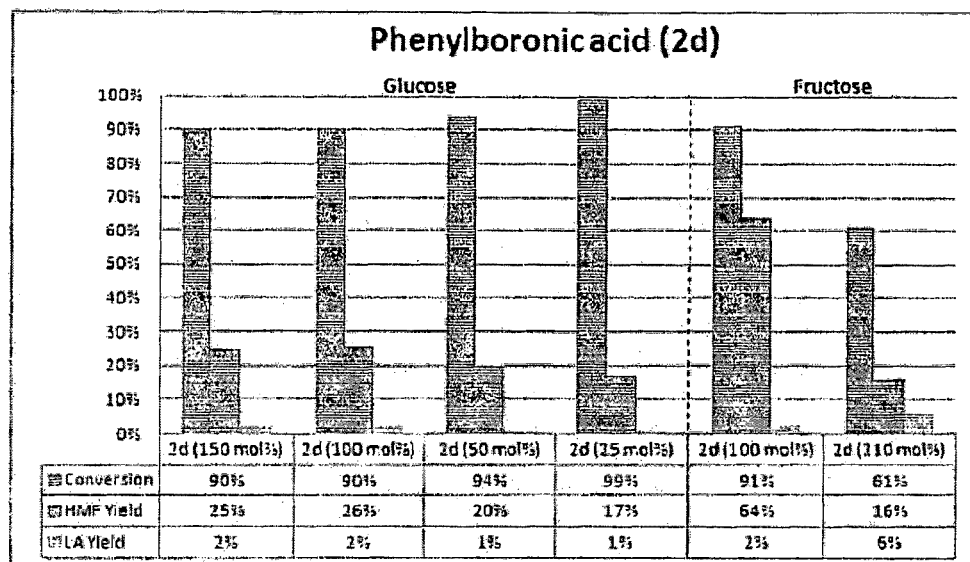
FIG. 5 illustrates the HMF yield obtained using phenylboronic acid at different % concentration. Phenylboronic acid (2d) was observed to be able to catalyse glucose conversion to HMF. Other conditions used were [EMIm]Cl solvent, 120° C., 3 h, $N_2$, (g) with degassing.

Phenylboronic Catalysed Reaction. To study the feasibility of arylboronic acid as catalysts, phenylboronic acid, 2d, was first used and the results compared with catalysts reported in previous work done by others with $CrCl_2$ and boric acid, 1 (FIG. 4). The results suggested that the current reaction conditions were able to reasonably reproduce previous work done by others on HMF production. Experiments on fructose with boric acid, 1, resulted in higher HMF yield than previous work done (~32%)[20], which could be due to the degassing procedure. In addition, 2d was observed to catalyse high conversions of glucose (FIG. 5).

TABLE S3

$PhB(OH)_2$ 2d vs Other catalysts

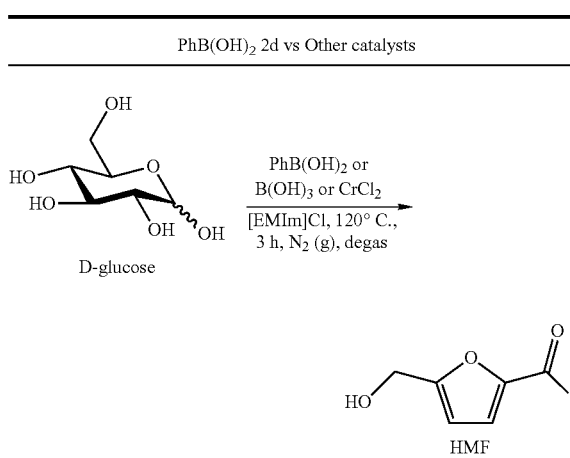

| Entry | Catalyst | Reagent | Catalyst mol % | Glucose Conversion | HMF Yield | LA Yield |
|---|---|---|---|---|---|---|
| 1 | $CrCl_2$ | Glucose | 6 | 99% | 66%[8] | 3% |
| 2 | 1 | Glucose | 100 | 91% | 39%[9] | 7% |
| 3 | 1 | Glucose | 50 | 84% | 36% | 13% |
| 4 | 1 | Glucose | 25 | 75% | 22% | 14% |
| 5 | 1 | Glucose | 20 | 64% | 15% | 11% |
| 6 | 2d | Glucose | 150 | 90% | 25% | 2% |
| 7 | 2d | Glucose | 100 | 90% | 26% | 2% |
| 8 | 2d | Glucose | 50 | 94% | 20% | 1% |
| 9 | 2d | Glucose | 25 | 99% | 17% | 1% |
| 10 | 1 | Fructose | 100 | 91% | 70% | 3% |
| 11 | 2d | Fructose | 100 | 91% | 64% | 2% |
| 12 | 2d | Fructose | 210 | 61% | 16% | 6% |

In the reaction with fructose, the presence of catalyst 2d lowered HMF production than was obtainable from the fructose blank experiment (FIG. 2).

Furthermore, increasing the amounts of catalysts was observed to inhibit HMF production, a phenomenon consistent with previous work done on boric acids, probably due to the formation of a 2,3,4,6 diphenylboronicfructose complex[20] of formula

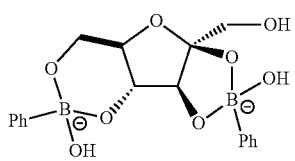

A 2,3,4,6 Diphenylborenicfructose complex

Such a complex has been shown to exist due to phenylboronic acid's strong binding constant towards fructose. The binding constants calculated by Lorand and Edwards for phenylboronic acid in water at 25° C. showed that its preference for binding in fructose (K=4 400 mo⁻¹) is much higher than for glucose (K=110 mol⁻¹).[28] While both 5-membered ring and 6-membered ring formations with cis-diols are possible for phenylboronic acids, it is known that the stability of 5-membered cyclic boronate esters is higher (Scheme 3).[29] In addition, the stability constants for complex formation was found to increase with boronic acid's acidity.[28]

Scheme 3: complex formation of phenylboronic acid with glucose

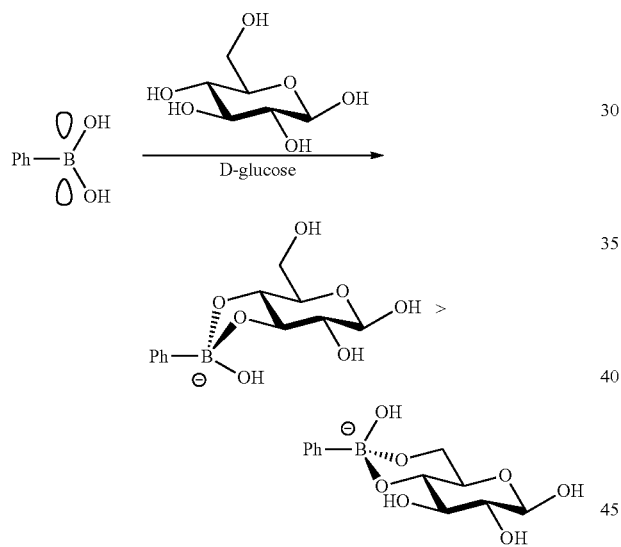

Figure 1A:
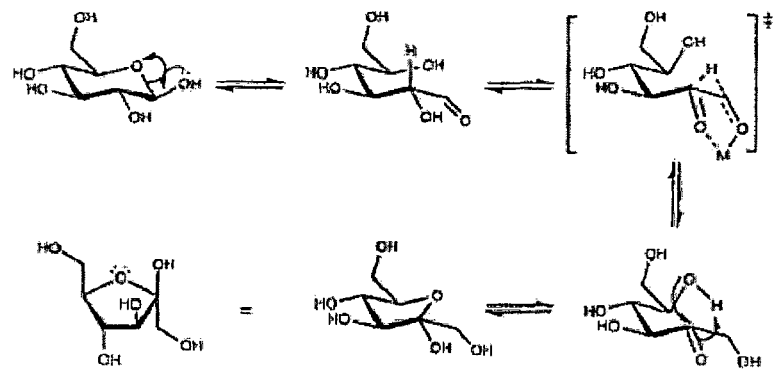
FIG. 1a shows the isomerization of glucose to fructose catalyzed by metal Lewis acid.
Figure 1B:
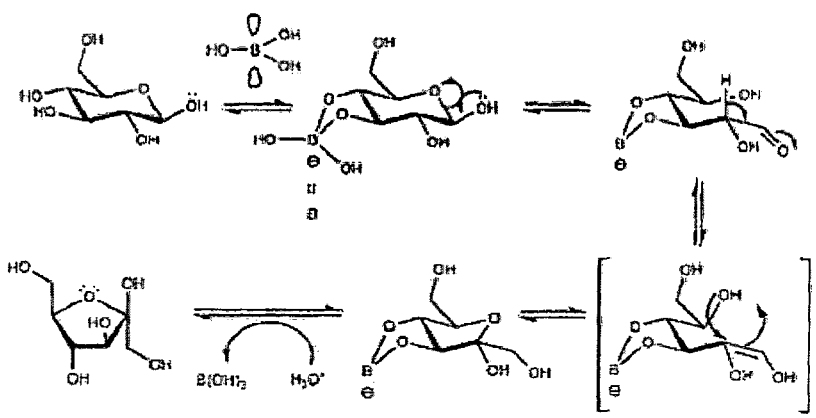
FIG. 1b shows the isomerization of glucose to fructose catalyzed by non-metal boric acid.
Figure 1C:
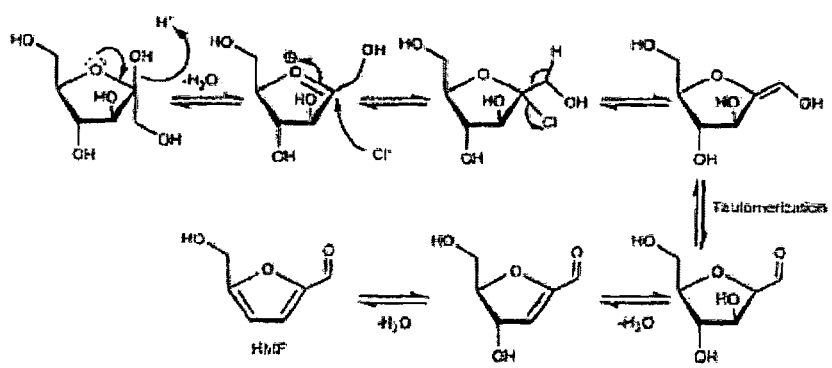
FIG. 1c shows the dehydration of glucose to fructose in acidic media.

The, present inventors have postulated that electron-withdrawing group to the phenyl(aryl/heteroaryl) ring could further increase the occurrence of the boronate ester complexes which serve to open the glucopyranose ring to its acyclic form, similar to the mechanism shown in FIG. 1b for boric acid, and thus isomerization of glucose to fructose. this rendered possible, the use of a less catalyst amount to avoid forming a stable diphenylboronicfructose complex.

Substituted Phenylboronic Acid Catalysed Reaction. In this section, a detailed study of substituent effects was done using 25 mol % of catalysts 2d to 2p indicated below

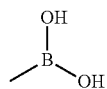

1

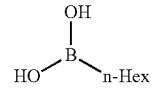

2a

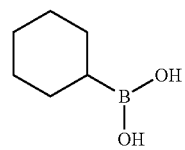

2b

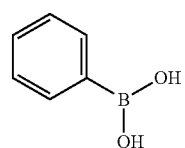

2c

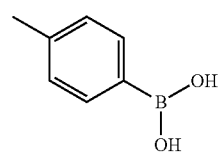

2d

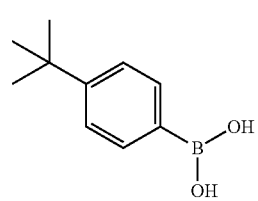

2e

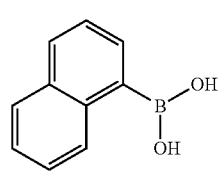

2f

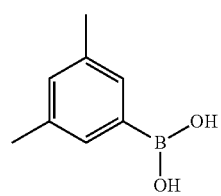

2g

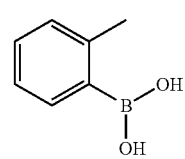

2h

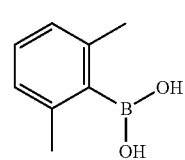

2i

2j

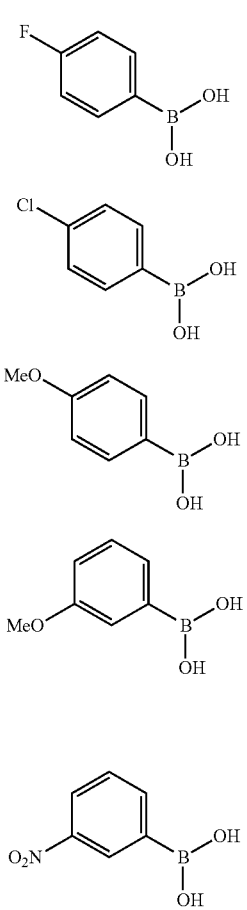

2k

2l

2m

2n

2o

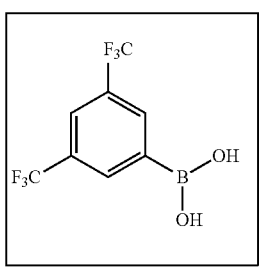

2p

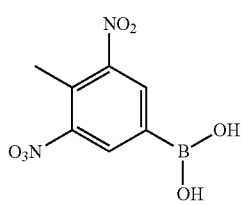

2q

Figure 6A:
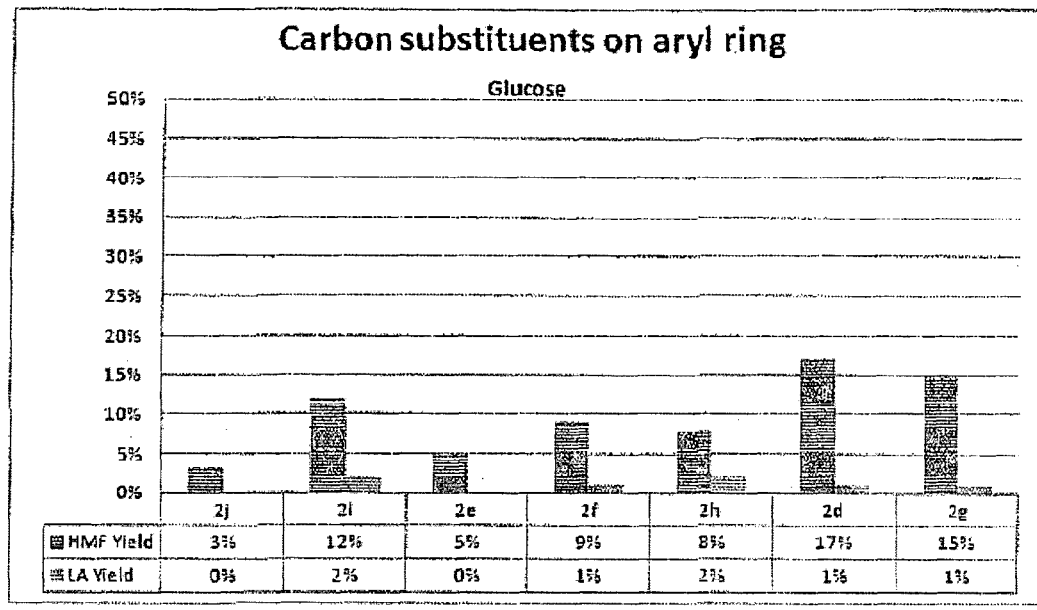
FIG. 6a: Comparison between HMF and LA yields, arranged according to decreasing pKa of boronic acid. Carbon substituents on aryl ring include methyl groups on different positions as well as t-butyl groups to study steric effects on different positions of the ring. Catalysts used were in amounts of 25 mol % with respect to glucose. Conditions used were [EMIm]Cl solvent, 120° C., 3 h, $N_3$ (g) with degassing.
Figure 6B:
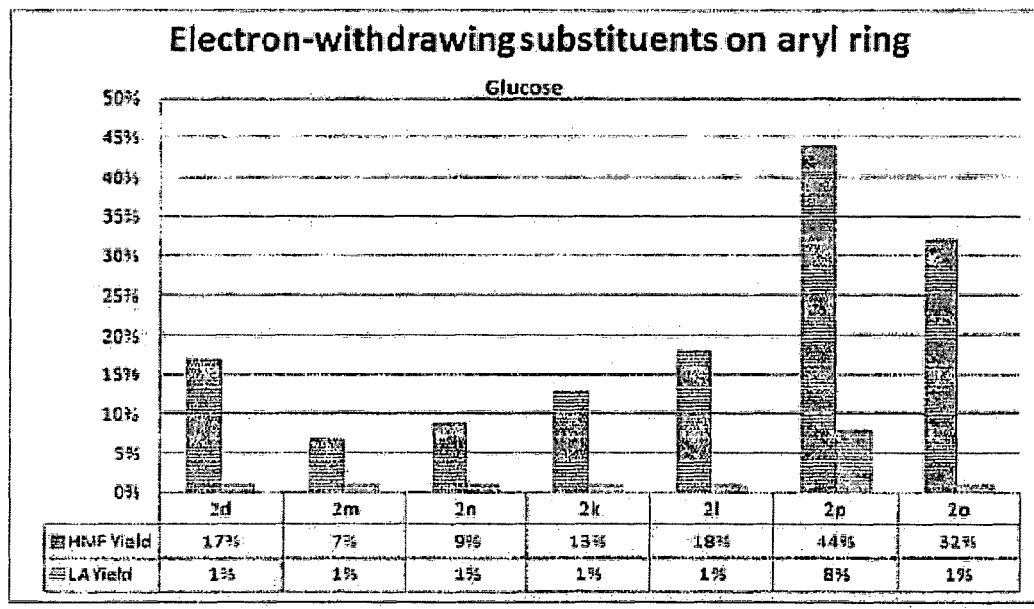
FIG. 6b: Comparison between HMF and LA yields, arranged according to decreasing pKa of boronic acid, obtained from various sources. Electron withdrawing groups lowers the pKa of arylboronic acids. Catalysts used were in amounts of 25 mol % with respect to glucose. The pKa of 2o and 2p are 7.0 and 7.2 respectively. Conditions used were [EMIm]Cl solvent, 120° t, 3 h, $N_.$ (g) with degassing.

Catalysts 2a to 2c were also used for comparison, although they do not contain phenyl rings, and were found to show little or no activity (data not shown). A series of experiments was first done to study the different catalysts. Subsequently, the best catalyst[b] was studied to find the best protocol. The result are reported in Table S4 and FIGS. 6a and 6b

TABLE S4

Reactions with various boronic acids

D-glucose →[2a-2p][[EMIm]Cl, 120° C., 3 h, $N_2$ (g), degas] HMF

| Entry | Catalyst | pKa of Catalyst | Reagent | Catalyst mol % | Time | Sugar Conversion | HMF Yield | LA Yield |
|---|---|---|---|---|---|---|---|---|
| 1 | 2a | 10.4 | Glucose | 25 | 3 h | 83% | 5% | 0% |
| 2 | 2b | 10.7 | Glucose | 25 | 3 h | 76% | 8% | 1% |
| 3 | 2c | No data | Glucose | 25 | 3 h | 97% | 12% | 2% |
| 4 | 2d | 8.9 | Glucose | 25 | 3 h | 99% | 17% | 1% |
| 5 | 2e | 9.3 | Glucose | 25 | 3 h | 90% | 5% | 0% |
| 6 | 2f | 9.3 | Glucose | 25 | 3 h | 78% | 9% | 1% |
| 7 | 2g | 8.5 | Glucose | 25 | 3 h | 92% | 15% | 1% |
| 8 | 2h | 9.1 | Glucose | 25 | 3 h | 84% | 8% | 2% |
| 9 | 2i | 9.7 | Glucose | 25 | 3 h | 90% | 12% | 2% |
| 10 | 2j | No data | Glucose | 25 | 3 h | 79% | 3% | 0% |
| 11 | 2k | 9.1 | Glucose | 25 | 3 h | 92% | 13% | 1% |
| 12 | 2l | 8.4 | Glucose | 25 | 3 h | 96% | 18% | 1% |
| 13 | 2m | 9.3 | Glucose | 25 | 3 h | 86% | 7% | 1% |
| 14 | 2n | 8.7 | Glucose | 25 | 3 h | 93% | 9% | 1% |
| 15 | 2o | 7.0 | Glucose | 25 | 3 h | 96% | 32% | 1% |
| 16 | 2p | 7.2 | Glucose | 25 | 3 h | 98% | 44% | 8% |

Taking 2d as reference, effects of aliphatic (FIG. 6a) and electron-withdrawing (FIG. 6b) substituents were studied. It was found that aliphatic substituents on the aryl ring showed low selectivity to HMF formation, while electron-withdrawing substituents were the most effective, with catalyst 2p, 3,5-bis(trifluoromethyl)phenylboronic acid, showing the highest selectivity to HMF formation with a yield of up to 50% with only 20 mol % of the catalyst. Further analysis of the data revealed some information regarding steric and electronic effects. Steric effects could be seen by studying the differences in activity between catalyst 2e and 2f which possess similar pKa (9.3). It was observed that steric effects on the para-position improved yield a little from 2e (5%) to 2f (9%). Steric effects in 2h (8%) on the meta-position also had slightly improved yields from 2e although the slightly lower pKa. (9.1) might have also helped. The steric effects on both ortho-positions 2 and 6 on the phenyl ring had a large detrimental effect to HMF yield as seen in 2j (3%) perhaps due to the bulky area around the boron centre which could have blocked approach of nucleophiles or Lewis base. A peculiar result was seen when o-tolylphenylboronic acid. 2i, was used where the pKa is high (9.7) due to the methyl group at ortho-position, but with a relatively higher HMF yield (32%) than the other methyl-substituted phenylboronic acids. These observations imply that steric bulk helped in selectivity of reaction towards HMF production, although overcrowding near the boron centre would inhibit the reaction. Electronic effects on the phenyl ring seem to have the largest effect, although increasing conjugation from phenyl in 2d to naphthalene in 2g does not increase HMF yield. Between 2k (13%) and 2l (18%) the more acidic chloro-para-substituted phenylboronic acid catalyst was observed to perform better than the fluoro-counterpart. When 2m (7%) and 2n (9%) were compared, the methoxy-para-substituted phenylboronic acid catalyst produced less HMF as compared to the meta-counterpart perhaps due to resonance contribution by 2m which lowered its Lewis acidity (Scheme 4)

Scheme 4: resonance with B-C π overlap

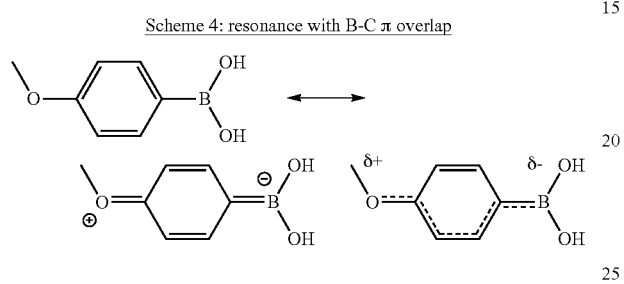

In addition, it was observed that yields significantly increased from 2n (9%) to 2o (32%) to 2p (44%), which showed that strong electron-withdrawing group substituents on the phenyl ring of phenylboronic acid were effective at increasing selectivity for glucose conversion to HMF. The results obtained with 2p were better than with 2d or 1, in terms of efficiency in yield per mole of catalyst used in the reaction.

Although the lower electron density in the aryl ring was thought to be the cause of efficient HMF production, when the optimum reaction condition was repeated with catalyst 2q, a more electron-poor arylboronic acid than 2p by virtue of two nitro groups, the yield obtained was disappointingly only 44% at 20 mol % of the catalyst (results not shown). This is also seen by comparing 2o (pKa 7.0) and 2p (pKa 7.2) in FIG. 6b, in which 2o has the better Lewis acidity but with the lower HMF yield than 2p. It was possible that other factors control the efficiency in arylboronic acid's role as catalysts.

For amounts of catalyst >50 mol %, 2 g of [EMIm]Cl solvent was used instead of just 1 g to improve solubility. It was possible that decreasing the concentration of the reactants might reduce side-reactions. To study its effects, a similar glucose dehydration experiment using 4.5 g of the IL at 10 mol % catalyst loading with respect to glucose was done, giving HMF at 38% o yield, an improvement of 2% for a 4.5 fold decrease in concentration. This meant that yield might have been marginally improved by the lower concentration, but the effects were not significant enough to affect experimental conclusions.

Figure 7:
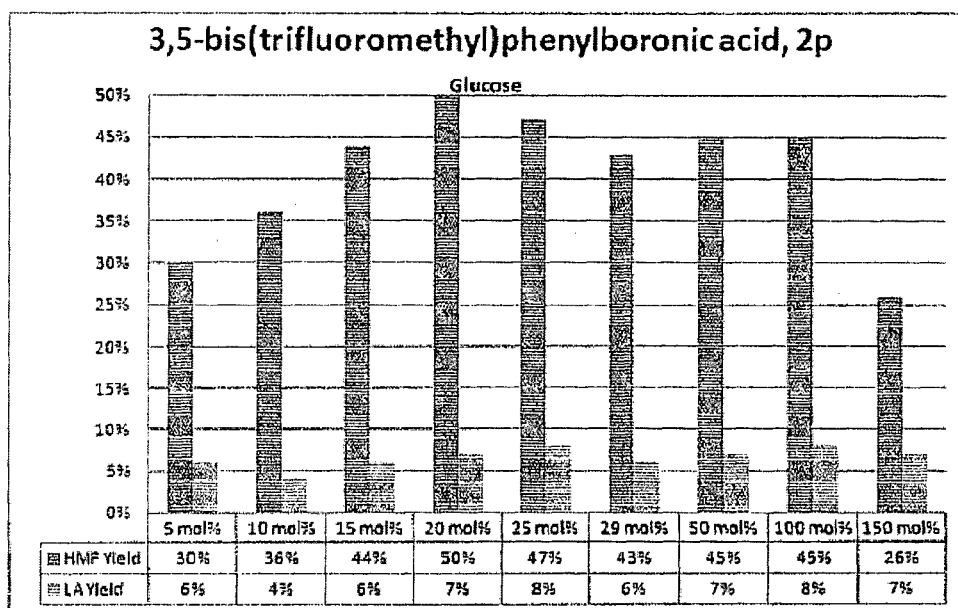
FIG. 7 shows the study of catalyst 2p at various amounts relative to glucose. The most efficient conversion was at 20 mol %. Increasing amounts of 2p further lowers yield. At 50 mol % and 100 mol %, the [EMIm]Cl solvent was increased from 1 g to 2 g to ease solubility of the catalyst. The effect of substrate dilution was studied on a separate experiment and the result was a small to negligible increase in HMF yield—Conditions used were [EMIm]Cl solvent, 120° C., 3 h, $N_2$ (g) with degassing.
Figure 8A:
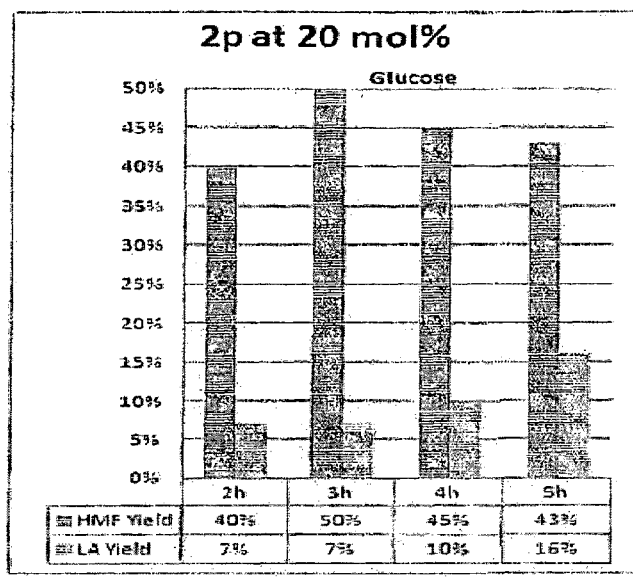
FIG. 8a relates to the study of 2p at different reaction times. Conditions used were [EMIm]Cl solvent, 120° C., $N_2$ (g) with degassing.
Figure 8B:
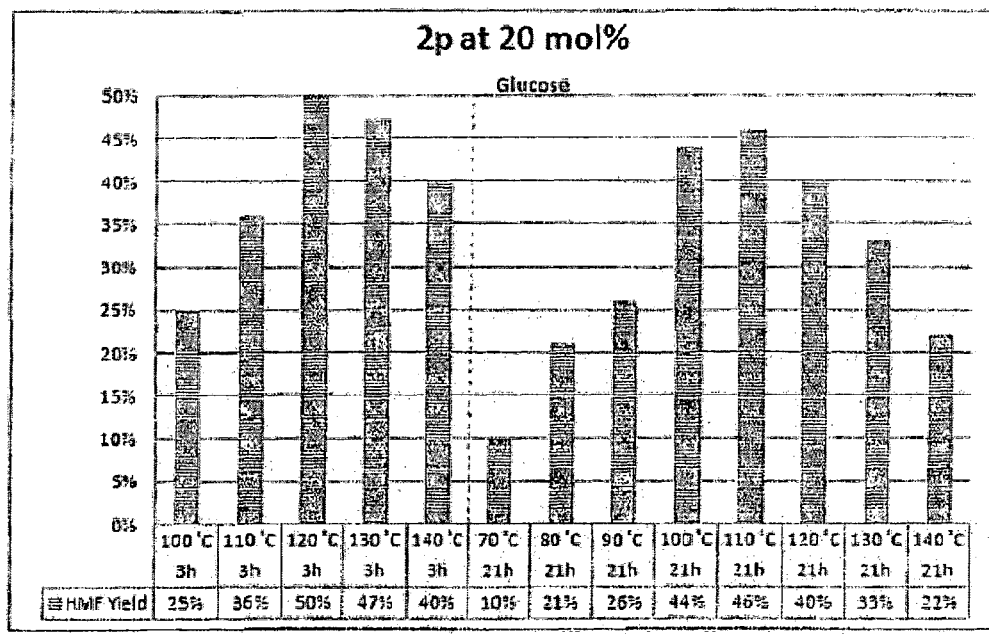
FIG. 8b: conditions used were [EMIm]Cl solvent and $N_2$ (g) with degassing, at various temperatures tor both 3 h and 21 h reaction times.

From FIGS. 7, 8a and 8b, the optimum reaction condition to achieve 50% HMF yield was reached by using 20 mol % of the catalyst 2p, and a reaction time of 3 hours at a temperature of 120° C. Longer reaction times led to increases in HMF side-reactions to LA, while increased catalyst loading inhibits HMF formation to an extent, consistent with results in FIG. 5. This result was repeated with a larger scale (50.times.) HMF production, using 5 g of Glucose instead of 0.1 g, and a similar conclusion of 50% HMF yield was obtained. The result are reported in Tables S5 (and FIGS. 7 and 8a) and Table S6 (and FIG. 8b).

TABLE S5

Reactions with 3,5-bis(trifluoromethyl)phenylboronic acid, 2p

| Entry | Catalyst | Reagent | Catalyst mol % | Time | Glucose Conversion | HMF Yield | LA Yield |
|---|---|---|---|---|---|---|---|
| 1 | 2p | Glucose | 5 | 3 h | 91% | 30% | 6% |
| 2 | 2p | Glucose | 10 | 3 h | 95% | 36% | 4% |
| 3 | 2p | Glucose | 15 | 3 h | 95% | 44% | 6% |
| 4 | 2p | Glucose | 20 | 3 h | 96% | 50%[11] | 7% |
| 5 | 2p | Glucose | 25 | 3 h | 98% | 47% | 8% |
| 6 | 2p | Glucose | 29 | 3 h | 98% | 43% | 6% |
| 7 | 2p | Glucose | 50 | 3 h | >99% | 45% | 7% |
| 8 | 2p | Glucose | 100[12] | 3 h | >99% | 45% | 8% |
| 9 | 2p | Glucose | 150[1] | 3 h | 91% | 26% | 7% |
| 10 | 2p | Glucose | 20 | 2 h | 95% | 40% | 7% |
| 11 | 2p | Glucose | 20 | 4 h | 96% | 45% | 10% |
| 12 | 2p | Glucose | 20 | | >99% | 43% | 16% |
| 13 | 2p | Fructose | 10 | 3 h | 91% | 66% | 1% |

[11]Isolated yield was 33%

To improve solubility of catalyst 2 g of [EMIm]Cl was used instead of 1 g. The effect of this was also studied.

TABLE S6

Reactions with 20 mol % 3,5-bis(trifluoromethyl)phenylboronic acid, 2p

| Entry | Catalyst | Reagent | Catalyst mol % | Time | Temperature | HMF Yield |
|---|---|---|---|---|---|---|
| 1 | 2p | Glucose | 20 | 3 h | 100° C. | 25% |
| 2 | 2p | Glucose | 20 | 3 h | 110° C. | 36% |
| 3 | 2p | Glucose | 20 | 3 h | 120° C. | 50% |
| 4 | 2p | Glucose | 20 | 3 h | 130° C. | 47% |
| 5 | 2p | Glucose | 20 | 3 h | 140° C. | 40% |
| 6 | 2p | Glucose | 20 | 21 h | 70° C. | 10% |

TABLE S6-continued

| | | | | | | |
|---|---|---|---|---|---|---|
| 7 | 2p | Glucose | 20 | 21 h | 80° C. | 21% |
| 8 | 2p | Glucose | 20 | 21 h | 90° C. | 26% |
| 9 | 2p | Glucose | 20 | 21 h | 100° C. | 44% |
| 10 | 2p | Glucose | 20 | 21 h | 110° C. | 46% |
| 11 | 2p | Glucose | 20 | 21 h | 120° C. | 40% |
| 12 | 2p | Glucose | 20 | 21 h | 130° C. | 33% |
| 13 | 2p | Glucose | 20 | 21 h | 140° C. | 22% |

However, maximum isolated HMF yield obtained was only 36% due to losses during extraction, as the distribution coefficient favours the aqueous phase. Efficient isolation methods were studied, but more needs to be done to solve this issue.[13a-31] HMF was the major product formed in the organic phase crude extract. Water insoluble compounds obtained were found to be 2p (59% of added catalyst), as confirmed by $^1$H and $^{11}$B NMR, LC-MS, and comparison with standard. Little is known about the aqueous phase, which may include water-soluble products with very low distribution coefficient in the organic phase.

From these results, it can be concluded that a stronger electron-withdrawing group on the phenyl ring ultimately improve HMF yield and reduce catalyst loading requirement for optimum results, thus improving the overall efficiency in terms of HMF yields per mol % of catalyst. One reason for this is that increasing electronegativity of boron substituents helps to delocalize the developing charges on boron, stabilizing both transition state (scheme 5) and the final anionic complex.[30a] However, this was not the only factor playing a role. Positive effects on HMF yield by steric bulk of boronic acid substituents might have also played some part, implying that some cooperation between bulk and complex stability might help in increasing the efficiency of HMF production.

Figure 9:
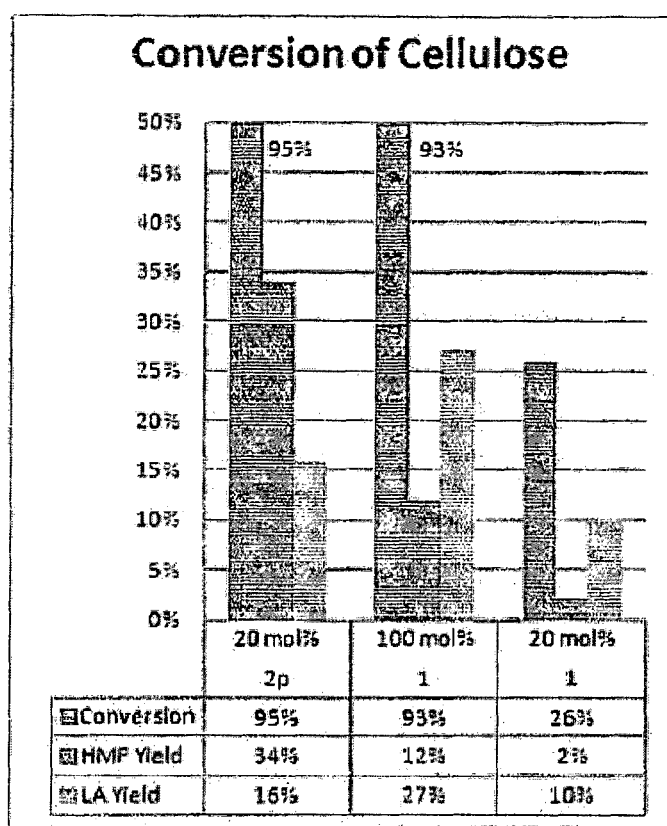
FIG. 9 shows the conversion of cellulose to HMF and the corresponding HMF yields using 2p and 1 as catalyst. Conditions used were [EMIm]Cl solvent, 120° C., 3 h, $N_2$ (g) with degassing. With cellulose, slight modification of the procedure was needed to ensure full solubility of cellulose before reaction; cellulose was added in portions over a period of time before adding the catalyst to start the reaction to produce HMF. Conversion % of cellulose was calculated with the assumption that all polymers were converted to Glucose.

2p's reactivity on cellulose was also studied using the best protocol (FIG. 9). The results showed that 2p was also able to convert cellulose to HMF, presumably through a first step depolymerisation. Comparing the results with 1, 2p's efficiency was better even when the substrate was cellulose, the result are reported in Table S7.

TABLE S7

Cellulose dehydration to HMF with 2p

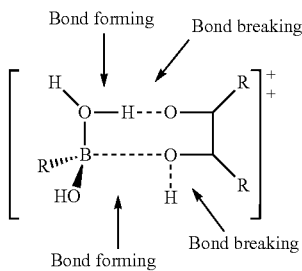

| Entry | Catalyst | Reagent | Catalyst mol % | Time | Cellulose Conversion | HMF Yield | LA Yield |
|---|---|---|---|---|---|---|---|
| 1 | 2p | Cellulose | 20 | 3 h | 95% | 34% | 16% |
| 2 | 1 | Cellulose | 100 | 3 h | 93% | 12% | 27% |
| 3 | 1 | Cellulose | 20 | 3 h | 26% | 2% | 10% |

Proposed Mechanism. A proposed mechanism by 2p is given for glucose dehydration (FIG. 10), with some considerations given through substrate studies, kinetics and thermodynamics, and NMR observations. Cellulose dehydration is thought to follow closely to that of glucose's, with an added initial depolymerisation step. In the mechanism proposed, the complexes formed are anionic, and largely similar to the mechanism proposed by Stahlberg, T. et al. for I.[20] Previous studies found that the sp$^2$ neutral boronate complexes are more acidic than the free boronic acid, making the sp$^3$ hydroxyboronate anionic complexes prevalent in the reaction.[32] Furthermore, when the boron was in its anionic tetrahedral form, the rate of boronic acid-diol complexation was significantly faster.[293, 33, 34] Kinetics also improved when pH was increased and when the ligand was in its protonated form.[33,34] These observations were explained to be due to the expulsion of the leaving group (H$_2$O) and the minimisation of charge repulsion upon complexation of sugars to the anionic tetrahedral boronate species (Scheme 5)[30a]

Scheme 5: transition state of complex formation

The mechanism is thus as such (FIG. 10): 2p first complexes with glucose to form 3, believed to be thermodynamically more stable than 4, with the loss of one equivalent of hydroxonium ion. 3 proceeded to open the glucopyranose ring to its acyclic form, 5. The reaction continued via the enediol intermediate, 6, to produce the fructofuranose cyclic boronate ester 7. Due to the strained trans-2,3-boronate ester conformation, the boronic species was released in the presence of acid to produce the fructose molecule. From here, fructose should proceed to form HMF via dehydration, releasing 3 equivalents of water and 1 equivalent of HCl. Possible formations of mono-boronate ester complex 8 and the more stable di-boronate ester complex 9 were also considered to happen, thus inhibiting the reaction upon addition of excess boronic acid catalysts. Species 10 was thought to exist, and the chloride anion was the nucleophile in this step as suggested by Stahlberg et al.[20] However, the chloride ion could have also been a base as suggested by Binder and Raines[35].

Figure 11:
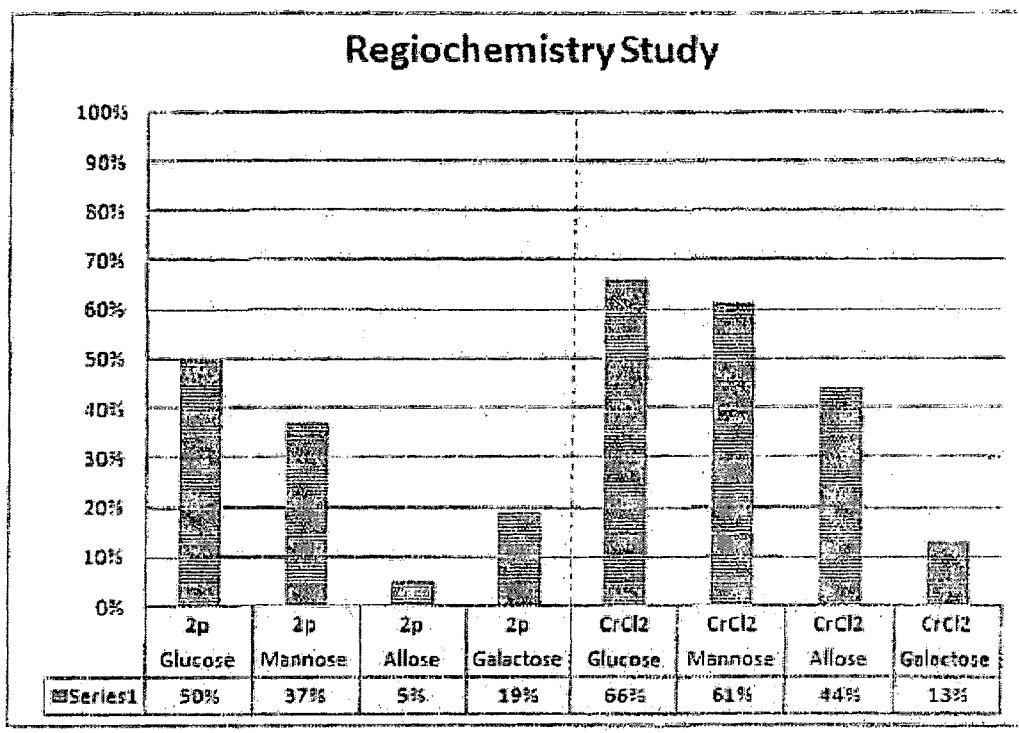
FIG. 11 shows the result of the study of the effects of hydroxyl group regiochemistry using different epimers of Glucose. HMF formation is considered to remain "high" when the yield is > or = to 30%. Amount of 2p used was 20 mol % and of $CrCl_2$ was 6 mol %. For both catalysts, the conditions used were [EMIm]Cl solvent, 120° C., 3 h, $N_2$ (g) with degassing.

Regiochemistry study. Regiochemistry of each hydroxyl group and the driving force of the formation of 5, the different epimers of glucose have been studied. Similar studies on epimers using CrCl$_2$ were done by Binder, J. B. et al. with D-mannose, D-galactose, as well as other ketoses.[36] However, in this study, only D-mannose (C-2 epimer of D-glucose) and D-galactose (C-4 epimer of D-glucose) were studied, with the addition of D-Allose (C-3 epimer of D-glucose) which was not previously done. The results are shown in FIG. 11 and in Table S8.

TABLE S8

Reactions with 20 mol % 2p and Glucose Epimers

| Entry | Catalyst | Reagent | Catalyst mol % | Time | Temperature | HMF Yield |
|---|---|---|---|---|---|---|
| 1 | 2p | Glucose | 20 | 3 h | 120° C. | 50% |
| 2 | 2p | Mannose | 20 | 3 h | 120° C. | 37% |
| 3 | 2p | Allose | 20 | 3 h | 120° C. | 5% |
| 4 | 2p | Galactose | 20 | 3 h | 120° C. | 19% |
| 5 | $CrCl_2$ | Glucose | 20 | 3 h | 120° C. | 66% |
| 6 | $CrCl_2$ | Mannose | 20 | 3 h | 120° C. | 61% |
| 7 | $CrCl_2$ | Allose | 20 | 3 h | 120° C. | 44% |
| 8 | $CrCl_2$ | Galactose | 20 | 3 h | 120° C. | 13% |

The results in FIG. 11 and Table S8 suggested that regiochemistry played an important role in HMF formation under the same condition. It was also observed that the effects differed between arylboronic acid 2p and $CrCl_2$.

While HMF formation by 2p remains high (> or = to 30%) for both glucose and mannose substrates, it was significantly inhibited in both allose and galactose, with allose being the worst. For CrCl2, the significant inhibition effect seemed to show only in galactose but not in allose. The differences between the effects could be due to a different mechanism employed by the two catalysts. Upon further analysis using the following Newman projections (FIG. 12), some clues to the mechanism could be found.

The analysis done from using the results in FIG. 11 is shown in FIG. 12, and it is believed that chelation by 2p is only possible in the Gauche-Anti conformation, as summarized in Table 1. In the following explanation, HMF yields are shown in parenthesis.

From the Newman projections (FIG. 12), D-mannose showed much less suppression of HMF formation by 2p than D-galactose or D-allose, perhaps due to the presence of the less sterically hindered 3,4-positions, whereas D-allose had these positions sterically hindered. The effect on D-galactose will be elaborated later. In addition, when compared to D-glucose, the reduction in HMF yield for 2p in D-mannose could be the result of the steric hindrance of the 2,3-positions, which might have reduced the number of pathways available for D-mannose's isomerisation to D-fructose. This could mean that chelation by the hydroxyl groups on the 2,3-positions was also important in the enediol mechanism by 2p. Results with $CrCl_2$ showed a reduction in HMF yield for both D-mannose and D-allose, but the effects are much more for D-allose. Observations in this study implied that there could be a possibility of dependence on other chelating locations on the aldoses. However, steric effects alone are insufficient to explain as $CrCl_2$ is small and could navigate around relatively easier than 2p.

The significant reduction of yield in D-allose for 2p (5%) could be due to the blockage of both 3,4- and 2,3-positions, leaving the only available route at the 1,2-positions in the case of β-D-allose. Thus, the gauche-anti conformation requirement for the enediol mechanism to be allowed is not achievable in this case. (see Table 1)

TABLE 1

Summary of region-chemistry study

| For vicinal diols at 2,3- and 3,4-positions | 2p, enediol mechanism |
|---|---|
| Gauche-Anti conformation | Allowed |
| Gauche-Gauche conformation | Disallowed |
| Anti-Gauche conformation | — |

When the study was done using D-galactose, more information could be extracted. While the enediol pathway via 3,4-position was disallowed for 2p, the pathway via 2,3-position could still allow 2p to catalyse the formation of HMF (19%). However, since the reaction pathway to HMF had to go through the ketose form of D-galactose, which is D-tagatose, the final dehydration step is suppressed significantly due to D-tagatose's low furanose propensity. Previously studied by Binder. L B. et al, D-tagatose, when compared with other ketoses, preferentially forms pyranose tautomers in both water and organic solvents (76% α-pyranose, 17% β-pyranose, 4% α-furanose and 3% β-furanose). This preference for the pyranose form inhibits formation of HMF through dehydration and its effect is seen when both 2p (19%) and $CrCl_2$ (13%) were used; $CrCl_2$ should still catalyse high conversions to HMF, unless when the ketose intermediate is in the pyranose form.

D-glucose showed the highest HMF yield for both catalysts as both 3,4-positions and 2,3-positions are less affected by steric conditions, and both pathways allowed the enediol mechanism to proceed. Considering the thermodynamics and kinetics, it is possible that D-glucose conversion to HMF by $CrCl_2$ is highest due to the presence of two vicinal trans-diois on the monosaccharide. To understand this, reference to a study done by Sugihara, J. M. et al. could be made.[37] Their study on both trans- and cis-1,2-cyciohexandiol with phenylboronic acid 2d showed that coordination to the chelating cis-diol was much easier than the trans-diol as the cis-diol has a lower initial energy barrier required to twist the chair conformation into one that resembles the boat conformation, such that the co-planar requirement for chelation with 2d is achieved. On the other hand, the trans-diol, although seemingly more achievable, requires a larger initial energy barrier to overcome as coordination requires the distortion and strain of the whole ring (scheme 6).

Scheme 6: chelation of cis and trans 1,2 cyclohexadiol with phenyl boronic acid, where R is Ph

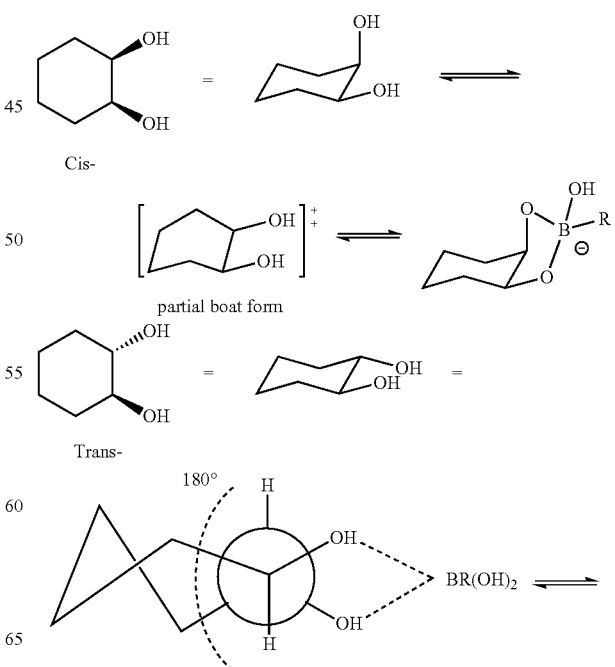

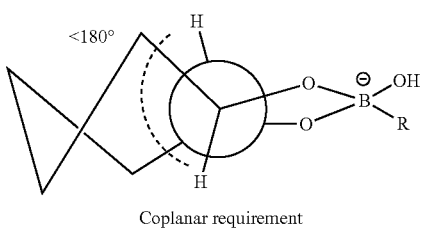

Coplanar requirement

D-glucose has its vicinal hydroxyl groups at 3,4-positions and 2,3-positions trans- to each other on the pyranose ring. This conformation allows the arylboronic acids to induce strain in the ring to facilitate ring-opening to species 5, the first step to isomerisation to the ketose form, of which the second step is the formation of the ene-diol 6, and the third the closing of the ring to form fructofuranose complex 7 (FIG. 1b).The rest of the monosaccharides also exhibit this requirement in FIG. 12as the Gauche-Anti conformations in the Newman projections all showed trans-dispositions in the chelating hydroxyl groups. In fact, the only way to have Gauche-Anti conformations is when the vicinal hydroxyl groups are trans- to each other. This effect might also explain the results of the reactions catalysed by $CrCl_2$, in which case the mechanism under consideration is the 1,2-hydride shift in the 1,2-positions, but that the presence of less vicinal trans-diol pairs had had some suppression on HMF yield. This was also shown in FIGS. 12 and Table 1, where D-mannose and D-alfose could still be converted to HMF by $CrCl_2$, but with lesser yields, and with D-allose giving the lesser amount of HMF; D-mannose had only one vicinal trans-diol while D-allose had none. Recently, in a molecular study done using NMR, Khokhlova, E. A. et al. had also established the presence of the 5-membered cyclic borate ester of boric acid, 1, and a-D-glucose, with chelation at the 1,2-positions of a-D-glucose as the resting state even though the site was sterically hindered (Gauche-Gauche conformation, not shown). Furthermore, conversion to HMF from this resting state was found to be slow. From the results obtained thus far, it is reasonable to think that the presence of such a resting state was allowed in the case of 1 due to its significantly smaller size, but at the same time, it is also the reason for the lower selectivity observed for the conversion to HMF as the resting state is inert. Possibly, it could also be the reason for the requirement for 100 mol % of 1 to convert D-glucose to HMF to achieve the desired efficiency as the presence of an extra chelation site which is inert competitively inhibits the reaction. On the other hand, the much lower 20 mol % of the catalyst 2p needed to achieve the desired efficiency could be due to the presence of the bulky aryl group in 2p that prevents chelation at vicinal diol sites that have the Gauche-Gauche conformation, which in turn might also be the reason for the higher selectivity of the conversion of D-glucose to HMF Primary alcohol effect. To answer the question whether other hydroxyl groups on D-glucose aided the reaction to produce HMF and the role of primary alcohol on C-6, the following substrate additive study was done using different alcohols (FIG. 13 and Table S9), followed by another study using glucose with its 1° alcohol protected, 11, and with the 1° alcohol completely removed, 12.

TABLE S9

Reactions with 20 mol % 2p and Diol Additives

| Entry | Catalyst | Reagent | Additive | Additive Amount | Time | Temperature | HMF Yield |
|---|---|---|---|---|---|---|---|
| 1 | 2p | Glucose | Methanol* | 500 mol % | 3 h | 120° C. | 20% |
| 2 | 2p | Glucose | 1,2-dipropanol | 50 mol % | 3 h | 120° C. | 10% |
| 3 | 2p | Glucose | 1,3-dipropanol | 50 mol % | 3 h | 120° C. | 4% |
| 4 | 2p | Glucose | 1,4-dibutanol | 50 mol % | 3 h | 120° C. | 31% |
| 5 | 2p | Glucose | 1,7-dibutanol | 50 mol % | 3 h | 120° C. | 34% |

*Methanol was added in excess due to its low boiling point.

Figure 13:
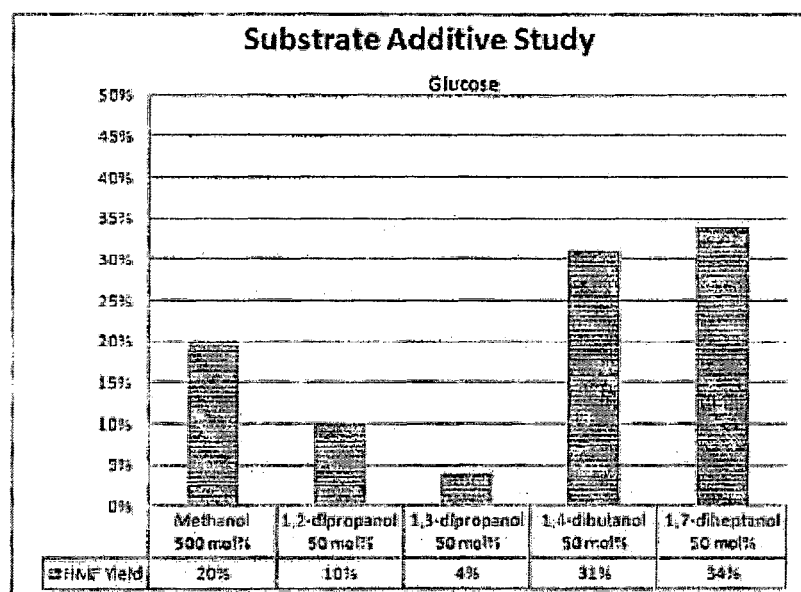
FIG. 13 shows the results of studies concerning the effect of primary alcohol as additive in the preparation of HMF. Conditions are [EMIm]Cl solvent, D-glucose, additives as stated above, 20 mol % of 2p, at 120° C. for 3 h, and $N_2$ (g) with degassing. Methanol additive was used for comparison and was added in excess due to its low boiling point.

The results in FIG. 13 and Table S9 show that the additive 1,3-dipropanol had the largest effect in suppressing HMF formation, followed by the 1,2-dipropanol. Competitive inhibition caused by the diol was the result of the formation of a stable 6-membered and 5-membered boronate ester ring. The similar results with lower suppression obtained with 1,4-dibutanol and 1,7-heptanol as additives meant that the less stable 7-membered and 10-membered boronate ester ring were not formed. Although the 6-membered ring could be thought to be the more stable form, a previous study done by Matteson, D. S. et al. on 1,2,3-propanetriol found that the boronate ester bound preferentially on the 1,2-diol unit instead.[38] Kinetic studies revealed that the forward and reverse rate constants were different for both 5-membered and 6-membered boronate ester rings, and that the lower stability constants of the 6-membered boronic esters compared to the 5-membered ones was the result of a faster reverse reaction for the former.

Thus, the 1,3-diol on the 4,6-positions on D-glucose could have played an important role in the mechanism. To find this out, the primary alcohol was first blocked using tert-butylchlorodiphenylsilane (TBDPSCl) to produce 11 (scheme 7) and then further reacted via the same reaction conditions to produce 13 (10%). The yield for 13 was much lower than anticipated if the 1,3-diol formation had served to induce competitive inhibition. Instead, the 1,3-diol might have had a cooperative assistance in the formation of the 5-membered boronate ester ring with the 1,2-diol on the 3,4-positions on D-glucose. This assistance could be in die form of an intramolecular tether, which is not unusual as arylboronic acids have been employed as one in Diels-Alder reactions that possess alcohol groups.[22a] To understand this further, the reaction was repeated with 6-deoxy-D-glucose, 12, to produce 5-methylfurfural, 14 (15%). Again, the yield was much lower than it should be if the formation of species 4 was in fact competitively inhibiting the reaction. Thus, it was possible that the 1' alcohol on D-glucose was cooperatively assisting the conversion of D-glucose to HMF (scheme 8)

Scheme 7: 6-0-TBDP5-protected D-glucose 11) was synthesized; 6-deoxy-D-glucose (12) was used as purchased; TBDPS-O protected HMF (13) and 5-methylfurfurol (1) were both obtained from dehydration of 11 and 12, respectively.

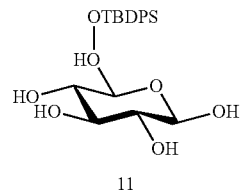

11

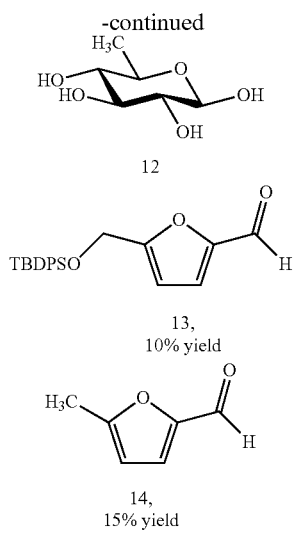

12

13,
10% yield 14,
15% yield

Scheme 8: Catalyst 2p might have used the 1° alcohol group as an intramolecular tether to reposition into the 5-membered cyclic boronate ester complexes required for ring strain and ring opening.

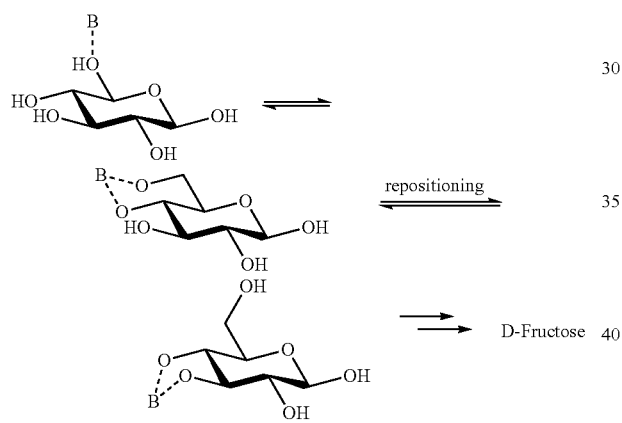

Figure 14:
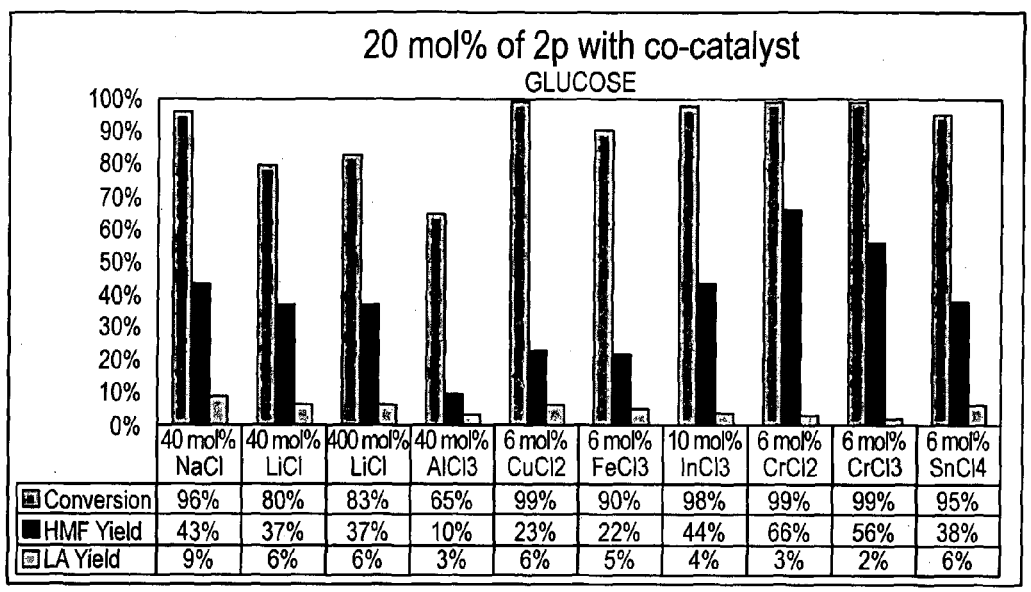
FIG. 14 shows the result of formation of HMF in the presence of a co-catalyst. Conditions are [EMIm]Cl solvent, D-glucose, 20 mol % of 2p, co-catalysts, at 120° C. for 3 h, and $N_2$ (g) with degassing. Alkali metals were added at higher amounts than transition metal catalysts.
Figure 15:
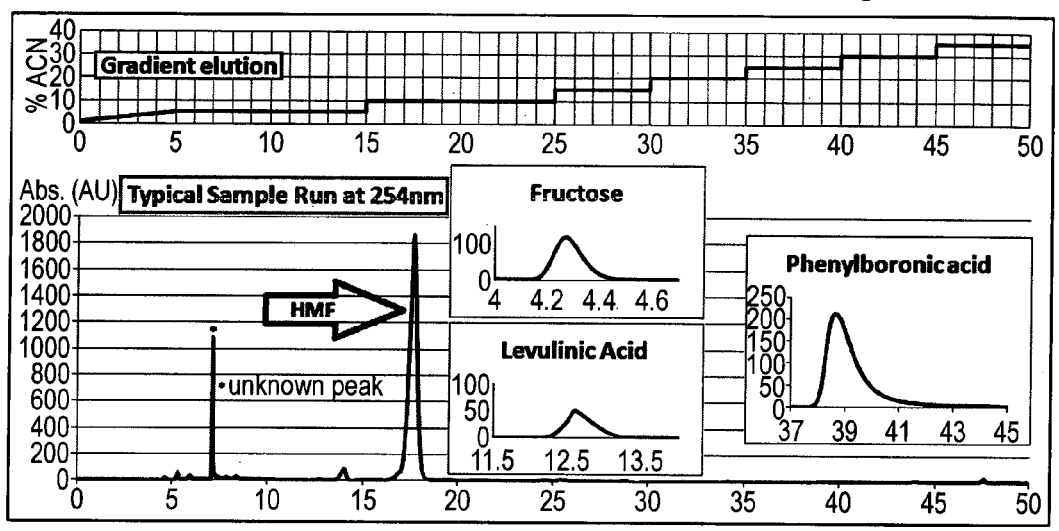
FIG. 15 shows the gradient elution versus time graph and elution order. Yield and conversion calculations are shown on top
Figure 16:
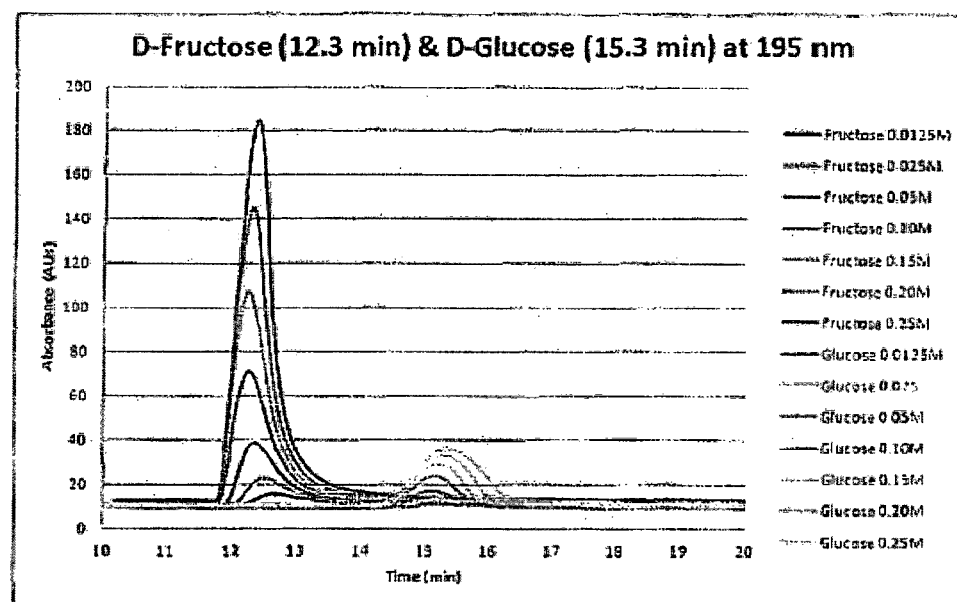
FIG. 16 shows the absorbance vs time graphs of fructose and glucose standard solutions in normal-phase carbohydrate column (ZORBAX). Eluent was 95% ACN for 0-5 min and 93.5% ACN for 5.01-30 min.
Figure 17:
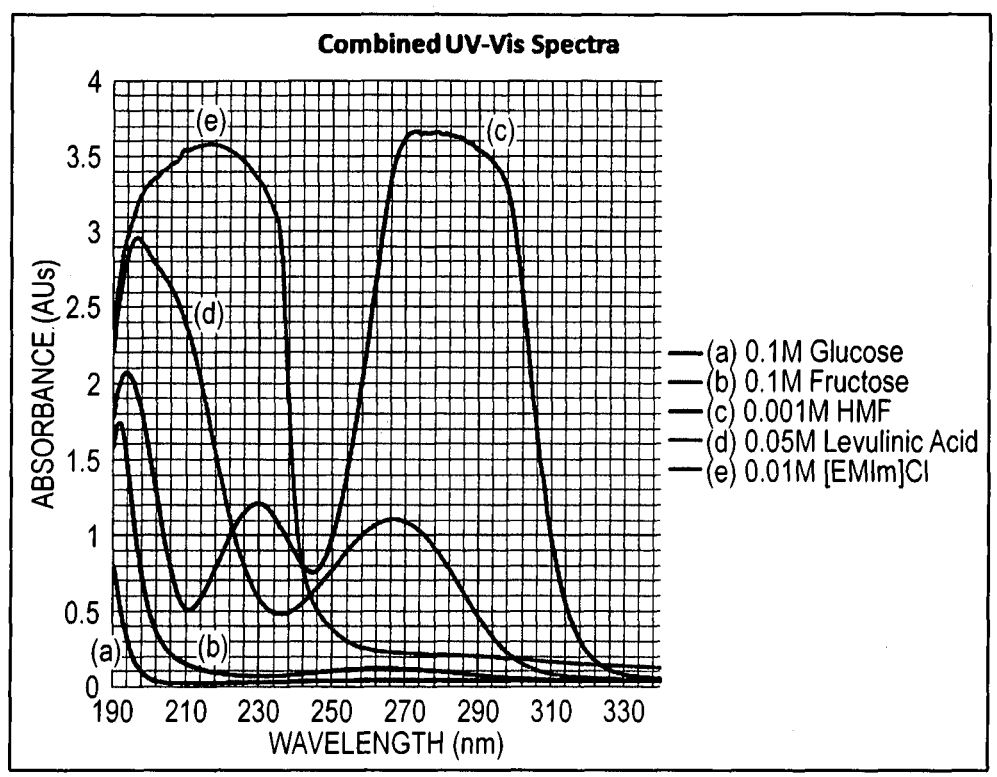
FIG. 17 shows the combined UV-vis spectra for glucose, Fructose, HMF, Levulinic acid and [EMIm]Cl.
Figure 18:
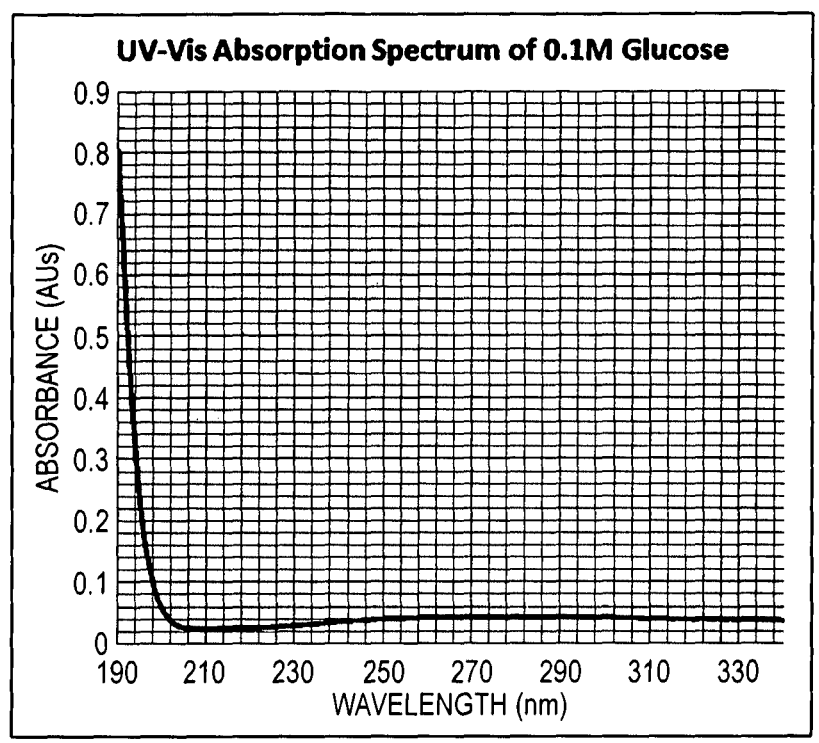
FIG. 18 shows the UV-vis absorption spectrum of glucose 0.1 M.
Figure 19:
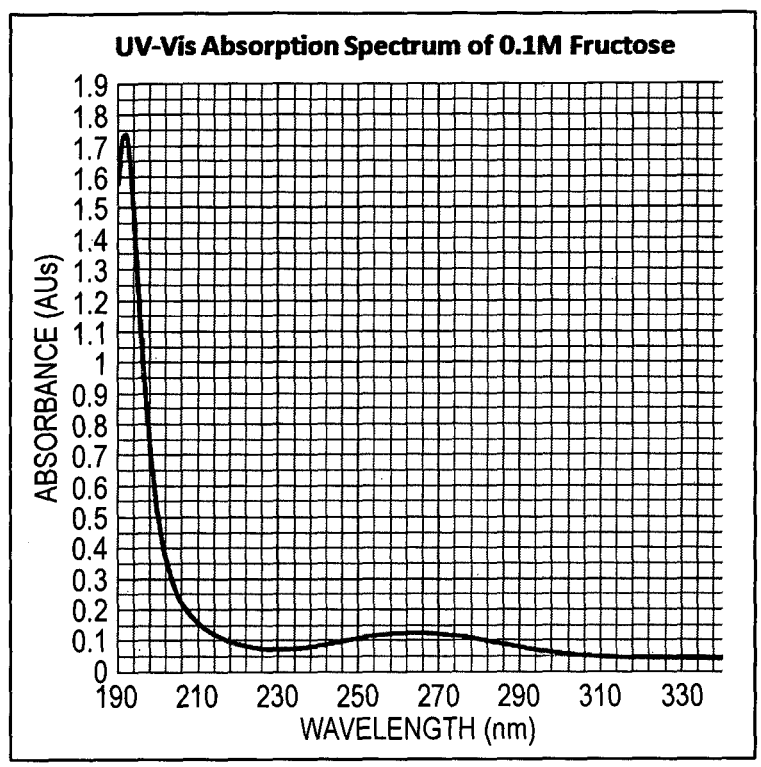
FIG. 19 shows the UV-vis absorption spectrum of fructose 0.1 M.
Figure 20:
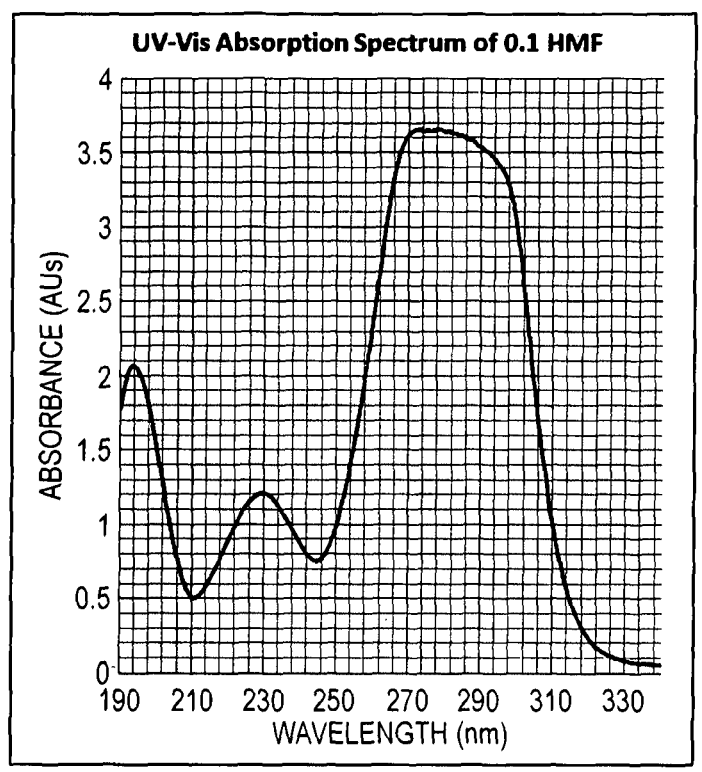
FIG. 20 shows the UV-vis absorption spectrum of HMF 0.1 M.
Figure 21A:
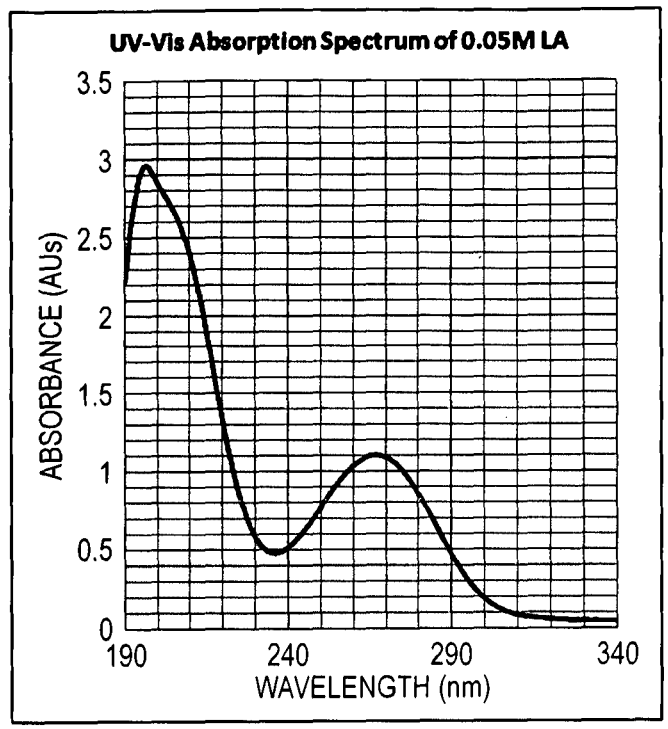
FIG. 21 shows the UV-vis absorption spectrum of LA 0.05 M (FIG. 21-a) and of [EMIm]Cl (FIG. 21b).
Figure 21B:
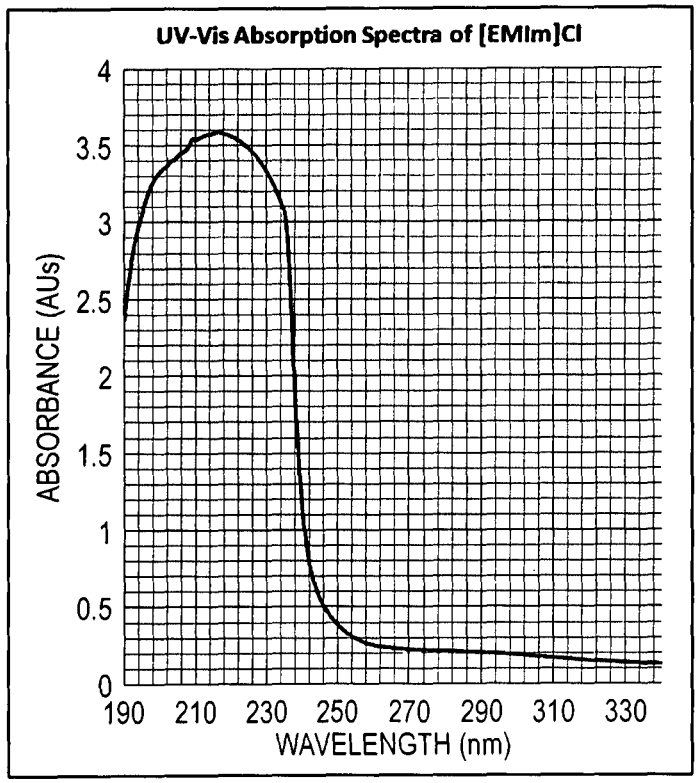
Figure 22A:
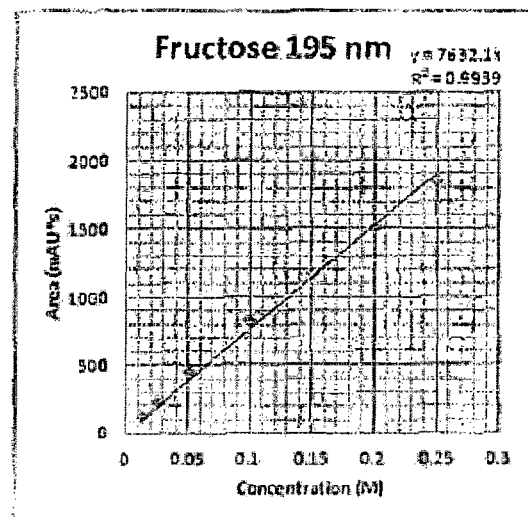
FIG. 22 shows the fructose external standard calibration curve at 195 nm (FIG. 22a) and at 210 (FIG. 22b).
Figure 22B:
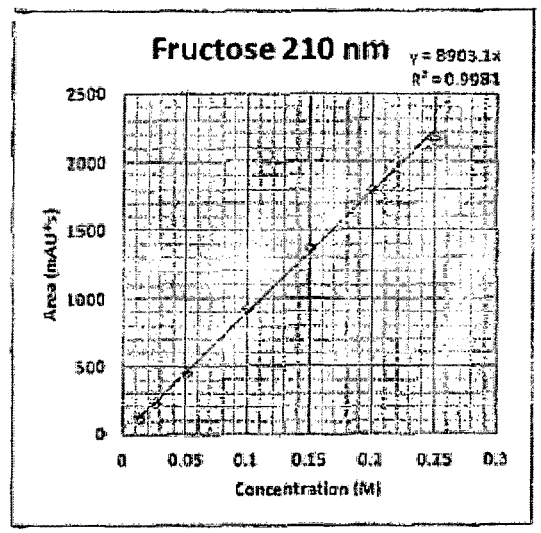
Figure 23A:
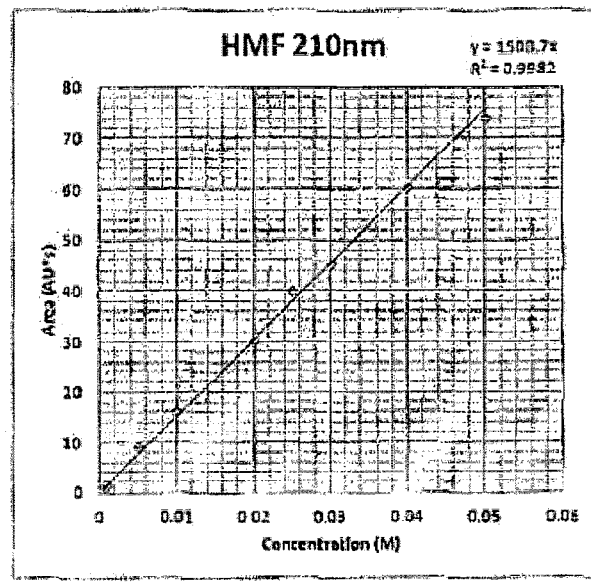
FIG. 23 shows the HMF external standard calibration curve at 195 nm (FIG. 23a) and at 210 (FIG. 23b).
Figure 23B:
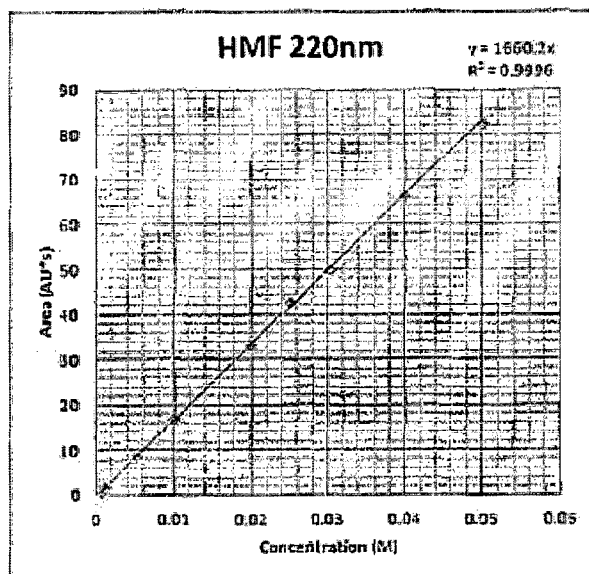
Figure 24A:
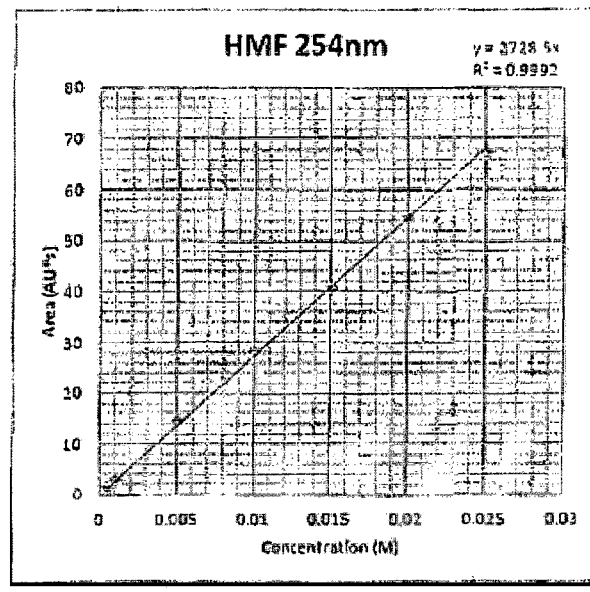
FIG. 24 shows the HMF external standard calibration curve at 254 nm (FIG. 24a) and at 284 (FIG. 24b).
Figure 24B:
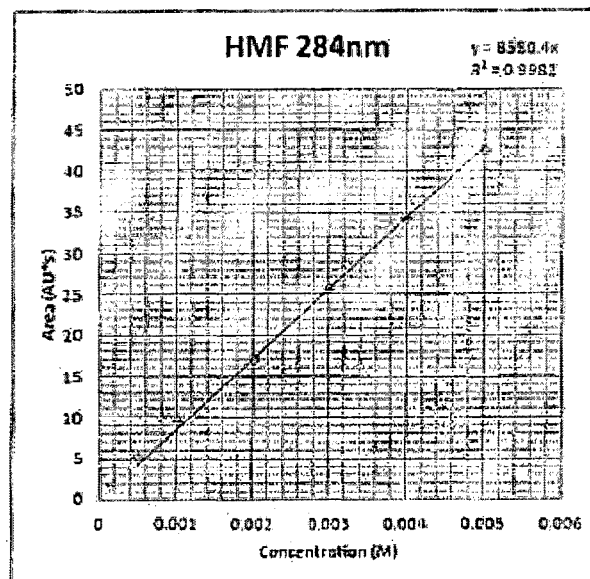
Figure 25A:
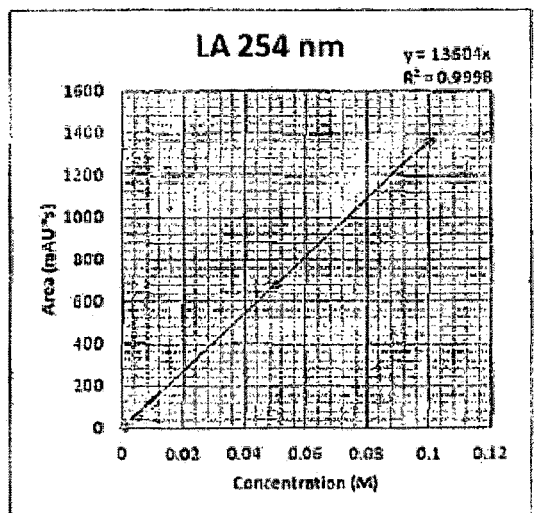
FIG. 25 shows the LA external standard calibration curve at 254 nm (FIG. 25a) and at 284 (FIG. 25b).
Figure 25B:
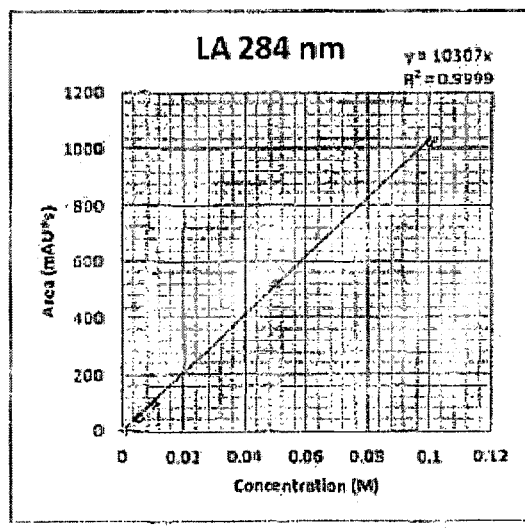
Figure 26:
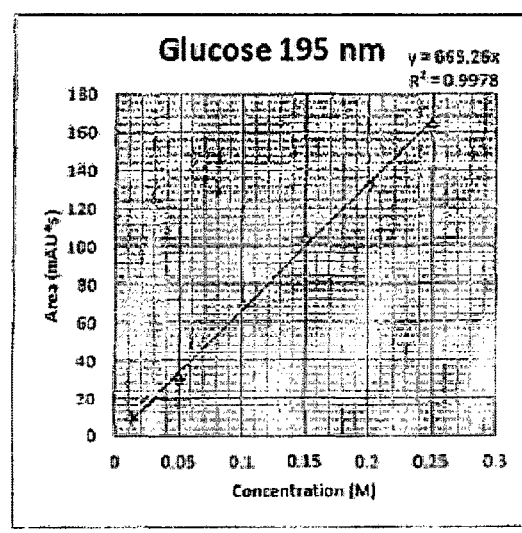
FIG. 26 shows the glucose external standard calibration curve at 195 nm.
Figure 27:
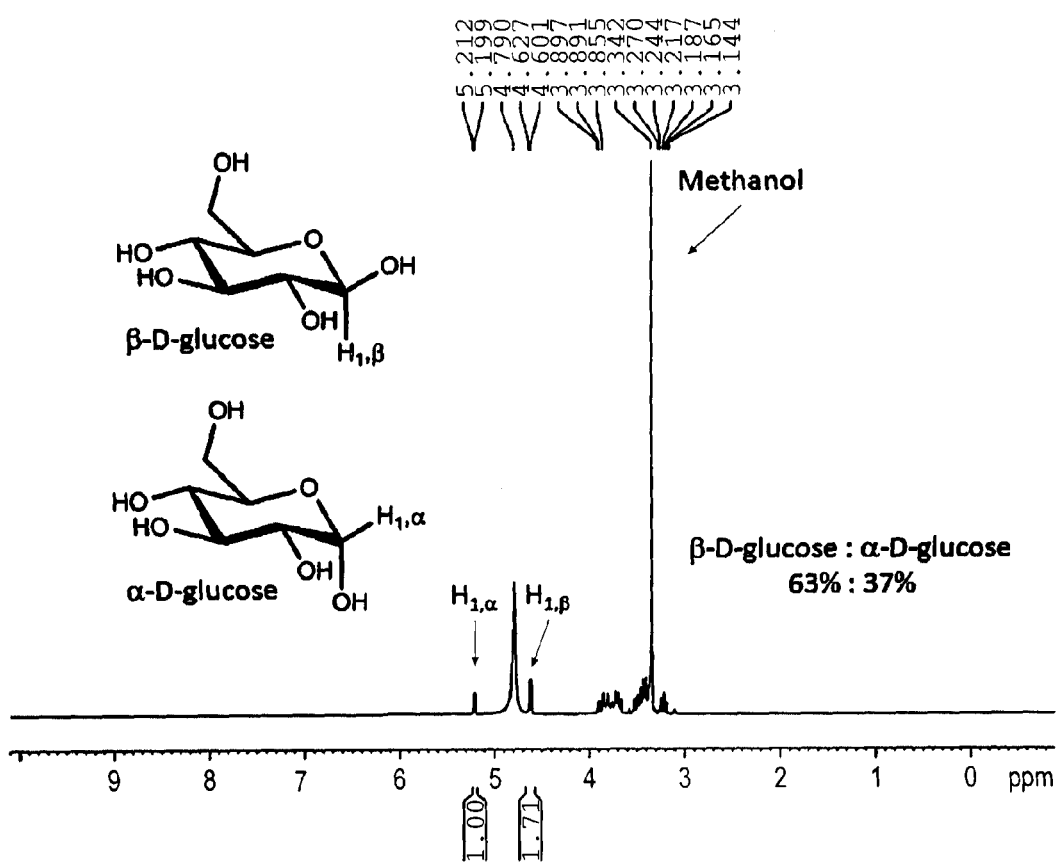
FIG. 27 is the $^1$H-NMR of glucose.
Figure 28:
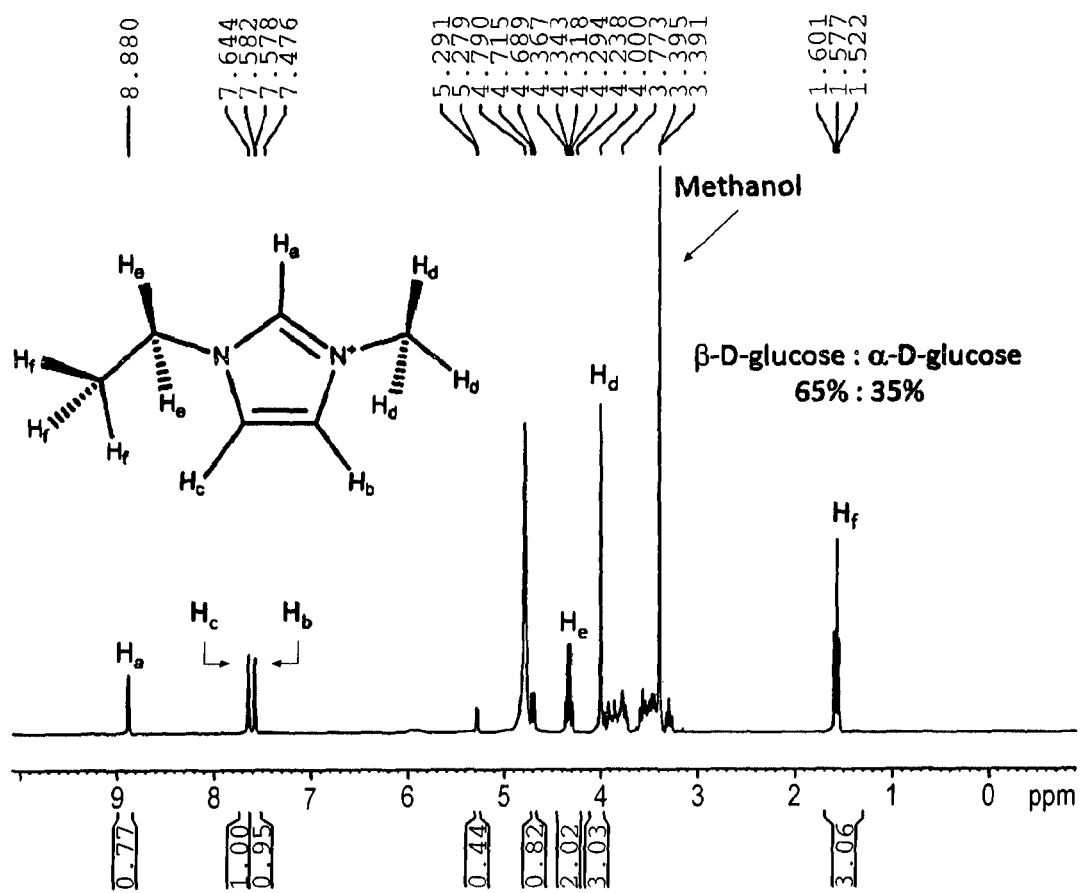
FIG. 28 is the $^1$H-NMR of glucose and IL.
Figure 29:
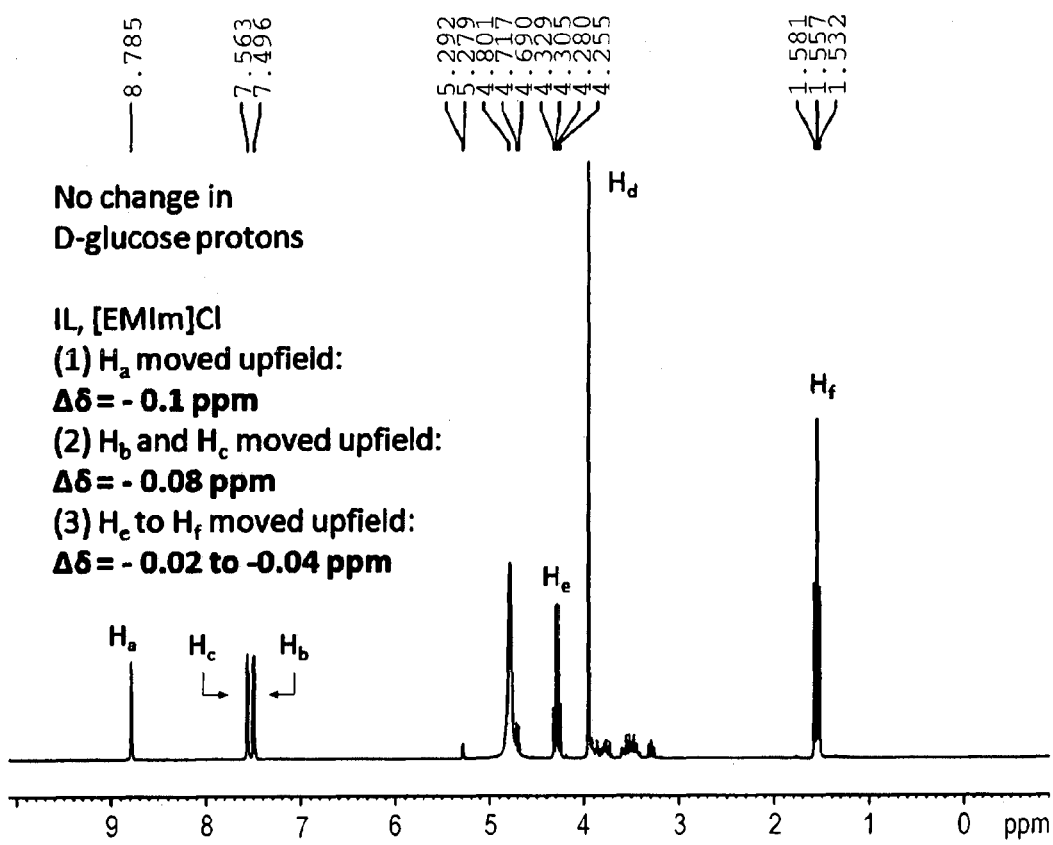
FIG. 29 is the $^1$H-NMR of glucose+IL+1 $(B(OH)_3$.
Figure 30A:
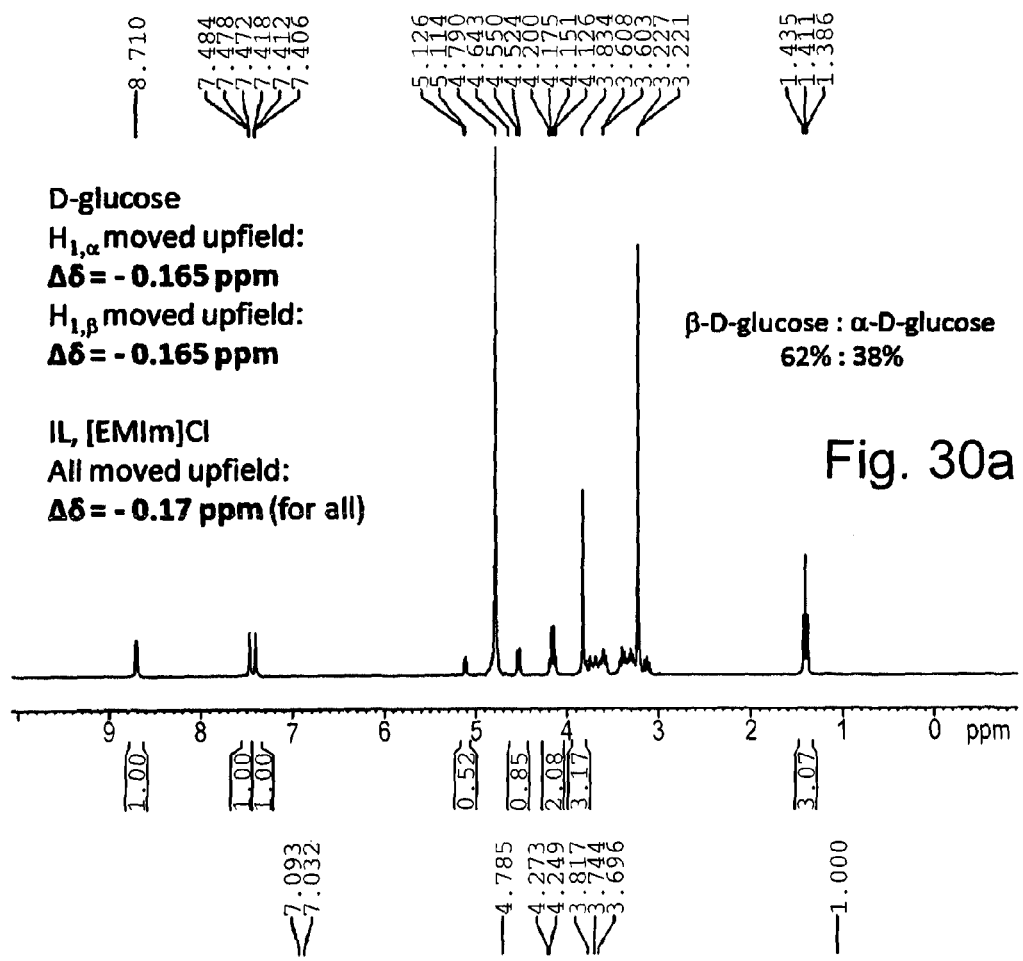
FIG. 30 shows the $^1$H-NMR spectra of glucose+IL+compound 2p (FIG. 30a) and of glucose+IL+compound 2p+NaOH (FIG. 30b).
Figure 30B:
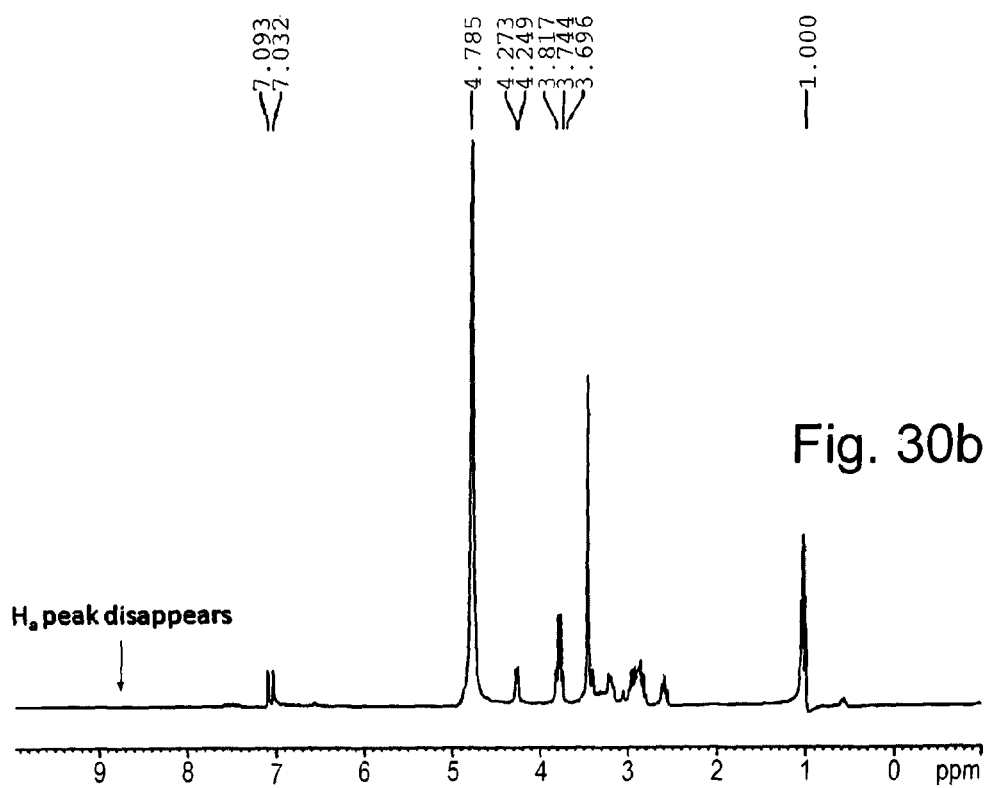
Figure 31A:
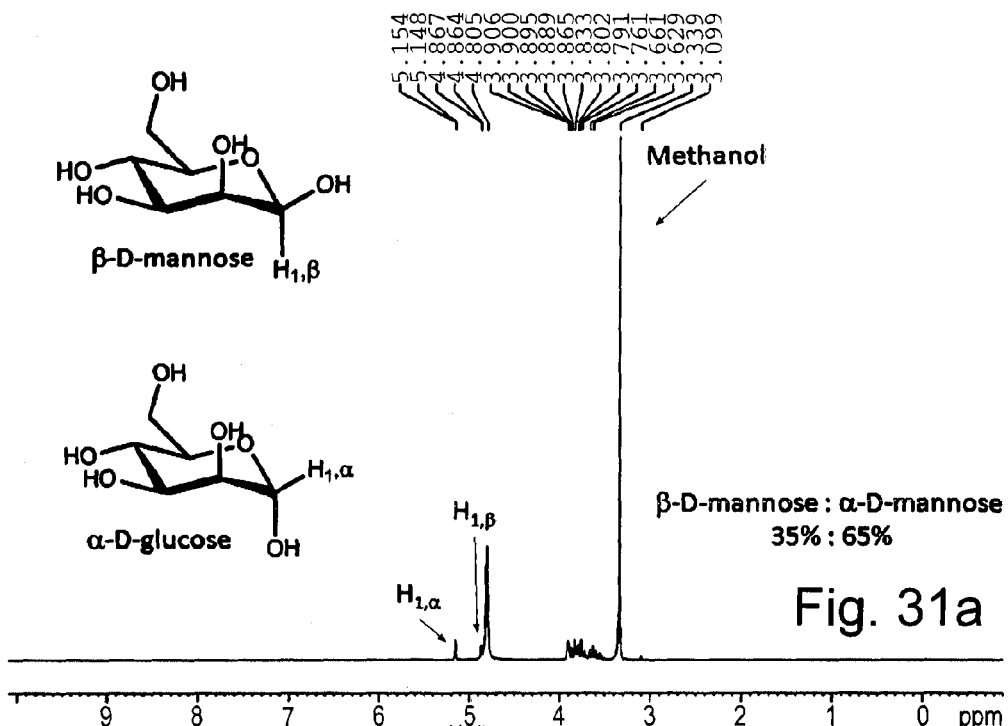
FIG. 31 shows the $^1$H-NMR spectra of mannose (FIG. 31a) and of mannose+IL (FIG. 31b).
Figure 31B:
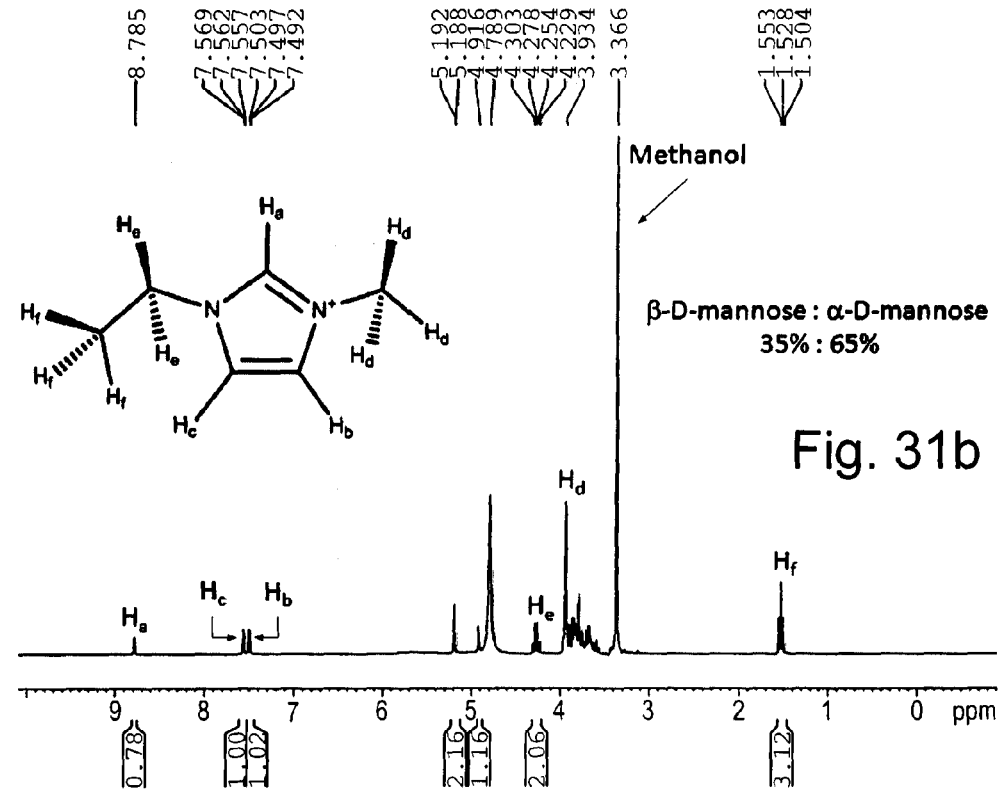
Figure 32A:
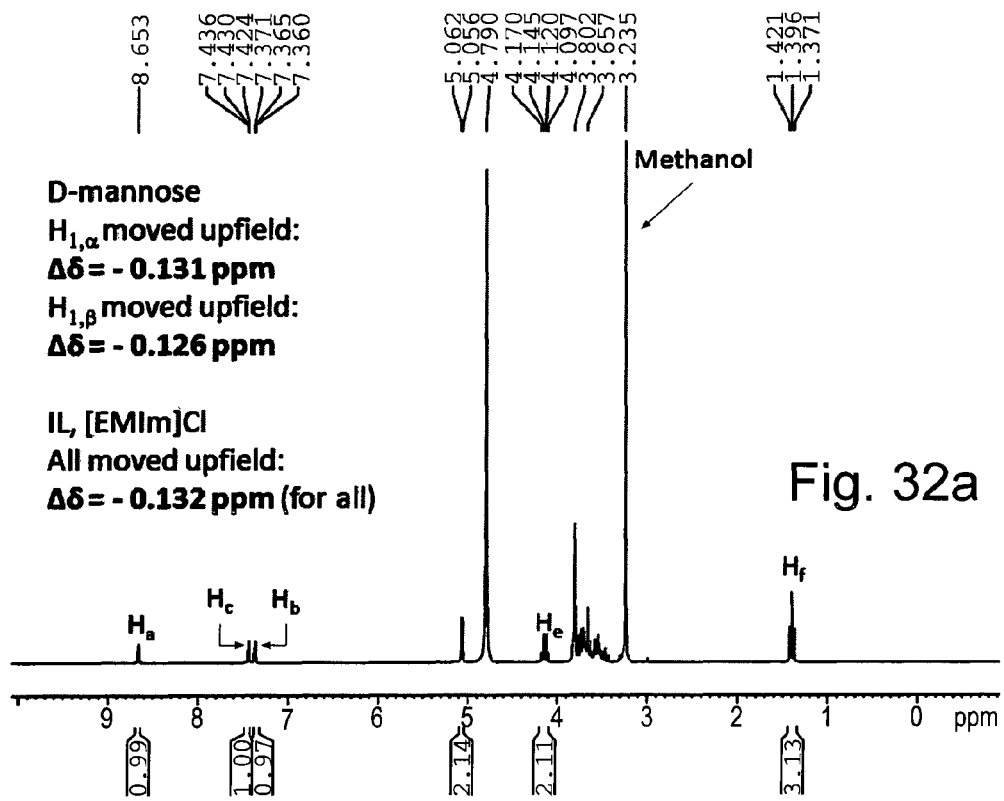
FIG. 32 shows the $^1$H-NMR spectra of mannose+IL+compound 2p (FIG. 32a) and of galactose (FIG. 32b).
Figure 32B:
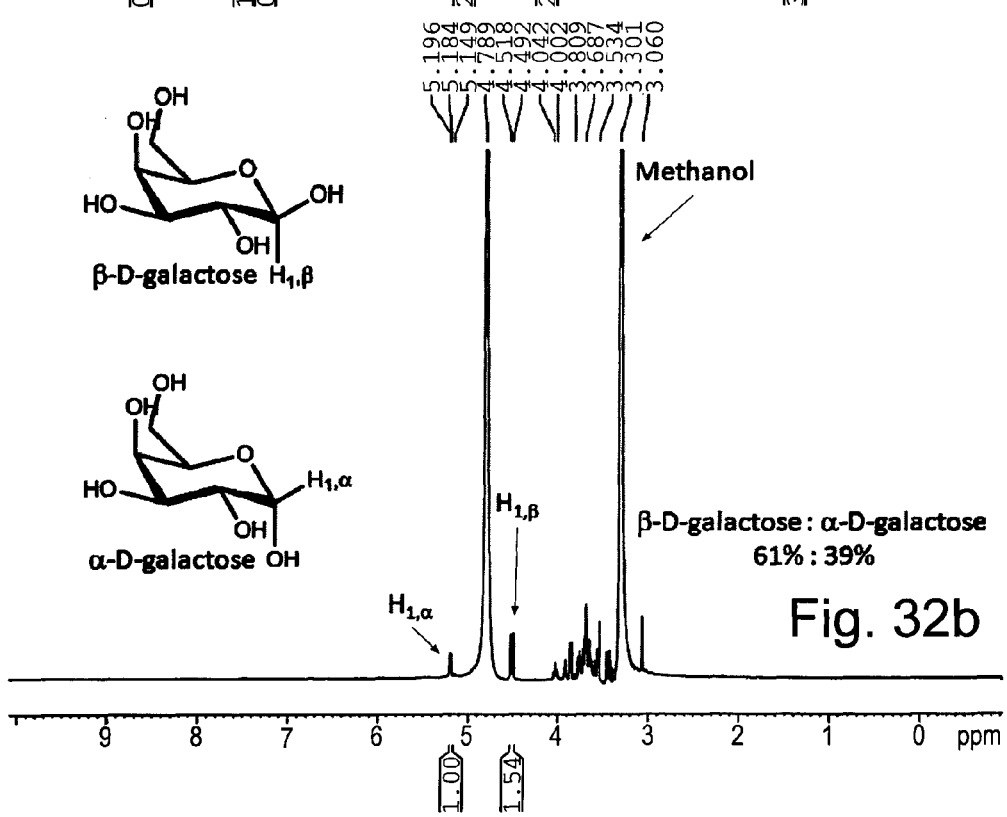
Figure 33A:
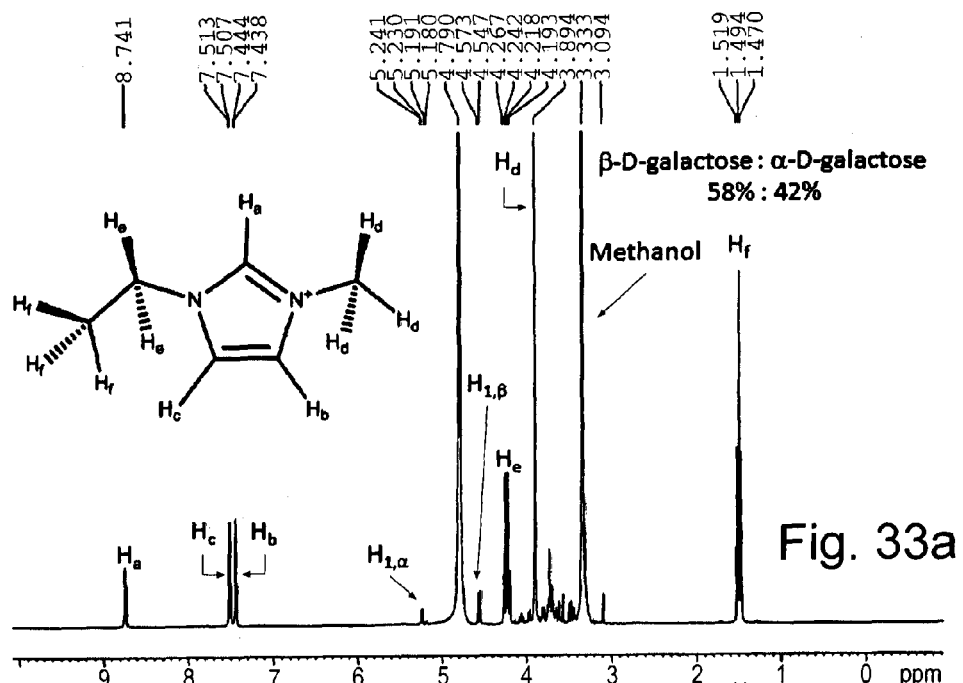
FIG. 33 shows the $^1$H-NMR spectra of galactose+IL (FIG. 33a) and of galactose+IL+compound 2p (FIG. 33b).
Figure 33B:
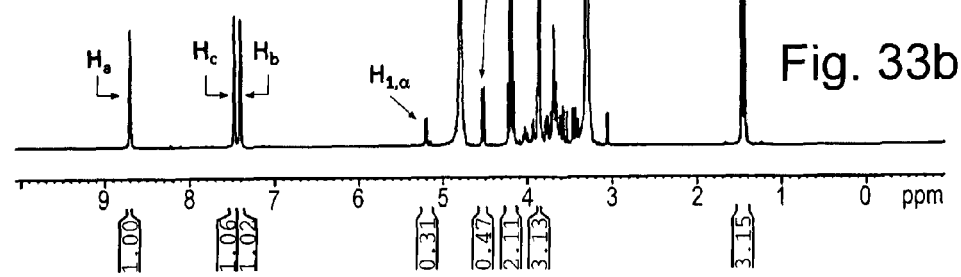
Figure 34A:
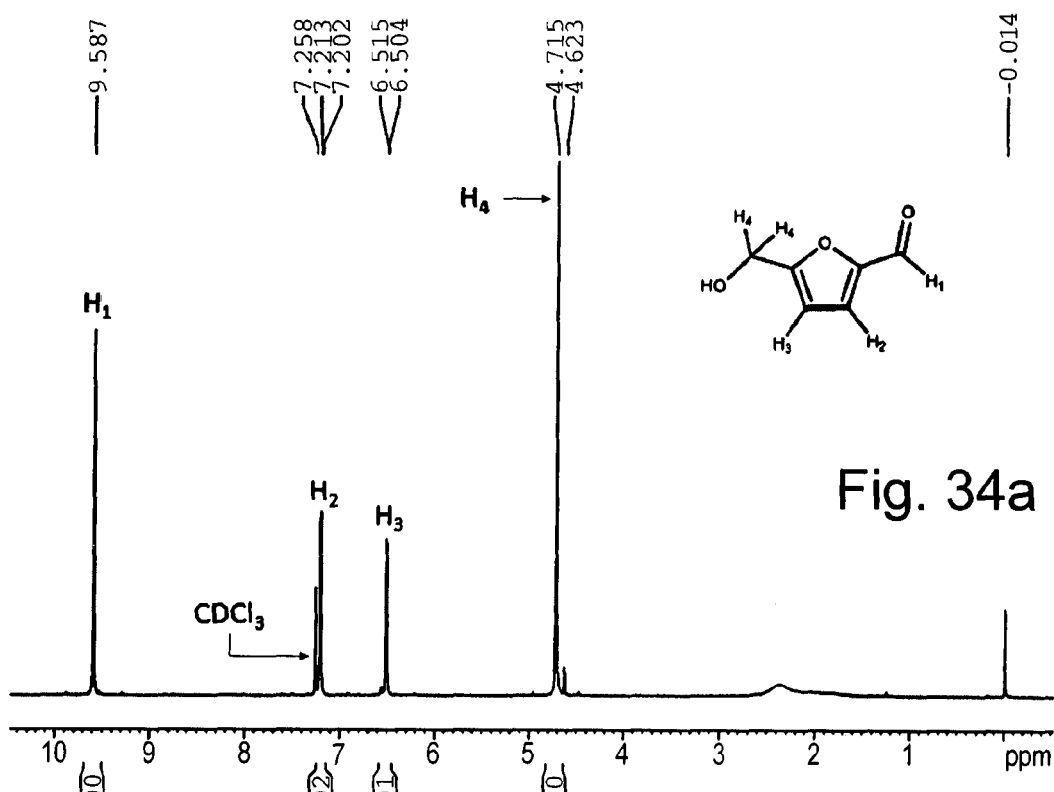
FIG. 34 shows the $^1$H-NMR spectrum of HMF (FIG. 34a) and the $^{13}$C-NMR spectrum of HMF (FIG. 34b).
Figure 34B:
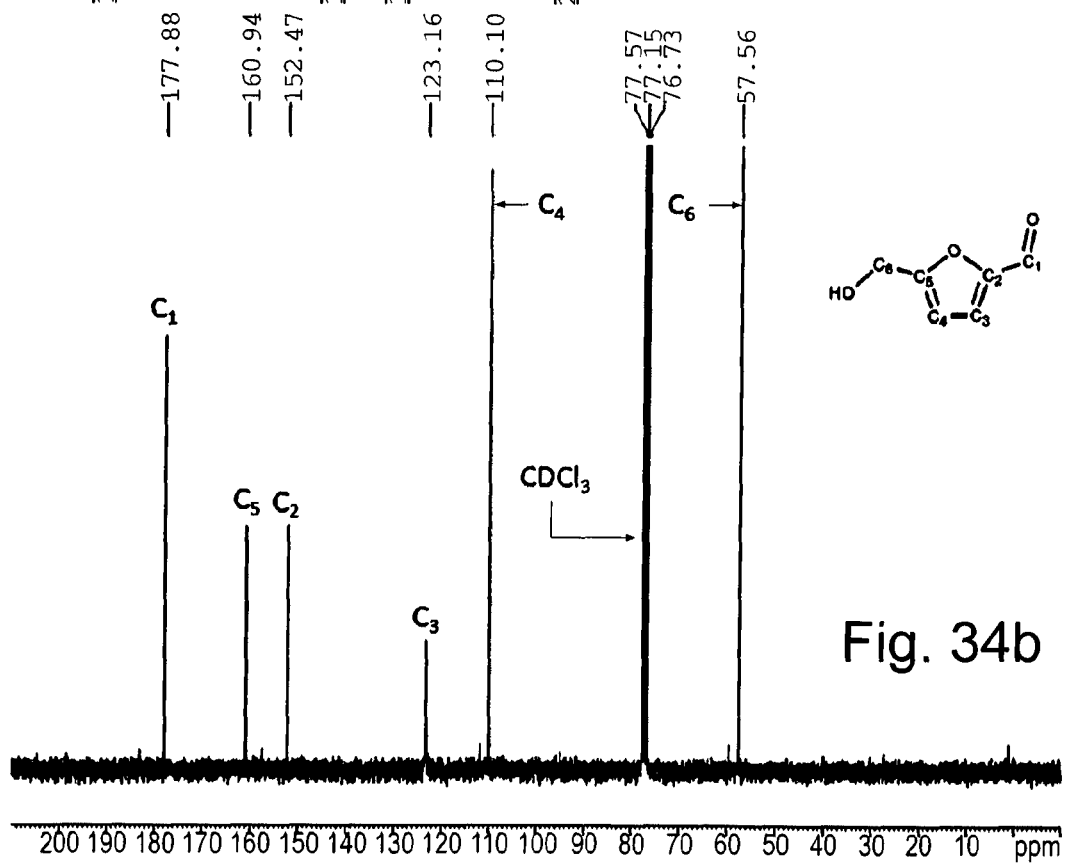

NMR Studies. NMR studies in $D_2O$ were done to gain insights into the mechanisms (FIG. 14). $D_2O$ was used as a solvent to remove broad —OH resonances from the spectra. First, the $^1H$ NMR experiment (300 MHz, $D_2O$) indicated that the catalyst 2p interacted with [EMIm]Cl which caused the shielding of the $H_a$ proton by about −0.17 ppm downfield change in chemical shift (−δ). Other protons of the IL in the sample with 2p also experienced similar shielding effects of −0.17 ppm. Boric acid 1, on the other hand, had a much smaller shielding effect. The biggest change by both 1 and 2p on IL seems to be on the $H_a$ proton.

The acidity of the $H_a$ proton was evidenced by the disappearance of the [EMIm]Cl singlet peak at δ 8.75 ppm when pH is increased on a separate experiment. Furthermore, integration of the IL only $^1H$ NMR spectrum revealed that some $H_a$ protons were lost through exchange with $D_2O$, an indication that it was labile. However, when the IL was mixed with catalyst 2p in $D_2O$, the $H_a$ protons remained intact without exchange with the solvent. Although the purpose of this interaction and participation of the imidazolium chloride IL during the actual reaction is unclear, many have suggested the formation of an N-heterocyclic carbene (NHC) that activates Lewis acid catalysts during reactions due to proton transfers between [EMIm]$^+$ and the chloride anion, thought to be sufficiently basic.[39] In the case of 2p, however, the acidity of the IL and thus its propensity to form NHC was reduced, indicating a different form of interaction.

Protons in D-glucose also experienced the same phenomenon. The anomeric carbon protons $H_{1\beta}$ and $H_{1\alpha}$ in the sample with 1 had their peaks moved downfield by +0.001 ppm, while the sample with 2p had them significantly moved up-field (−δ) instead by −0.165 ppm for both $H_{1\beta}$ and $H_{1\alpha}$. The other glucose protons were also observed to shift correspondingly; downfield for sample with 1 and upfield for sample with 2. These indicated de-shielding of protons in the sample with 1, and shielding of protons in sample with 2p, which might have been sterically-induced. Steric effects were thought to be able to cause downfield shifts in $^1H$ NMR when the C—H bonds are compressed, and upfield shifts when lengthened.[40] It is reasonable to think of these effects as coming from molecular distortions. However, magnetic anisotropy effects by the aromatic ring in 2p could not be discounted, and may have contributed to some extent. Next, the $^{13}C$ NMR (300 MHz, $D_2O$) was studied with the same conclusion obtained. In the sample with 1, D-glucose $^{13}C$ peaks were observed to have moved downfield by about +0.02 to +0.07 ppm, while in the sample with 2p, both [EMIm]Cl and D-glucose peaks were observed to have moved upfield instead by about −0.02 ppm. In the samples studied, preference for anomers by 2p was not observed. Broad spectrums were obtained when $CrCl_2$ were used. These results showed that interactions between 2p, solvent and monosaccharide are different from the ones employed by metal Lewis acid $CrCl_2$ and 1. Furthermore, 2p probably uses steric effects more than 1 to influence the reaction. When repeated with samples containing D-glucose epimers, results were consistent in the effects of 2p, although magnitude of chemical shifts varied.

Scheme 9: NMR study with the following labeled protons and carbon studied.

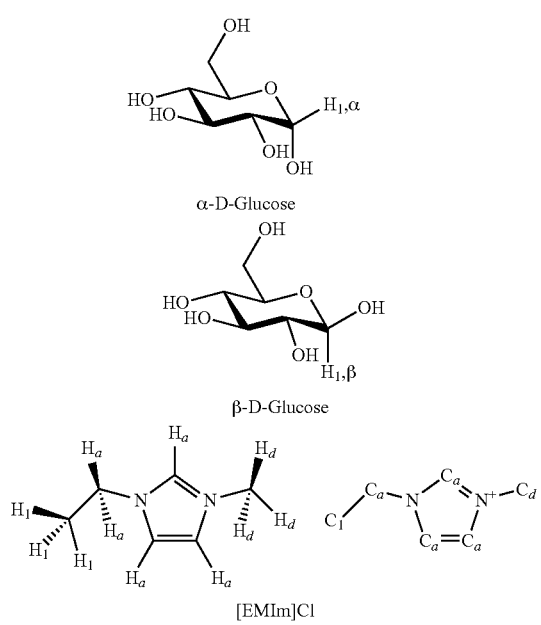

Modified Mechanism and Clues to Catalyst Design. Thus, following on these findings, the mechanism for D-glucose dehydration to HMF could be adjusted with the following:

(1) In the reaction, 2p was trapped by the 1° alcohol group to form the first 6-membered cyclic boronate ester with the vicinal diols at 4,6-positions.

(2) 2p then repositions itself to the more stable 5-membered cyclic boronate ester with vicinal diols at the 3,4-positions or 2,3-positions to catalyse the formation of the open-chain D-glucose form 5, by sterically inducing molecular distortions in the closed-ring form, which then isomerises to the D-fructofuranose boronate complex 7, (3) Hydrolysis via freed water molecules proceeds to form the free 2p catalyst and the free D-fructose substrate, which dehydrates quickly to HMF or complexes with 2p.

These information give clues required to design an efficient non-metal catalyst. Steric and electronic effects seem to play important roles in arylboronic acid's ability to catalyse the isomerisation of D-glucose to D-fructose with steric effects playing a more important role than the previously described boric acid 1.

Cellulose dehydration. The steps required before the dehydration of cellulose are dissolution and depolymerisation or hydrolysis. Through NMR studies, dissolution and hydrolysis were thought to be promoted by the IL through disruption of the inter- and intramolecular H-bondings and formation of a covalent bond between the anomeric $C_1$ carbon of glucose and $C_a$ of the imidazolium core.[41] In this reaction, it is proposed that boronic acid might have also promoted this dissolution and hydrolysis as observed by the faster reaction rate observed during reaction with 2p. This could have been promoted through a few ways. The first is boronate ester formation with the non-reducing end, with hydroxyl groups on C-3 and C-4 (Scheme 10), and second is the promotion of the dehydration of the reducing end. Furthermore, once dehydration of the released glucose monomers starts, 3 equivalents of water would be released as the reaction progressed. These provided additional water for further hydrolysis or depolymerisation, and thus complete cellulose degradation and dehydration to HMF.

Scheme 10: Cellulose chain with non-reducing and reducing ends

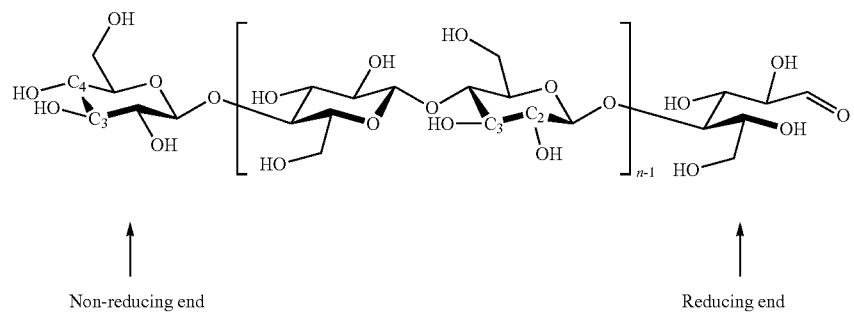

Non-reducing end

Reducing end

Co-catalysts. The mechanism proposed previously indicated that anionic boronate ester complex promoted the reaction via inductive effects to form the enediol intermediate 7. However, other studies with metal salts suggested that the metal Lewis acids interacted with the aldehyde and hydroxyl group on $C_2$, directly promoting the isomerisation of glucose (aldose) to fructose (ketose) via a 1,2-hydride shift without the need to form the enediol intermediate.

In addition, previous study done on boric acid found that boric acid inhibits fructose dehydration when used alone.[20] Similar results were obtained in this work with arylboronic acids, where 2d and 2p inhibited dehydration to HMF starting from fructose. However, when used in combination with NaCl, boric acid 1 was observed to efficiently catalyse and improve fructose dehydration to HMF in aqueous solution—an effect contrary to the inhibition induced in [EMIm]Cl IL solvent.[12] Furthermore, certain metal salts such as $CrCl_2$ were observed to be able to produce HMF from fructose at a lower temperature of 80° C. to give yields between 60 to 80%.[12]

When glucose is considered, metal salt NaCl was also observed to have improved HMF production from glucose with 1 in water.[42] Complementary metal salt catalysts which can hence promote a faster formation of fructose and its dehydration to HMF through cooperation with arylboronic acids, perhaps by selectively interacting with the hydroxyl groups on $C_1$ and $C_2$, while boronic acid complexes with the hydroxyl groups on $C_3$ and $C_4$.

The result of the preparation of HMF in the presence of co-catalysts are shown in FIG. 14 and Table S10

TABLE S10 additional use of a co-catalyst.

| Entry | Catalyst | Catalyst mol % | Co-catalyst | Catalyst mol % | Time | Glucose Conversion | HMF Yield | LA Yield |
|---|---|---|---|---|---|---|---|---|
| 1 | 2p | 20 | NaCl | 40 | 3 h | 96% | 43% | 9% |
| 2 | 2p | 20 | LiCl | 40 | 3 h | 80% | 37% | 6% |
| 3 | 2p | 20 | LiCl | 400 | 3 h | 83% | 37% | 6% |
| 4 | 2p | 20 | $AlCl_3$ | 40 | 3 h | 65% | 10% | 3% |
| 5 | 2p | 20 | $CuCl_2$ | 6 | 3 h | 99% | 23% | 6% |
| 6 | 2p | 20 | $FeCl_3$ | 6 | 3 h | 90% | 22% | 5% |
| 7 | 2p | 20 | $InCl_3$ | 10 | 3 h | 98% | 44% | 4% |
| 8 | 2p | 20 | $CrCl_2$ | 6 | 3 h | 99% | 66% | 3% |
| 9 | 2p | 20 | $CrCl_3$ | 6 | 3 h | 99% | 56% | 2% |
| 10 | 2p | 20 | $SnCl_4$ | 6 | 3 h | 95% | 38% | 6% |

The results showed that some metal salts do have an inhibiting effect on the reaction, while others enhance it. LiCl, $AlCl_3$, $CuCl_2$, $FeCl_3$, $SnCl_4$ were found to inhibit the reaction, NaCl and $InCl_3$ appeared to have little influence, while $CrCl_2$ had no influence and gave the yield with $CrCl_2$ alone. However, the reaction with anhydrous $CrCl_3$ showed that the chromium species might have acted as a co-catalyst in the reaction as it gave a yield of 56% HMF, higher than the yield with 2p alone, and higher than the reported yield with anhydrous $CrCl_3$ alone.[12] However, in line with the goal of this work, it is important that the co-catalyst also be nontoxic. Although NaCl was reported to improve HMF yield from aqueous glucose solution when reacted with boric acid, the results obtained with NaCl in the conditions used in this work showed a small decrease in HMF yield in [EMIm]Cl.[42]

2. Experimentals

Chemicals. D-(+)-Glucose (anhydrous, 99%) was purchased from Alfa Aesar, while D-(−)-Fructose (extra pure) was purchased from Merck. AH boronic acids, 6-deoxy-D-glucose and [EMIm]CI, were purchased from Sigma Aldrich. The chemicals were used as purchased without pre-treatment.

High Performance Liquid Chromatography (HPLC) analysis. The HPLC system used an Agilent 1100 series, with either (1) Alltech Alltima Cl 8 μm, 250 mm×3.0 mm pre-packed column, ACN/water (0.1% TFA) mobile phase, 30° C., 0.3 mL/min; or (2) ZORBAX Carbohydrate NTL 5 pm, 4.6×150 mm pre-packed analytical column, CAN/water (de-ionized) mobile phase, 30° C., 1.0 mL/min. The detector used was a multi-wavelength detector (MWD), scanning at 195 nm, 210 nm, 220 nm, 254 nm and 284 nm. The samples were first filtered before injecting 5 μL of both standard and experimental samples into the system. The solvent gradient profile used for sample analysis and the elution order of the peaks during each sample run are provided.

The wavelength (λ) used were chosen based on the UV-vis absorption spectra of the compounds of interest—glucose, fructose, HMF and LA. Individual and combined UV-vis absorption spectrum is given (Supporting Information).

The ZORBAX carbohydrate column used were able to resolve glucose and fructose well, but was only used after extraction as the column is sensitive to HMF. Prior to extraction, the C-18 column (1) could be used, but glucose and fructose resolution suffered as they were inseparable in time. Thus, different wavelengths (195 nm and 210 nm) were used to identify and quantify them as glucose showed almost no absorption at 210 nm, while fructose showed a much higher absorption, measurable at low concentrations. At 195 nm, both glucose and fructose signals were measured together, while at 210 nm, fructose could be quantified and subtracted from the signal at 195 nm to obtain the glucose only signal. The wavelengths used to observe HMF were 210, 220 and 254 nm as strong absorptions at other wavelengths caused deviations from the Beer-Lambert law. However, trace HMF could be measured using 284 nm, HMF's highest absorption maxima. LA was measured using 254 nm. When more than one wavelength was used, an average was taken to obtain more accurate measurements of the concentration. All compound identities were confirmed by analysis of pure components, which were also used to plot external standard calibration curves.

GC-MS and LC-MS analysis. The GC-MS system used was a ThermoFinnigan PolarisQ MS equipped with electrospray (ESI) ionization, Quadrupole ion trap mass spectrometer and Thermo Trace GC with silphenylene based stationary phase. Analysis was done using an injection temperature of 240° C., column temperature of 140° C. and flow rate of 1 mL/min using FL (g). The LC-MS system used was a ThermoFinnigan LCQ Fleet MS Quadrupole ion trap Mass Spectrometer equipped with Thermo Accela LC pump, autosampler, and detector. Analysis was done using 1 mL/min of MeOH/H$_2$O. Samples were dissolved in methanol and filtered using a hydrophobic syringe filter.

$^1$H and $^{13}$C NMR Study. NMR (300 MHz) studies of glucose, IL and catalysts 2$p$ and 1 were done using D$_2$O. Preparation involved simple mixing of the reactants under ambient conditions. Calibration of $^{13}$C NMR peaks with D$_2$O solvent was not possible, so methanol was added, and its peak calibrated to 49.50 ppm, as suggested by Gottlieb, Fl. E. et al.[44] Anomeric proton peaks for D-glucose were identified using J values, of which the f3-anomer has the larger J value (7.93 Hz) due to axial-axial coupling with about 180° dihedral angle. Anomeric carbon peaks were identified by comparing with previous work done by others.[43]

General Experimental methods. The methods following each step of the experiment are highlighted in the following sections, The dehydration experiments were performed under nitrogen atmosphere and under temperature control with ±1° C. variations in temperature. HMF yields and glucose conversion were measured by HPLC, while HMF isolated yields were measured as dry mass.

General dehydration procedure (glucose/fructose). A 10 mL reaction flask was charged with [EMIm]CI (1.0 g) and boronic acid (varying amounts) and heated at 100° C. for 30 minutes, following which vacuum was applied to degas the liquid mixture for another 30 minutes at 100° C. Glucose (0.1 g, 0.56 mmol) or fructose (0.1 g, 0.56 mmol) was then added carefully and the mixture stirred for 3 h at 120° C. After the reaction, the flask was cooled to room temperature and water (5 mL) was added. The solids were filtered off and the filtrate analysed by HPLC.

General dehydration procedure (cellulose). A 10 mL reaction flask was charged with [EMIm]CI, (1.0 g) and heated at 100° C. for 30 minutes, following which vacuum was applied to degas the liquid mixture for another 30 minutes at 100° C. Cellulose (90 mg, 0.56 mmol glucose monomers) was then added carefully, in portions of 4×20 mg and 1×10 mg over 30 minutes with stirring, and the solution stirred for another 30 minutes at 100° C. to allow complete dissolution of cellulose. Catalyst was then added and the solution stirred for 3 h at 120° C. After the reaction, the flask was cooled to room temperature and water (5 mL) was added. The solids were filtered off and the filtrate analysed by HPLC. For both dehydration procedures, the degassing method used is effective due to IL's unique low volatility property, with very little vapour pressure at high temperatures. The method removes gases such as O2 (g), which may be reactive in high temperatures.

Preparation of 6-O-tert-butyldiphenylsilyl-D-glucose. DMF (10 mL) was placed in a 50 mL flask and cooled to 0° C. in an ice bath. 5 g of D-glucose was added, followed by 0.9 molar equiv. (6.5 mL) of tert-butylchlorodiphenylsilane. The reaction was left for 21 h at 0° C., after which it was poured into 5 mL of ethyl acetate and washed with saturated NaHCO$_3$, brine, dried, isolated by flash column chromatography and evaporated to a yellow solid of 11 (30%). $^1$NMR [(300 MHz, CDCl3) 5 (ppm): 7.64 (m, 4 H), 7.32 (m, 6 H), 5.13-2.94 (m, 11 H), 1.0 (s, 9 H)], $^{13}$C NMR [(300 MHz, CDCl3) 8 (ppm): 135.5 (s, TBDPS-O), 135.4$_5$ (s, TBDPS-O), 133.3 (s, TBDPS-O), 133.2 (s, TBDPS-O), 133.0 (s, TBDPS-O), 132.9 (s, TBDPS-O), 129.6 (s, TBDPS-O), 129.5 (d, TBDPS-O), 127.6 (s, TBDPS-O), 127.5$_5$ (s, TBDPS-O), 96.6 (s, $C_{1,\beta}$), 92.6 (s, $C_{1,\alpha}$), 77.8 to 60.7 ($C_2$-$C_6$), 26.7 (s, TBDPS-O, 4° C.), 19.1 (s, TBDPS-O), 19.0 (s, TBDPS-O)].

5-(O-tert-butyldiphenylsilylmethyl)furfural (13). 11 was dehydrated to its corresponding furanyl compound 13 via the general dehydration procedure. $^1$H NMR [(300 MHz, CDCl$_3$) 5 (ppm): 9.56 (s, 1 H), 7.68 (m, 4 H), 7.43 (m, 6 H), 7.17 (d, J=3.6 Hz, 1 H), 6.44 (d, J=3.3 Hz, 1 H), 4.74 (s, 1 H), 1.09 (s, 9 H)], $^{13}$C NMR [(300 MHz, CDCl3) 5 (ppm): 177.6 (s), 160.9 (s), 152.1 (s), 135.5 (s, TBDPS-O), 132.7 (s, TBDPS-O), 129.9 (s, TBDPS-O), 127.8 (s, TBDPS-O), 122.2 (s), 109.6 (s), 59.2 (s), 26.7 (s, TBDPS-O, 4° C.), 19.2 (s, TBDPS-O) and LC-MS [m/z (relative abundance): 365 (20) with H$^+$, 387 (100) with Na$^+$, 382 (70) with NH$_4^+$].

5-Methylfurfural (14). 12 was dehydrated to its corresponding 5-methylfurfural compound 14 via the general dehydration procedure. $^1$H NMR [(300 MHz, CDCl3) 5 (ppm): 9.51 (s, 1 H), 7.16 (d, J=3.6 Hz, 1 H), 6.23 (d, J=3.6 Hz, 1 H), 2.42 (s, 3 H), $^{13}$C NMR [(300 MHz, CDCl3) 5

(ppm): 176.9 (s), 159.8 (s), 151.9 (s), 124.4 (s), 110.2 (s), 14.0 (s)] and LC-MS [m/z (relative abundance): 111 (11) with H$^+$, 96 (100) with H$^+$, 95 (17) with H$^+$].

HMF Isolation procedures. Alternatively, after the dehydration reaction, the filtrate was extracted with ethyl acetate (5×20 mL) and the solvent then removed in vacuo. The resultant oil was dissolved in a little ethyl acetate and loaded onto a preparative thin-layer chromatography (prep-TLC) plate (20×20 cm, silica gel) using a cotton-tipped glass pipette. The prep-TLC plate was run twice using a 1:1 ratio of hexane and ethyl acetate as the mobile phase. After the second run, the broad HMF band can be scrapped off the plate and rinsed in 5 mL ethyl acetate with vigorous stirring for 30 minutes. The resulting suspension was filtered and the filtrate solvent removed in vacuo to obtain an oily yellow compound (23 mg, 33%). The mass of this oil was measured using a digital weighing balance with up to 0.1 mg accuracy. $^1$H NMR [(300 MHz, CDCl3) 5 (ppm): 9.55 (s, 1 H), 7.21 (d, J–3.5 Hz, 1 H), 6.51 (d, J–3.4 Hz, 1 H), 4.70 (s, 2 H)], $^{13}$C NMR [(300 MHz, CDCl3) 5 (ppm): 177.9 (s), 160.9 (s), 152.5 (s), 123.2 (s), 110.1 (s), 57.6 (s)] and GC-MS [m/z (relative abundance) 69 (48), 81 (10), 97 (100), 109 (8), 326 (34)] were done to identify HMF and determine its purity.

Water insoluble product. The water insoluble compound at the end of the reaction was filtered, washed with 10 mL of water, dissolved in 20 mL ethyl acetate and washed with 5×10 mL of water, brine and finally dried to obtain a dark-red compound. $^1$H NMR comparison was done with the pure 2p spectrum and it was found to match relatively well. LC-MS at negative ion mode [m/z (relative abundance) 257 (11), 497 (100), 737 (8), 1032 (11)] was done to determine its identity and purity. Signal m/z 257 is the single 2p molecule, while m/z 497, 737 and 1032 is the condensed dimer, trimer and tetramer of 2p, respectively The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

REFERENCES

1. Kamm, B. *Angew. Chem.-tnt. Edit* 2007, 46, 5056-5058.
2. Matson, T. D.; Barta, K.; Iretskii, A. V.; Ford, P. C. *J. Am. Chem. Soc.* 2011, 133, 14090-14097.
3. Brownlie, D. *J. Soc. Chem. Ind.* 1940, 59, 671-675.
4. Mascai, M.; Nikitin, E. B. *Angew. Chem.-Int. Edit.* 2008, 47, 7924-7926.
5. (a) Corma, A.; Iborra, S.; Velty, A. *Chem. Rev.* 2007, 107, 2411-2502; (b) Dull, G., *Chem. Ztg* 1895, 216.
6. Rosatella, A. A.; Simeonov, 5. P.; Frade, R. F. M.; Afonso, C. A. M. *Green Chem.* 2011, 13 (4), 754-793.
7. Nisbet, H. B. *J. Inst. Petroleum* 1946, 32, 162-166.
8. Stahlberg, T.; Fu, W. J.; Woodley, J. M.; Riisager, A. *ChemSusChem* 2011, 4 (4), 451-458.
9. Nishiyama, Y.; Langan, P.; Chanzy, H. *J. Am. Chem. Soc.* 2002, 124, 9074-9082.
10. (a) Isogai, A.; Atalla, R. H. *Cellulose* 1998, 5, 309-319; (b) Pinkert, A.; Marsh, K. N.; Pang, S. S. *Ind. Eng. Chem. Res.* 2010, 49, 11121-11130.
11. Rantwijk, F. V.; Lau, R. M.; Sheldon, R, A. *Trends Biotechnol.* 2003, 21 (3), 131-138.
12. Zhao, H. B.; Holladay, J. E.; Brown, H.; Zhang, Z. C. *Science* 2007, 316 (5831), 1597-1600.
13. (a) Kuster, B. F. M. *Starch-Starke* 1990, 42, 314-321; (b) Vandam, H. E.; Kieboorn, A. P. G.; Vanbekkum, H. *Starch-Starke* 1986, 38, 95-101.
14. Cottier, L; Descotes, G. *Trends Heterocycl. Chem.* 1991, 2, 233-248.
15. (a) Hu, S. Q.; Zhang, Z. F.; Song, J. L; Zhou, Y. X.; Han, B. X. *Green Chem.* 2009, 11 (11), 17461749; (h) Zhang, Z. H.; Wang, Q. A.; Xie, H, B.; Liu, W. J.; Zhao, Z. B. *ChemSusChem* 2011, 4 (1), 131-138.
16. (a) Yong, G.; Zhang, Y. G.; Ying, J. Y. *Angew. Chem.-Int. Edit.* 2008, 47 (48), 9345-9348; (b) Li, C. Z.; Zhang, Z. H.; Zhao, Z. B. K. *Tetrahedron Lett.* 2009, 50 (38), 5403-5405; (c) Qi, X. H.; Watanabe, M.; Aida, T. M.; Smith, R. L. *Ind. Eng. Chem. Res.* 2008, 47 (23), 9234-9239.
17. Greenwood, N. N.; Earnshaw, A., *Chemistry of the Elements* (2nd ed.). Oxford: Butterworth-Heinemann., 1997; p 1020.
18. Khokhlova, E. A.; Kachala, V. V.; Ananikov, V. P. *ChemSusChem* 2012, 00, 1-8.
19. Scott, R. W.; Green, J. *Anal. Chem.* 1974, 46 (4), 594-597.
20. Stahlberg, T.; Rodriguez-Rodriguez, S.; Fristrup, P.; Riisager, A. *Chem.-Eur. J.* 2011, 17(5), 1456-1464.
21. Draffin, S. P.; Duggan, P. J.; Fallon, G. D. *Acta Cryst.* 2004, E60, 1520-1522,
22. (a) Narasaka, K.; Shimada, G.; Osoda, K.; Iwasawa, N. *Synthesis* 1991, 1171-1172; (b) Iwasawa, N.; Kato, T.; Narasaka, K. *Chem. Lett.* 1988, 1721.
23. Bhosale, S. H.; Rao, M. B.; Deshpande, V. V. *Microbiol. Rev.* 1996, 60, 280-300.
24. Assary, R. S.; Curtiss, L. A. *J. Phys. Chem. A* 2011, 115 (31), 8754-8760.
25. Antal, M. J.; Mok, W. S. L; Richards, G. N. *Carbohydr. Res.* 1990, 199 (1), 91-109.
26. (a) Amarasekara, A. S.; Williams, L. D.; C. E. C. *Carbohydr. Res.* 2008, 343, 3021-3024; (b) Haworth, W. N.; Hirst, E. L; Nicholson, V. S. *J. Chem. Soc.* 1927, 1513-1526; (c) Haworth, W. N.; Jones, W. G. M. *J. Chem. Soc.* 1944, 667.
27. (a) Qi, X. H.; Watanabe, M.; Aida, T. M.; Smith, R. L, *Catal. Commun.* 2009, 10 (13), 17711775; (b) Qi, X. H.; Watanabe, M.; Aida, T. M.; Smith, R. L. *ChemSusChem* 2009, 2 (10), 944946; (c) Qi, X. H.; Watanabe, M.; Aida, T. M.; Smith, R. L. *Green Chem.* 2009, 11 (9), 13271331; (d) Zhang, Z.; Liu, W. J.; Xie, H. B.; Zhao, Z. B. *Molecules* 2011, 16, 8463-8474; (e) Patil, S. K. R.; Lund, C. R. F. *Energy Fuels* 2011, 25, 4745-4755.

28. Lorand, J. P.; Edwards, J. O. *J. Org. Chem.* 1959, 24, 769-774.
29. (a) Pizer, R.; Tihal, C. *Inorg. Chem.* 1992, 31, 3243-3247; (b) Ferrier, R. *J. Adv. Carbohydr. Chem. Biochem.* 1978, 35, 31-80; (c) Shinkai, S.; Tsukagoshi, K.; Ishikawa, Y.; Kunitake, T. *J. Chem. Soc. Chem. Commun.* 1991, 1039-1041; (d) Kondo, K.; Shiomi, Y.; Saisho, M.; Harada, T.; Shinkai; S. *Tetrahedron* 1992, 48, 8239-8252.
30. (a) Babcock, L; Pizer, R. *Inorg. Chem.* 1980, 19, 56-61; (b) Branch, G. E. K.; Yabroff, D. L; Bettmann, B. *J. Am. Chem. Soc.* 1934, 56, 934-941; (c) Yabroff, D. L.; Branch, G. E. K.; Bettmann, B. *J. Am. Chem. Soc.* 1934, 56, 1850-1857; (d) Bettmann, B.; Branch, G. E. K.; Yabroff, D. L. *J. Am. Chem. Soc.* 1934, 56, 1865-1870.
31. (a) Cukalovic, A.; Stevens, C. V. *Green Chem.* 2010, 12 (7), 1201-1206; (b) Yan, H. P.; Yang, Y.; Tong, D. M.; Xiang, X.; Hu, C. W. *Catal. Commun.* 2009, 10 (11), 1558-1563.
32. Martichonok, V.; Jones, J. B. *Bioorg. Med. Chem.* 1997, 5, 679-684.
33. Kustin, K.; Pizer, R. *J. Am. Chem. Soc.* 1969, 91 (317-322).
34. Pizer, R. D.; Tihal, C. A. *Polyhedron* 1996, 15, 3411-3416.
35. Binder, J. B.; Raines, R. T. *J. Am. Chem. Soc.* 2009, 131 (5), 1979-1985.
36. Binder, J. B.; Cefali, A. V.; Blank, J. J.; Raines, R. T. *Energy Environ. Sci.* 2010, 3 (6), 765-771.
37. Sugihara, J. M.; Bowman, C. M. *J. Am. Chem. Soc.* 1958, 80 (10), 2443-2446.
38. Matteson, D. S.; Kim, G. Y. *Org. Lett.* 2002, 4, 2153-2155.
39. (a) Holloczki, 0.; Gerhard, D.; Massone, K.; Szarvas, L; Nemeth, B.; Veszpremi, T.; Nyulaszi, L. *New J. Chem.* 2010, 34, 3004-3009; (b) Scholten, J. D.; Ebeling, G.; Dupont, J. *Dalton Trans.* 2007, 5554-5560.
40. (a) Seidl, P. R.; Yoneda, J. D.; Leal, K. 2. *J. Phys. Org. Chem* 2005, 18, 162-166; (b) Seidl, P. R.; Leal, K. Z.; Yoneda, J. D. *J. Phys. Org. Chem* 2002, 15, 801-807.
41. Pinkert, A.; Marsh, K. N.; Pang, S. S.; Staiger, M. P. *Chem. Rev.* 2009, 109, 6712-6728.
42. Hansen, T. S.; Mielby, J.; Riisager, A. *Green Chem.* 2011, 13 (1), 109-114.
43. Harvey, F. World headed for irreversible climate change in five years, IEA warns, http://www.guardian.co.uk (accessed 25/11/2011).
44. Gottlieb, H. E.; Kotlyar, V.; Nudelman, A. *J. Org. Chem* 1997, 62, 7512-7515.
45. Gurst, J. E. *J. Chem. Educ.* 1991, 68 (12), 1003.

What is claimed is:

1. A method for preparing 5-(hydroxymethyl)furfural (HMF) comprising reacting a saccharide in the presence of an aryl- or heteroaryl-boronic acid, wherein the boronic acid is of the following formula (I):

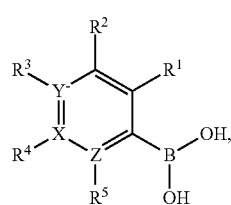

(I)

wherein, in formula (I), each of X, Y and Z are independently C, N, O, or S, or when at least one of Y, X, or Z is N, O or S, the ring comprising Y, X and Z may be a 5 or 6 membered ring;

$R^1$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$ alkoxy, $C_2$-$C_6$ alkenyl, $C_2$-$C_6$ alkynyl, —$CF_3$, —$CCl_3$, CHO, or $COR^6$;

$R^2$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$ alkoxy, $C_2$-$C_6$ alkenyl, $C_2$-$C_6$ alkynyl, —$CF_3$, —$CCl_3$, CHO, or $COR^6$;

$R^3$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$ alkoxy, $C_2$-$C_6$ alkenyl, $C_2$-$C_6$ alkynyl, —$CF_3$, —$CCl_3$, CHO, or $COR^6$;

$R^4$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$ alkoxy, $C_2$-$C_6$ alkenyl, $C_2$-$C_6$ alkynyl, —$CF_3$, —$CCl_3$, CHO, or $COR^6$;

$R^5$ is H, F, Cl, Br, I, $NO_2$, CN, alkyl, OH, —$NH_2$, —$NHR_2$, —$N(R)_2$, —$SO_2CH_3$, $SO_3H$, $C_1$-$C_6$ alkoxy, $C_2$-$C_6$ alkenyl, $C_2$-$C_6$ alkynyl, —$CF_3$, —$CCl_3$, CHO, or $COR^6$;

or wherein independently each of $R^1$ and $R^2$, $R^2$ and $R^3$, $R^3$ and $R^4$, $R^4$ and $R^5$ taken together form an optionally substituted ring of 5 or 6 atoms, wherein the atoms are independently selected from C, N, S and O; and wherein R is selected from H, and $C_1$-$C_6$ alkyl; and $R^6$ is selected from H, $C_1$-$C_6$ alkyl, OH, Ph, Cl, and Br; wherein the reaction is performed in the presence of a solvent, wherein the solvent is an ionic liquid; wherein the reaction is carried out in an inert nitrogen atmosphere; and wherein the reaction is performed at a temperature of 70 to 140° C.

2. The method according to claim 1, wherein least one of $R^1$ to $R^5$ is not H.

3. The method to claim 2, wherein $R^1$ to $R^5$ are independently selected from F, Cl, Br, I, $NO_2$, CN, —$SO_2CH_3$, $SO_3H$, $CF_3$, $CCl_3$, CHO and $COR_6$.

4. The method according to claim 1, wherein the aryl boronic acid is present and is selected from the group consisting of

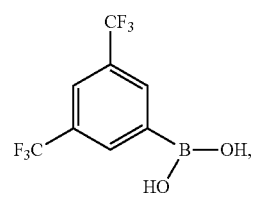

2p

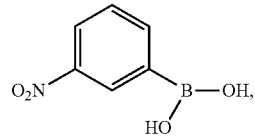

2o

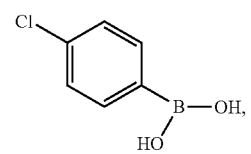

21

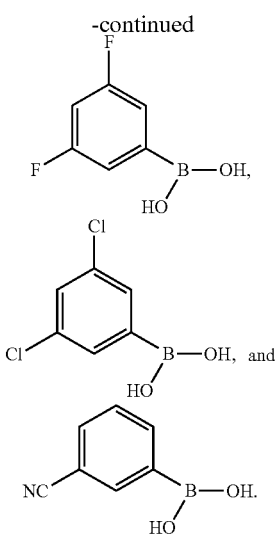

5. The method according to claim 1, wherein the saccharide is selected from glucose and cellulose.

6. The method according to claim 1, wherein the reaction is performed in the presence of a salt selected from the group consisting of NaCl, LiCl, AlCl$_3$, CuCl$_2$, MgCl$_2$, InCl$_3$, SnCl$_4$, CrCl$_2$ and CrCl$_3$.

7. The method according to claim 6, wherein the salt is selected from the group consisting of NaCl, MgCl$_2$, InCl$_3$, CrCl$_2$ and CrCl$_3$.

8. The method of claim 1, wherein the ionic liquid is selected from the group consisting of Ethyl-3-methylimidazolium Chloride ((EMIM)Cl), 1-Butyl-3-methylimidazolium hexafluorophosphate (BMIM-PF$_6$), 1-butyl-3,5-dimethylpyridinium bromide, and 1-butyl-3-methylimidazolium chloride.

9. The method according to claim 1, further comprising degasing a solution comprising the saccharide to remove oxygen and water;
adding N$_2$ to create the inert nitrogen atmosphere, and adding the aryl-or heteroaryl-boronic acid.

10. The method according to claim 1, wherein the reaction is performed at a temperature of 100 to 140° C.

11. The method according to claim 1, wherein the amount of aryl- or heteroaryl-boronic acid is from 5% to 150% of the moles of a saccharide monomer.

12. The method according to claim 1, wherein the conversion is performed within 3 to 7 h.

13. The method according to claim 1, wherein the conversion of the saccharide to HMF is a one pot conversion of cellulose to HMF or of glucose to HMF.

14. The method according to claim 10, wherein the reaction is performed at a temperature of 100 to 140° C.

15. The method according to claim 14, wherein the reaction is performed at a temperature of 110 to 120° C.

16. The method according to claim 11, wherein the amount of aryl- or heteroaryl-boronic acid is from 10% to 100% of the moles of a saccharide monomer.

17. The method according to claim 16, wherein the amount of aryl- or heteroaryl-boronic acid is from 15% to 25% of the moles of a saccharide monomer.

18. The method according to claim 17, wherein the amount of aryl- or heteroaryl-boronic acid is 20% of the moles of a saccharide monomer.

19. The method according to claim 9, wherein the degassing is performed under vacuum.

* * * * *